(12) United States Patent
Berget

(10) Patent No.: US 10,202,466 B2
(45) Date of Patent: Feb. 12, 2019

(54) LINKED PEPTIDE FLUOROGENIC BIOSENSORS

(71) Applicant: Carnegie Mellon University, Pittsburgh, PA (US)

(72) Inventor: Peter B. Berget, Philadelphia, PA (US)

(73) Assignee: CARNEGIE MELLON UNIVERSITY, Pittsburg, PA (US)

( * ) Notice: Subject to any disclaimer, the term of this patent is extended or adjusted under 35 U.S.C. 154(b) by 204 days.

(21) Appl. No.: 13/792,534

(22) Filed: Mar. 11, 2013

(65) Prior Publication Data

US 2013/0177924 A1 Jul. 11, 2013

Related U.S. Application Data

(63) Continuation of application No. 12/745,882, filed as application No. PCT/US2008/085415 on Dec. 3, 2008, now Pat. No. 8,426,153.

(60) Provisional application No. 61/005,122, filed on Dec. 3, 2007.

(51) Int. Cl.
| C07K 16/44 | (2006.01) |
| G01N 33/573 | (2006.01) |
| G01N 33/58 | (2006.01) |
| C12Q 1/37 | (2006.01) |
| G01N 33/542 | (2006.01) |

(52) U.S. Cl.
CPC ............... *C07K 16/44* (2013.01); *C12Q 1/37* (2013.01); *G01N 33/542* (2013.01); *G01N 33/573* (2013.01); *G01N 33/582* (2013.01)

(58) Field of Classification Search
None
See application file for complete search history.

(56) References Cited

U.S. PATENT DOCUMENTS

| 4,222,744 A | 9/1980 | McConnell |
| 4,355,023 A | 10/1982 | Ehrlich et al. |
| 4,462,334 A | 7/1984 | Kim |
| 4,704,692 A | 11/1987 | Ladner |
| 4,946,778 A | 8/1990 | Ladner et al. |
| 5,268,486 A | 12/1993 | Waggoner et al. |
| 5,486,616 A | 1/1996 | Waggoner et al. |
| 5,569,587 A | 10/1996 | Waggoner |
| 5,569,766 A | 10/1996 | Waggoner et al. |
| 5,595,895 A | 1/1997 | Miki et al. |
| 5,597,696 A | 1/1997 | Linn et al. |
| 5,616,502 A | 4/1997 | Haugland et al. |
| 5,627,027 A | 5/1997 | Waggoner |
| 5,702,892 A | 12/1997 | Mulligan-Kehoe |
| 5,750,373 A | 5/1998 | Garrard et al. |
| 5,821,047 A | 10/1998 | Garrard et al. |
| 5,948,635 A | 9/1999 | Kay et al. |
| 6,008,373 A | 12/1999 | Waggoner et al. |
| 6,048,982 A | 4/2000 | Waggoner |
| 6,127,132 A | 10/2000 | Breitling et al. |
| 6,225,050 B1 | 5/2001 | Waggoner |
| 6,437,099 B1 | 8/2002 | Jibu |
| 6,673,943 B2 | 1/2004 | Waggoner et al. |
| 6,716,994 B1 | 4/2004 | Menchen et al. |
| 7,741,128 B2 | 6/2010 | Su |
| 7,939,313 B2 | 5/2011 | Heyduk et al. |
| 8,426,153 B2* | 4/2013 | Berget .......................... 435/7.4 |
| 2004/0058881 A1 | 3/2004 | Humphreys et al. |
| 2005/0064512 A1 | 3/2005 | Schirner et al. |
| 2005/0214810 A1 | 9/2005 | Dallwig et al. |
| 2005/0215770 A1 | 9/2005 | Bell et al. |
| 2005/0221387 A1 | 10/2005 | Jibu |
| 2006/0019408 A1 | 1/2006 | Waggoner et al. |
| 2007/0212762 A1 | 9/2007 | Slater et al. |
| 2009/0068732 A1 | 3/2009 | Waldo |
| 2010/0041087 A1 | 2/2010 | Wang et al. |
| 2011/0003312 A1 | 1/2011 | Berget |
| 2013/0177924 A1 | 7/2013 | Berget |
| 2016/0033490 A1* | 2/2016 | Berget ................. G01N 33/542 435/7.4 |

FOREIGN PATENT DOCUMENTS

| CN | 1766623 A | 5/2006 |
| EP | 0368684 A1 | 5/1990 |
| EP | 1132397 A1 | 9/2001 |
| JP | 9-297135 A | 11/1997 |
| WO | 1988001649 A1 | 3/1988 |
| WO | 9102077 A1 | 2/1991 |
| WO | WO 2004/025268 A2 | 3/2004 |
| WO | WO 2008/092041 A2 | 7/2008 |
| WO | 2009079212 A2 | 6/2009 |

OTHER PUBLICATIONS

Rudikoff et al., "Single amino acid substitution altering antigen-binding specificity," PNAS USA, 1982, vol. 79, pp. 1979-1983.*
Adams, Stephen R., et al., "New Biarsentical Ligands and Tetracysteine Motifs for Protein Labeling in Vitro and in Vivo: Synthesis and Biological Applications," *J. Am. Chem. Soc.*, vol. 124, pp. 6063-6076 (2002).
Armentano et al., "Expression of human factor IX in rabbit hepatocytes by retrovirus-mediated gene transfer: Potential for gene therapy of hemophilia B," *Proc. Natl. Acad. Sci USA*, vol. 87, pp. 6141-6145 (1990).

(Continued)

*Primary Examiner* — Galina Yakovleva
(74) *Attorney, Agent, or Firm* — Pepper Hamilton LLP

(57) ABSTRACT

Biosensors, compositions comprising biosensors, methods of producing biosensors, and methods of using biosensors are disclosed. The biosensors comprise a fluorogen-activating peptide and a blocking peptide. The fluorogen-activating peptide and blocking peptide are covalently linked through a peptide linker. The blocking peptide associates with the fluorogen-activating peptide thereby blocking an active domain of the fluorogen-activating peptide when the linker is in an unmodified state. The peptide linker may contain an amino acid sequence that is specifically recognized as a modification substrate by a cognate enzyme. The fluorogen-activating peptide and the blocking peptide at least partially disassociate when the linker is modified by an enzyme, thereby allowing the fluorogen-activating peptide to bind a cognate fluorogen and modulate a fluorescence signal.

10 Claims, 36 Drawing Sheets
Specification includes a Sequence Listing.

(56) References Cited

OTHER PUBLICATIONS

Babendure, Jeremy R., et al., "Aptamers Switch on Fluorescence of Triphenylmethane Dyes," *J. Am. Chem.*, vol. 125, pp. 14716-14717 (2003).
Balint, Robert F. and James W. Larrick, "Antibody engineering by parsimonious mutagenesis," *Gene*, vol. 137, pp. 109-118 (1993).
Bark, Steven J. and Klaus M. Hahn, "Fluorescent Indicators of Peptide Cleavage in the Trafficking Compartments of Living Cells: Peptides Site-Specifically Labeled with Two Dyes," *Methods*, vol. 20, pp. 429-435 (2000).
Barker, Susan L. R., et al., "Cellular Applications of a Sensitive and Selective Fiber-Optic Nitric Oxide Biosensor Based on a Dye-Labeled Heme Domain of Soluble Guanylate Cyclase," *Anal. Chem.*, vol. 71, No. 9, pp. 2071-2075 (1999).
Barker, Susan L. R., et al., "Ratiometric and Fluorescence-Lifetime-Based Biosensors Incorporating Cytochrome c' and the Detection of Extra- and Intracellular Macrophage Nitric Oxide," *Anal. Chem.*, vol. 71 pp. 1767-1172 (1999).
Ben-Bassat et al., "Processing of the Initiation Methionine from proteins: Properties of the *Escherichia coli* Methionine Aminopeptidase and its Gene Structure," *J. Bacteriol.*, vol. 169, pp. 751-757 (1987).
Benhar, Itai, "Biotechnological applications of phage and cell display," *Biotechnology Advances*, vol. 19, pp. 1-33 (2001).
Berget, Peter B., "Pathways. New Probes for Networks and Pathways," Mar. 1, 2007; retrieved from http://www.esi-bethesda.com/ncrrworkshops/NTCNP/pdf/14-%20Berget.pdf on May 2, 2012.
Berkner, Kathleen L., "Development of Adenovirus Vectors for the Expression of Heterologous Genes," *BioTechniques*, vol. 6, No. 7, pp. 616-629 (1988).
Binz, H. Kaspar, et al., Engineering novel binding proteins from nonimmunoglobulin domains, *Nature Biotechnology*, vol. 23, No. 10, pp. 1257-1268 (2005).
Boder et al., "Directed evolution of antibody fragments with monovalent femtomolar antigen-binding affinity," *Proc. Natl. Acad. Sci USA*, vol. 97, pp. 10701-10705 (2000).
Boder et al., "Optimal Screening of Surface-Displayed Polypeptide Libraries," *Biotechnol. Prog.*, vol. 14, pp. 55-62 (1988).
Boder et al., "Yeast Surface Display for Directed Evolution of Protein Expression, Affinity and Stability, " *Methods in Enzymology*, vol. 328, pp. 430-444 (2000).
Boder et al., "Yeast surface display for screening combinational polypeptide libraries," *Nature Biotechnology*, vol. 15, pp. 553-557 (1997).
Bradbury, Andrew, "Selecting by microdialysis," *Nature Biotechnology*, vol. 10, pp. 528-529 (2001).
Brisson, N., et al. "Expression of bacterial gene in plants by using a viral vector," *Nature*, vol. 310 pp. 511-514 (1984).
Broach, James R., et al. "Vectors for High-Level, Inducible Expression of Cloned Genes in Yeast," *Experimental Manipulation of Gene Expression*, pp. 83-117 (1983).
Brown, S.D., et al., The promoter for the procyclic acidic repetitive protein (PARP) genes of Trypanosoma brucei shares features with RNA polymerase I promoters, *Mol. Cell. Biol.*, vol. 12, No. 6 (1992).
Bujarski, J.J. and P. Kaesberg, "DNA inserted two bases down from the initiation site of a SP6 polymerase transcription vector is transcribed efficiently in vitro," *Nucleic Acids Research*, vol. 15, p. 1337 (1987).
Carrero, Jenny and Edward W. Voss, Jr., "Temperature and pH Dependence of Fluorescein Binding within the Monoclonal Antibody 9-40 Active Site as Monitored by Hydrostatic Pressure," *The Journal of Biological Chemistry*, vol. 271, No. 10, pp. 5332-5337 (1996).
Cepko, Constance and Warren Pear, "Detection of Helper Virus in Retrovirus Stocks," *Current Protocols in Molecular Biology*, unit 9.13.1-9.13.6 (1996).
Cepko, Constance and Warren Pear, "Retrovirus Infection of Cells In Vitro and In Vivo," *Current Protocols in Molecular Biology*, unit 9.14.1-9.14.6 (1996).
Cepko, Constance and Warren Pear, "Transduction of Genes Using Retrovirus Vectors," *Current Protocols in Molecular Biology*, unit 9.9.1-9.9.16 (2000).
Chamberlain, Chester and Klaus M. Hahn, "Watching Proteins in the Wild: Fluorescence Methods to Study Protein Dynamics in Living Cells," *Traffic*, vol. 1, pp. 755-762 (2000).
Chen, Gang, et al., "Isolation of high-affinity ligand-binding proteins by periplasmic expression with cytometric screening (PECS)," *Nature Biotechnology*, vol. 19, pp. 537-542 (2001).
Chao, G. et al., "Isolating and engineering human antibodies using yeast surface display," *Nat. Protocols*, vol. 1, 755-768 (2006).
Cheng, X. et al., "The structure of bacteriophage T7 lysozyme amidase and an inhibitor of T7 RNA polymerase," *Proc. Natl. Acad. Sci. USA*, vol. 91, pp. 4034-4038 (1994).
Chowdhury, J. Roy, et al., "Long-Term Improvement of Hypercholesterolemia After ex Vivo Gene Therapy in LDLR-Deficient Rabbits," *Science*, vol. 254, pp. 1802-1805 (1991).
Colby, D.W. et al., "Development of a Human Light Chain Variable Domain (VL) Intracellular Antibody Specific for the Amino Terminus of Huntingtin via Yeast Surface Display," *J. Mol. Biol.*, vol. 342. pp. 901-912 (2004).
Colby, David W., et al., "Engineering Antibody Affinity by Yeast Surface Display," *Devices, Antibodies, and Vaccines*, vol. 18, pp. 348-358 (2004).
Coloma, M. Josefina and Sherie L. Morrison, "Design and production of novel tetravalent bispecific antibodies," *Nature Biotechnology*, vol. 15, pp. 159-163 (1997).
Coruzzi, Gloria, et al., "Tissue-specific and light-regulated expression of a pea nuclear gene encoding the small subunit of ribulose-1,5-bisphosphate carboxylase," *The EMBO Journal*, vol. 3, No. 8, pp. 1671-1679 (1984).
Cristiano et al., Hepatic gene therapy: Adenovirus enhancement of receptor-mediated gene delivery and expression in primary hepatocytes,: *Proc. Natl. Acad. Sci USA*, vol. 90, pp. 2122-2126 (1993).
Culp, Sandra J., et al., "Toxicity and metabolism of malachite green and leucomalachite green during short-term feeding to Fischer 344 rats and B6C3F$_1$ mice, " *Chemico-Biological Interactions*, vol. 122, pp. 153-170 (1999).
Cunningham, Brian C, and James A. Wells, "High-Resolution Epitope Mapping of hGH-Receptor Interactions by Alanine-Scanning Mutagenesis," *Science*, vol. 244, pp. 1081-1085 (1989).
Cürten, Beate, et al., "Synthesis, Photophysical, Photochemical and Biological Properties of Caged GABA, 4[[(2H-1-Benzopyran-2-one-7amino-4-methoxy) carbonyl] amino] Butanoic Acid," *Photochemistry and Photobiology*, vol. 81, pp. 641-648 (2005).
Cwirla, Steven E., et al., "Peptides on phage: A vast library of peptides for identifying ligands," *Proc. Natl. Acad. Sci.*, vol. 87, pp. 6378-6382 (1990).
Dai et al., "Gene therapy via primary myoblasts: Long-term expression of factor IX protein following transplantation in vitro," *Proc. Natl. Acad. Sci. USA*, vol. 89, pp. 10892-10895 (1992).
Danos and Mulligan, "Safe and efficient generation of recombinant retroviruses with amphotropic host ranges," *Proc. Natl. Acad. Sci USA*, vol. 85, pp. 6460-6464 (1988).
De Lorenzo, V., et all, "Operator Sequences of the Aerobactin Operon of Plasmid CoIV-K30 Binding the Ferric Update Regulation fur) Repressor," *Journal of Bacteriology*, vol. 169, pp. 2624-2630 (1987).
Derossi, Daniele, et al., "Cell Internalization of the Third Helix of the Antennapedia Homeodomain is Receptor-independent," *The Journal of Biological Chemistry*, vol. 271, No. 30, pp. 18188-18193 (1996).
Derossi, Daniele, et al., "The Third Helix of the Antennapedia Homeodomain Translocates through Biological Membranes," *The Journal of Biological Chemistry*, vol. 269, No. 14, pp. 10444-10450 (1994).
Devlin, James J., et al., "Random Peptide Libraries: A Source of Specific Protein Binding Molecules," *Science*, vol. 249, pp. 404-406 (1990).
Dooley, Colette T., et al., "Imaging Dynamic Redox Changes in Mammalian Cells with Green Fluorescent Protein Indicators," *The Journal of Biological Chemistry*, vol. 279, No. 21, pp. 22284-22293 (2004).

(56) References Cited

OTHER PUBLICATIONS

Dubendorff, John W., and F. William Studier, "Controlling Basal Expression in an Inducible T7 Expression System by Blocking the Target T7 Promoter with lac Repressor," *J. Mol. Biol.*, vol. 219, pp. 45-59 (1991).
Duckert et al., "Prediction of proprotein convertase cleavage sites," *Protein Eng. Des. Sel.*, vol. 17, No. 1, pp. 107-112 (2004).
Duxbury, D., The Photochemistry and Photophysics of Triphenylmethane Dyes in Solid and Liquid Media, *Chem. Rev.*, vol. 93, pp. 381-433 (1993).
Falco et al., "scFv-based fluorogen activating proteins and variable domain inhibitors as fluorescent biosensor platforms," *Biotechnology Journal*, Jul. 15, 2009, vol. 4, Issue 9, pp. 1328-1336.
Farinas et al., "Receptor-mediated Targeting of Fluorescent Probes in Living Cells," *The Journal of Biological Chemistry*, vol. 274, No. 12, Issue of Mar. 19, pp. 7603-7606, 1999.
Feldhaus, Michael J., et al., "Flow-cytometric isolation of human antibodies from a nonimmune *Saccharomyces cerevisiae* surface display library," *Nature Biotechnology*, vol. 21, pp. 163-170 (2003).
Ferry et al., "Retroviral-mediated gene transfer into hepatocytes in vitro," *Proc. Natl. Acad. Sci. USA*, vol. 898, pp. 8377-8381 (1991).
Flotte et al., "Expression of the Cystic Fibrosis Transmemberane Conductance Regulator from a Novel Adeno-associated Virus Promoter," *J. Biol. Chem.*, vol. 268, pp. 3781-3790 (1993).
Flotte Terence R., et al., "Gene Expression from Adeno-associated Virus Vectors in Airway Epithelial Cells," *Am. J. Respir. Cell Mol. Biol.*, vol. 7, pp. 349-356 (1992).
Furstenberg et al., Ultrafast Excited—State Dynamics of DNA Fluorescent Intercalators: New Insight into the Fluorescence Enhancement Mechanism, *J. Am. Chem. Soc.*, vol. 128, pp. 7661-7669 (2006).
Giepmans, Ben N. G., et al., "The Fluorescent Toolbox for Assessing Protein Location and Function," *Science*, vol. 312, pp. 217-224 (2006).
Giudicelli, V. et al., "IMGT/LIGM-DB, the IMGT® comprehensive database of immunoglobulin and T cell receptor nucleotide sequences," *Nucleic Acids Res.* vol. 34, pp. D781-D784 (2006).
Goldberg, M.B. et al., "Transcriptional Regulatio by Iron of a *Vibrio cholerae* Virulence Gene and Homology of the Gene to the *Escherichia coli* Fur System," *Journal of Bacteriology*, vol. 172, pp. 6863-6870 (1990).
Goud, Bruno, et al., "Antibody-Mediated Binding of a Murine Ecotropic Moloney Retroviral Vector to Human Cells Allows Internalization But Not the Establishment of the Proviral State," *Virology*, vol. 163, pp. 251-254 (1988).
Graham, Frank L. and Ludvik Prevec, "Manipulation of Adenovirus Vectors," *Methods in Molecular Biology*, vol. 7, pp. 109-128 (1991).
Green, Maurice and Paul M. Loewenstein, "Autonomous Functional Domains of Chemically Synthesized Human Immunodeficiency Virus Tat Trans-Activator Protein," *Cell*, vol. 55, pp. 1179-1188 (1988).
Greener, Alan, et al., "An Efficient Random Mutagenesis Technique Using an *E. coli* Mutator Strain," *Molecular Biotechnology*, vol, 7, pp. 189-195 (1997).
Gregorevic, et al. ,"Systemic delivery of genes to striated muscles using adeno-associated viral vectors," *Nat. Med.*, Author Manuscript (16 pages); published in final form as *Nat Med.*, (Aug. 2004; vol. 10(8):828-34, Epub Jul. 25, 2004).
Grodberg, Jennifer, et al., "Alanine scanning mutagenesis of human erythropoietin identifies four amino acids which are critical for biological activity," *Eur. J. Biochem.*, vol. 218, pp. 597-601 (1993).
Gurley et al., "Upstream Sequences Required for Efficient Expression of a Soybean Heat Shock Gene," *Mol. Cell. Biol.*, vol. 6, pp. 559-565 (1986).
Gustin, Kurt, et al., "Characterization of the Role of Individual Protein Binding Motifs within the Hepatitis B Virus Enhancer I on X Promoter Activity Using Linker Scanning Mutagenesis," *Virology*, vol. 193, pp. 653-660 (1993).

Hahn, Klaus M., et al., "A Calcium-sensitive Fluorescent Analog of Calmodulin Based on a Novel Calmodulin-binding Fluorophore," *The Journal of Biological Chemistry*, vol. 265, No. 33, pp. 20335-20345 (1990).
Haj-Ahmad and Graham, "Development of a Helper-Independent Human Adenovirus Vector and Its Use in the Transfer of the Herpes Simplex VirusThymidine Kinase Gene," *Journal of Virology*, vol. 57, pp. 267-274 (1986).
Headley, V., et al., "Expression of aerobactin genes by Shigella flexneri during extracellular and intracellular growth," *Infection and Immunity*, vol. 65, No. 2, pp. 818-821 (1997).
Hermonat et al., "Use of adeno-associated virus as a mammalian DNA cloning vector: Transduction of neomycin resistance into mammalian tissue culture cells," *Proc. Natl. Acad. Sci. USA*, vol. 81, pp. 6466-6470 (1984).
Herz and Gerard, "Adenovirus=mediated transfer of low density lipoprotein receptor gene acutely accelerates cholesterol clearance in normal mice," *Proc. Natl. Acad. Sci. USA*, vol. 90, pp. 2812-2816 (1993).
Hess, Samuel T., et al., "Fluorescence Photoconversion Kinetics in Novel Green Fluorescent Protein pH Sensors (pHluorins)," *J. Phys. Chem. B*, vol. 108, pp. 10138-10148 (2004).
Hochman et al., "An Active Antibody Fragment (Fv) Composed of the variable Portions of Heavy and Light Chains," *Biochemistry*, vol. 12, No. 6 (1973).
Holt, Lucy J., et al. The use of recombinant antibodies in proteomics, *Current Opinion in Biotechnolgy*, vol. 11, pp. 445-449 (2000).
Hu, Wei-Gang, et al., "Humanization and mammalian expression of a murine monoclonal antibody against Venezuelan equine encephalitis virus," *Vaccine*, vol. 25, pp. 3210-3214 (2007).
Huber et al., "Retroviral-mediated gene therapy for the treatment of hepatocellular carcinoma: An innovative approach for cancer therapy," *Proc. Natl. Acad. Sci. USA.*, vol. 88, pp. 8039-8043 (1991).
Hunt, M.D., "Promoter and operator determinants for fur-mediated iron regulation in the bidirectional fepA-fes control region of the *Escherichia coli* enterobactin gene system," vol. 176, No. 13, pp. 3944-3955 (1994).
Hwu, Patrick, et al., Functional and Molecular Characterization of Tumor-Infiltrating Lymphocytes Transduced with Tumor Necrosis Factor-α cDNA for the Gene Therapy of Cancer in Humans, vol. 150, No. 9, pp. 4104-4115 (1993).
Ike, Yoshimasa, et al., "Solid phase synthesis of polynucleotides," *Nucleic Acids Research*, vol. 11, No. 2, pp. 477-488 (1983).
Iliades, Peter, et al., "Triabodies: single chain Fv fragments without a linker form trivalent trimers," *FEBS Letters*, vol. 409, pp. 437-441 (1997).
Inouye, Sumiko and Masayori Inouye, "Up-promoter mutations in the Ipp gene of *Escherichia coli,*" *Nucleic Acids Research*, vol. 13, No. 9 (1985).
Invitrogen Corporation, Chapter 7, "Theory of Binding Data Analysis, Fluroescence polarization Technical Resource Guide," Fourth Edition, pp. 1-158 (2006).
Itakura, Keiichi, et al., Expression in *Escherichia coli* of a Chemically Synthesized Gene for the Hormone Somatostatin, *Science*, vol. 198, pp. 1056-1063 (1977).
Itakura, Keiichi, et al., "Synthesis and Use of Synthetic Oligonucleotides," *Ann. Rev. Biochem*, vol. 53, pp. 323-356 (1984).
Jadhav, J.P., S. P. Govindwar, "Biotransformation of malachite green by *Saccharomyces cerevisiae* MTCC 463," *Yeast*, vol. 23, pp. 315-323, (Mar. 2004).
Jones et al., Quenched BODIPY Dye-Labeled Casein Substrates for the Assay of Protease Activity by Direct Fluorescence Measurement, *Analytical Biochemistry*, vol. 251, pp. 144-152 (1997).
Jones, Nicholas and Thomas Shenk, "Isolation of Adenovirus Type 5 Host Range Deletion Mutants Defective for Transformation of Rat Embryo Cells", *Cell*, vol. 17, pp. 683-689 (1979).
Jones, Peter T., et al., "Replacing the complementary-determining regions in a human antibody with those from a mouse," *Nature*, vol. 321, pp. 522-525 (1986).
Julan, Maryse Etienne, et al., The efficiency of cell targeting by recombinant retroviruses depends on the nature of the receptor and the composition of the artificial cell-virus linker, vol. 73, pp. 3251-3255 (1992).

(56) References Cited

OTHER PUBLICATIONS

Kay, Mark A., et al., "Hepatic Gene Therapy: Persistent Expression of Human α1-Antitrypsin in Mice after Direct Gene Delivery In Vivo," *Human Gene Therapy*, vol. 3, pp. 641-647 (1992).
Kerppola, Tom K., "Complementary methods for studies of protein interactions in living cells," *Nature Methods*, vol. 3, No. 12, pp. 969-971 (2006).
Kubin, R.F. and A.N. Fletcher, "Fluorescence Quantum Yields of Some Rhodamine Dyes," *Journal of Luminescence*, vol. 27, pp. 455-462 (1982).
Kunkel, Maya T., et al. "Spatio-temporal Dynamics of Protein Kinase B/Akt Signaling Revealed by a Genetically Encoded Fluorescent Reporter," *The Journal of Biological Chemistry*, vol. 280, No. 7, pp. 5581-5587 (2005).
Lemarchand et al., "Adenovirus-mediated transfer of a recombinant human α1-antitrypsin cDNA to human endothelial cells," *Proc. Natl. Acad. Sci. USA*, vol. 89, pp. 6482-6486 (1992).
Lowman, Henry B., et al., "Selecting High-Affinity Binding Proteins by Monovalent Phage Display," *Biochemistry*, vol. 30, pp. 10832-10838 (1991).
Magde et al., "Ficosecond Internal Conversion in Crystal Violet," *Chemical Physics Letters*, vol. 24, No. 1 (1974).
Marks, James D., et al., "By-passing Immunization Human Antibodies from V-gene Libraries Displayed on Phage," *J. Mol. Biol.*, vol. 222, pp. 581-597 (1991).
Marks, K.M., M. Rosinov, G.P. Nolan, "In Vivo Targeting of Organic Calcium Sensors via Genetically Selected Peptides," *Chem Biol.*, vol. 11, pp. 347-356 (Mar. 2004).
Martin, Brent R., et al., "Mammalian cell-based optimization of the biarsentical-binding tetracysteine motif for improved fluorescence and affinity," *Nature Biotechnology*, vol. 23, pp. 1308-1314 (2005).
Maynard et al., "High-level bacterial secretion of single-chain αβ T-cell receptors," *Journal of Immunological Methods*, vol. 306, pp. 51-67 (2005).
McLaughlin et al., "Adeno-Associated Virus General Transduction Vectors: Analysis of Proviral Structures," *J. Virol*, vol. 62, pp. 2718-2722 (1987).
Miesenböck, Gero, et al., "Visualizing secretion and synaptic transmission with pH-sensitive green fluorescent proteins," *Nature*, vol. 394, pp. 192-195 (1998).
Miller et al., "N-terminal methionine-specific peptidase in *Salmonella typhimurium*," *Proc. Natl. Acad. Sci. USA*, vol. 84, pp. 2718-2722 (1987).
Miller, A.D., "Progress Toward Human Gene Therapy," *Blood, The Journal of the American Society of Hematology*, vol. 76, pp. 271-278 (1990).
Miller, Lawrence W. and Virginia W. Cornish, "Selective chemical labeling of proteins in living cells," *Current Opinion in Chemical Biology*, vol. 9, pp. 56-61 (2005).
Mizuno, Masaaki, et al., "Basic Research for Interferon Gene Therapy against Malignant Glioma," *Neurol Surg.*, vol. 20, No. 5, pp. 551-560 (1992). Abstract.
Mizuno, Masaaki, et al., "Growth Inhibition of Glioma Cells by Liposome-mediated Cell Transfection with Tumor Necrosis Faxtor-α Gene," *Neurol Med Chir*, vol. 32, pp. 873-876 (1992).
Motulsky, H., "The GraphPad Guide to Analyzing Radioligand Binding Data," *GraphPad Software, Inc.*, pp. 1-19 (1996).
Mujitaba et al., "Structure and acetyl-lysine recognition of the bromodomain," *Oncogene*, vol. 26, pp. 5521-5527 (2007).
Mujumdar, et al. "Cyanine Dye Labeling Reagents: Sulfoindocyanine Succinimidyl Esters," *Bioconjug. Chem.*, vol. 4, pp. 105-111 (Mar.-Apr. 1993).
Mulligan, Richard C., "The Basic Science of Gene Therapy," *Science*, vol. 260, pp. 926-932 (1993).
Muzyczka, N., "Use of Adeno-Associated Virus as a General Transduction Vector for Mammalian Cells," *Current Topis in Microbiology and Immunology*, vol. 158, pp. 97-129 (1992).
Myers, Richard M., et al., "Fine Structure Genetic Analysis of a β-Globin Promoter," *Science*, vol. 232, pp. 613-618 (1986).
Nagashima, Mariko, et al., "Alanine-scanning Mutagenesis of the Epidermal Growth Factor-like Domains of Human Thrombomodulin Identifies Critical Residues for Its Cofactor Activity," *The Journal of Biological Chemistry*, vol. 268, No. 4, pp. 2888-2892 (1993).
Narang, Saran A., "Tetrahedron Report No. 140 DNA Synthesis," *Tetrahedron*, vol. 39, No. 1, pp. 3-22 (1982).
Neda et al., "Chemical Modification of an Ecotropic Murine Leukemia Virus Results in Redirective of Its Target Cell Specificity," *J. Biol Chem*, vol. 266, pp. 14143-14146 (1991).
Nygren, Jan, et al., "The Interactions Between the Fluorescent Dye Thiazole Orange and DNA," *Biopolymers*, vol. 46, pp. 39-51 (1998).
Ochsner, U.A., et al. "Role of the ferric uptake regulator of Pseudomonas aeruginosa in the regulation of siderophores and exotoxin A expression: purification and activity on iron-regulated promoters," *Journal of Bacteriology*, vol. 177, No. 24, pp. 7194-7201 (1995).
Ozhalici-Unal et al., "A Rainbow of Fluoromodules: A Promiscuous scFv Protein Binds to and Activates a Diverse Set of Fluorogenic Cyanine Dyes," *J. Am. Chem. Soc.*, published online Aug. 30, 2008.
Pack et al., "Tetravalent Miniantibodies with High Avidity Assembling in *Escherichia coli*," *J Mol. Biol*, vol. 246(1), pp. 28-34 (1995).
Patterson, George H., "Use of the Green Fluorescent Protein and Its Mutants in Quantitative Fluorescence Microscopy," *Biophysical Journal*, vol. 73, pp. 2782-2790 (1997).
Perez, F., et al., "Antennapedia homeobox as a signal for the cellular internalization and nuclear addressing of a small exogenous peptide," *Journal of Cell Science*, vol. 102, pp. 717-722 (1992).
Pertz, Olivier and Klaus M. Hahn, "Designing biosensors for Rho family proteins—deciphering the dynamics of Rho family GTPase activation in living cells," *Journal of Cell Science*, vol. 117, pp. 1313-1318 (2004).
Pertz, Olivier, et al., "Spatiotemporal dynamics of RhoA activity in migrating cells," *Journal of Cell Science*, vol. 440, pp. 1069-1072 (2006).
Prince, R.W., et al., "Regulation of toxA and regA by the *Escherichia coli* fur gene and identification of a Fur homologue in *Pseudomonas aeruginosa* PA103 and PA01," *Molecular Microbiology*, vol. 5, pp. 2823-2831 (1991).
Post, Penny L., et al., "A Genetically Engineered, Protein-based Optical Biosensor of Myosin II Regulatory Light Chain Phosphorylation," *The Journal of Biological Chemistry*, vol. 269, No. 17, pp. 12880-12887 (1994).
Post, Penny L., et al., "A Fluorescent Protein Biosensor of Myosin II Regulatory Light Chain Phosphorylation Reports a Gradient of Phosphorylated Myosin II in Migrating Cells," *Molecular Biology of the Cell*, vol. 6, pp. 1755-1768 (1995).
Quantin et al., "Adenovirus as an expression vector in muscle cells in vivo," *Proc. Natl. Acad. Sci. USA*, vol. 89, pp. 2581-2584 (1992).
Ramjiawan, Bram, et al., "Noninvasive Localization of Tumors by Immunofluorescence Imaging Using a Single Chain Fv Fragment of a Human Monoclonal Antibody with Broad Cancer Specificity," *Cancer*, vol. 89, No. 5, pp. 1134-1344 (2000).
Roberts, Bruce L., et al., "Directed evolution of a protein: Selection of potent neutrophil elastase inhibitors displayed on M13 fusion phage," *Proc. Natl. Acad. Sci.*, vol. 89, pp. 2429-2433 (1992).
Rosenfeld, Melissa A., et al., "Adenovirus-Mediated Transfer of a Recombinant α1-Antitrypsin Gene to the Lung Epithelium in Vivo," *Science*, vol. 252, pp. 431-434 (1991).
Rosenfeld, Melissa A., et al., "In Vivo Transfer of the Human Cystic Fibrosis Transmembrane Conductance Regulator Gene to the Airway Epithelium," *Cell*, vol. 68, pp. 143-155 (1992).
Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA*, vol. 86, pp. 9079-9083 (1989).
Ruf, Wolfram, et al., "Mutational Mapping of Functional Residues in Tissue Factor: Identification of Factor VII Recognition Determi-

(56) References Cited

OTHER PUBLICATIONS nants in Both Structural Modules of the Predicted Cytokine Receptor Homology Domain," *Biochemistry*, vol. 33, pp. 1565-1572 (1993).

Sagawa, H. et al., "A tightly regulated expression system in *Escherichia coli* with SP6 RNA polymerase," *Gene*, vol. 168, pp. 37-41 (1996).

Sakata et al., "Optical switching of dipolar interactions on proteins," *Proc. Natl. Acad. Sci. USA*, vol. 102(13), pp. 4759-4764 (2005).

Schmitt, M.P. and S.M. Payne, "Genetic analysis of the enterobactin gene cluster in Shigella flexneri," *Journal of Bacteriology*, vol. 173, No. 2, pp. 816-824 (1991).

Scott, Jamie K. and George P. Smith, "Searching for Peptide Ligands with an Epitope Library," *Science*, vol. 249, pp. 386-390. (1990).

Senutovitch et al., "A Variable Light Domain Fluorogen Activating Protein Homodimerizes to Activate Dimethylindole Red," *Biochemistry*, Mar. 5, 2012, vol. 51, pp. 2471-2485.

Sharon et al., "Preparation of Fv Fragment from the Mouse Myeloma XRPC-25 Immunoglobulin Possessing Anti-Dinitrophenyl Activity," *Biochemistry*, vol. 15, No. 7, pp. 1591-1594 (1976).

Siegel, Robert W., et al., "High efficiency recovery and epitope-specific sorting of an scFv yeast display library," *Journal of Immunological Methods*, vol. 286, pp. 141-153 (2004).

Silva et al., "Experimental and Computational Investigation of Unsymmetrical Cyanine Dyes: Understanding Torsionally Responsive Fluorogenic Dyes," *J. Am. Chem. Soc.*, vol. 129, pp. 5710-5718 (2007).

Simeonov et al., "Blue-Flourescent Antibodies," *Science*, vol. 290, pp. 307-313 (Oct. 13, 2000).

Sims, P.J., et al. "Studies on the Mechanism by which Cyanine Dyes Measure Membrane Potential in Red Blood Cells and Phosphatidylcholine Vesicles," *Biochemistry*, vol. 13, pp. 3315-3330 (Jul. 30, 1974).

Skerra, "Engineered protein scaffolds for molecular recognition," *J. Mol. Recognition*, vol. 13, pp. 167-187 (2000).

Smith et al., "Molecular Engineering of the *Autographa californica* Nuclear Polyhedrosis Virus Genome: Deletion Mutations within the Polyhedrin Gene," *J. Virol*, vol. 46, pp. 584-593 (1983).

Studier, F. William, et al., "Use of T7 RNA Polymerase to Direct Expression of Cloned Genes," *Methods in Enzymology*, vol. 185, pp. 60-89, 1990.

Sumner, James P., et al., "A fluorescent PEBBLE nanosensor for intracellular free zinc," *The Analyst*, vol. 127, pp. 11-16 (2002).

Svinarich, David M. and Sunil Palchaudhuri, "Regulation of the SLT-1A Toxin Operon by a Ferric Uptake Regulatory Protein in Toxinogenic Strains of *Shigella dysenteria* type 1," *Journal of Diarrhoeal Disease Research*, vol. 10, pp. 139-145 (1992).

Swers et al., "Shuffled antibody libraries created by in vivo homologous recombination and yeast surface display," *Nucl. Acids Res.*, vol. 32 (3):e25, 8 pages (2004).

Szent-Gyorgyi et al., "Fluorogen-activating single-chain antibodies for imaging cell surface proteins," *Nature Biotechnology*, Dec. 23, 2007, vol. 26, No. 2, pp. 235-240.

Tacal, O., L. Ozer, "Adduct-Forming Tendencies of Cationic Triarylmethane Dyes with Proteins: Metabolic and Toxicological Implications," *J. Biochem. Mol. Toxicol.* vol. 18, pp. 253-256 (2004).

Takamatsu et al., "Expression of bacterial chloramphenicol acetyltransferase gene in tobacco paints mediated by TMV-RNA," *The EMBO Journal*, vol. 6(2), pp. 307-311 (1987).

Tanaka, T. et al., "Single Domain Intracellular Antibodies: A Minimal Fragment for Direct In Vivo Selection of Antigen-specific Intrabodies," *J. Mol. Biol.*, vol. 331, pp. 1106-1120 (Aug. 29, 2003).

Tempest, Philip R., et al., "Reshaping a Human Monoclonal Antibody to Inhibit human respiratory Syncytial Virus Infection In Vivo," *Biotechnology*, vol. 5, pp. 266-271 (1991).

Tirat, Aline, et al., "Evaluation of two novel tag-based labeling technologies for site-specific modification of proteins," *Int. J. Biol. Macromol.*, vol. 39, pp. 66-76 (2006).

Tratschin et al., "Adeno-Associated Virus Vector for High-Frequency Integration, Expression, and Rescue of Genes in Mammalian Cells," *Mol. Cell. Biol.*, vol. 5, pp. 3251-3260 (1985).

Tratschin et al., "A Human Parvovirus, Adeno-Associated Virus, as a Eucaryotic Vector: Transient Expression and Encapsidation of the Procaryotic Gene for Chlorampheicol Acetyltransferase," *Mol. Cell. Biol.*, vol. 4, pp. 2072-2081 (1984).

Tratschin et al., "Genetic Analysis of Adeno-Associated Virus: Properties of Deletion Mutants Constructed in Vitro and Evidence for an Adeno-Associated Virus Replication Function," *J. Virol.*, vol. 51, pp. 611-619 (1984).

Tsien, R.Y., "Building and breeding molecules to spy on cells and tumors," *FEBS Lett.*, vol. 579, pp. 927-932 (Feb. 7, 2005).

Valyukh I.V. et al., "Spectroscopic study of the fluorescent dyes interaction with DNA," *Functional Materials*, vol. 10, No. 3, pp. 528-533 (2003).

Van Beusechem et al., "Long-term expression of human adenosine deaminase in rhesus monkeys transplanted with retrovirus-infected bone-marrow cells," *Proc. Natl. Acad. Sci. USA*, vol. 89, pp. 7640-7644 (1992).

Viac, J., et al., An Immunoelectron Microscopic Localization of Wart Associated Antigens Present in Human Papilloma Virus (HPV) Infected Cells, *The Journal of Investigative Dermatology*, vol. 70, No. 5, pp. 263-266 (1978).

Wagner, Peter, et. al., "Covalent Immobilization of Native Biomolecules onto Au(111) via N-Hydroxysuccinimide Ester Functionalized Self-Assembled Monolayers for Scanning Probe Microscopy," *Biophysical Journal*, vol. 70, pp. 2052-2066 (1996).

Wagner et al., "Influenza virus hemagglutinin HA-2 N-terminal fusogenic peptides augment gene transfer by transferring-polylysine-DNA complexes: Toward a synthetic virus-like gene-transfer vehicle," *Proc. Natl. Acad. Sci USA*, vol. 89, pp. 7934-7938 (1992).

Ward et al., "Binding activities of a repertoire of single immunoglobulin variable domains secreted from *Escherichia coli*," *Nature*, vol. 341, pp. 544-546 (1989).

Wang, Su and Steven B. Vik, "Single Amino Acid Insertions Probe the a Subunit of the *Escherichia coli* $F_1 F_0$ -ATP Synthase," *The Journal of Biological Chemistry*, vol. 269, No. 4, pp. 3095-3099 (1993).

Wilson et al., "Retrovirus-mediated transduction of adult hepatocytes," *Proc. Natl. Acad. Sci. USA*, vol. 85, pp. 3014-3018 (1988).

Wiseman, Paul W., et al., "Spatial mapping of integrin interactions and dynamics during cell migration by Image Correlation Microscopy," *Journal of Cell Science*, vol. 117, pp. 5521-5534 (2004).

Yao, Jie, et al. "Dynamics of heat shock factor association with native gene loci in living cells," *Nature*, vol. 442, pp. 1050-1053 (2006).

Yeast Display scFv Antibody Library User's Manual (Pacific Northwest National Laboratory, Richland, WA99352), pp. 1-44 (2003).

Yoo et al. "Antibody-ligand interactions studied by fluorescence enhancement methods—I. Properties of the ligands 4-anilinoaphthalene-1-sulfonate and 6-anilinonaphthalene-2-sufonate." *Immunochemistry*, Pergamon Press, vol. 7, pp. 627-636 (1970).

Zhang et al., "Genetically enoded reporters of protein kinase A activity reveal impact of substrate tethering," *PNAS*, vol. 98, No. 26, pp. 14997-15002 (2001).

Humeau et al., How botulinim and tetanus neurotoxins block neurotansmitter release, Biochimie 2000 82(5):427-446.

Krebber et al., Reliable cloning of functional antibody variable domains from hybridomas and spleen cell repertoires employing a reengineered phage display system, J Immunol Methods 1997 201(1):35-55.

Schmidt and Bostian, Endoproteinase activity of type A botulinum neurotoxin: substrate requirements and activation by serum albumin, J Protein Chem 1997 16(1):19-26.

Schmidt and Bostian, Proteolysis of synthetic peptides by type A botulinum neurotoxin, J Protein Chem 1995 14(8):703-706.

Sikorra et al., Substrate recognition mechanism of VAMP/synaptobrevin-cleaving clostridial neurotoxins, J Biol Chem 2008 283(30):21145-52.

Vaidyanathan et al., Proteolysis of SNAP-25 isoforms by botulinum neurotoxin types A, C, and E: domains and amino acid residues

(56) References Cited

OTHER PUBLICATIONS controlling the formation of enzyme-substrate complexes and cleavage, J Neurochem 1999 72(1):327-337.
Washbourne et al., Botulinum neurotoxin types A and E require the SNARE notif in SNAP-25 for proteolysis, FEBS Letters 1997 418(1-2):1-5.

Written Opinon of the International Searching Authority dated May 31, 2013 for PCT/US2013/031988.

Anonymous, NEBcutter, 2016, Linear Sequence: SEQ ID NO48 part.

Non-final office action dated Nov. 3, 2016 in U.S. Appl. No. 14/774,362.

International Preliminary Report on Patentability and Written Opinion dated Jun. 29, 2009 for PCT/US2008/085415.

McLaughlin et al., "Adeno-Associated Virus General Transduction Vectors:Analysis of Proviral Structures." Journal of Virology, Jun. 1988, vol. 62, No. 6, 1963-1973.

Samulski et al., "Helper-Free Stocks of Recombinant Adeno-Associated Viruses:Normal Integration Does Not Require Viral Gene Expression." Journal of Virology, Sep. 1989, vol. 63, No. 9, 3822-3828.

* cited by examiner

```
5'- GTC TTC TCA GGA ATT CTA GGA TCT TTG GAA GTT TTG TTC CAA GGT CCA GGA GGT GGC GGT GGC AGC ...
3'- CAG AAG AGT CCT TAA GAT CCT AGA AAC CTT CAA AAC AAG GTT CCA GGT CCT AGG CCA CCG CCA CCG TCG ...
   - Val Ser Ser Gly Ile Leu Gly Ser Leu Glu Val Leu Phe Gln Gly Pro Gly Ser Gly Gly Gly Ser ...

... GGC GGT GGT GGA TCC GGC GGG GGT TCT AAT TTT ATG CTG - 3'
   ... CCG CCA CCA CCT AGG CCG CCC CCA AGA TTA AAA TAC GAC - 5'
   ... Gly Gly Gly Gly Ser Gly Gly Gly Gly Ser Gln Phe Met Leu -
```

LINKED PEPTIDE FLUOROGENIC BIOSENSORS

PRIORITY

This application is a continuation of U.S. patent application Ser. No. 12/745,882, now U.S. Pat. No. 8,426,153, which is a United States national stage application of and claims the benefit of International Application Number PCT/US2008/085415, filed Dec. 3, 2008, which claims the benefit of U.S. Provisional Patent Application Ser. No. 61/005,122, filed Dec. 3, 2007; the contents of each of which are incorporated by reference herein in their entirety.

GOVERNMENT SUPPORT

The invention claimed herein was made in part with support from the United States Government under National Institutes of Health (NIH) Grant Number 1U54-RR022241. The United States Government has certain rights in this invention.

TECHNICAL FIELD

The present disclosure is directed to biosensors, compositions comprising biosensors, methods of producing biosensors, and methods of using biosensors.

SEQUENCE LISTING

This application includes a Sequence Listing submitted via EFS-Web in computer readable form contained in a 73,283 byte file entitled 080750PCT_Revised_version ST25.txt created on Apr. 4, 2012, which is hereby incorporated herein by reference in its entirety.

BACKGROUND

The detection of target molecules and molecular components of larger structures is important in biological and biochemical sciences. The identification, analysis and monitoring of target biochemical or biological analytes, for example, is important for biomedical applications. Current diagnostics and assays employ a variety of methods to detect and analyze target molecules or molecular components ("analytes") in various environments, both in vitro and in vivo. Certain detection and analysis methods employ fluorescence phenomena. For example, immunoassays often employ antibodies labeled with fluorescent dye molecules (e.g., fluorescein derivatives) to target and detect certain analytes that specifically interact with the antibody. In these methods, a fluorescence signal produced by the fluorescent dye molecule attached to the antibody correlates with antibody-analyte interaction.

In other methods, a fluorescence signal may be altered by interaction between an analyte and a biosensor. Biosensor methods are capable of detecting the activity of analytes such as enzymes. For example, biosensors based on fluorogenic protease substrates comprising casein conjugates of two boron-dipyrromethene (BODIPY) dyes have been shown to be capable of detecting protease activity. This type of biosensor is disclosed in Jones et al., *Analytical Biochem.* 251, 144-152 (1997). In another example, biosensors based on fluorescence resonance energy transfer ("FRET") have been developed to detect kinase activity. A biosensor of this type includes a chimeric protein comprising a cyan fluorescent protein and a yellow fluorescent protein, which undergoes a conformational shift in response to phosphorylation. The conformational shift in the protein alters the orientation between the two fluorescent proteins and generates a FRET change. This type of biosensor is disclosed in Zhang et al., *Proc. Natl. Acad. Sci. USA* 98, 14997-15002, 2001.

SUMMARY

The present disclosure is directed in part to novel peptide constructs that find utility as biosensors in various applications.

Various embodiments disclosed herein are directed to linked peptide fluorogenic biosensors. The disclosed biosensors comprise a peptide construct comprising a fluorogen-activating peptide and a blocking peptide. The fluorogen-activating peptide is linked to the blocking peptide through a peptide linker comprising an amino acid sequence that is specifically recognized as a modification substrate by a cognate enzyme. The blocking peptide associates with the fluorogen-activating peptide thereby blocking the active domain of the fluorogen-activating peptide when the peptide linker is in an unmodified state. The fluorogen-activating peptide and the blocking peptide at least partially disassociate when the linker is modified by a cognate enzyme, thereby allowing the fluorogen-activating peptide to bind a cognate fluorogen and modulate the fluorescence signal produced by the fluorogen.

Various embodiments disclosed herein are also directed to methods for analyzing enzyme activity. The disclosed methods comprise contacting a medium comprising an analyte enzyme with a composition comprising a fluorogen and a biosensor construct as disclosed herein, and detecting a fluorescence signal produced by an interaction between the fluorogen-activating peptide of the biosensor construct and the fluorogen.

It should be understood that this disclosure is not limited to the embodiments disclosed in this Summary, and it is intended to cover modifications that are within the spirit and scope of the invention, as defined by the claims.

BRIEF DESCRIPTION OF THE DRAWINGS

The characteristics and advantages of the present disclosure may be better understood by reference to the accompanying figures, in which:

FIG. 11C depicts the nucleotide and amino acid sequences in a peptide linker region having an enzyme recognition sequence spliced therein. The portion of the amino acid sequence in the peptide linker region, as depicted in FIG. 11C, beginning with the second "Leu" and ending with "Pro" represents SEQ ID NO:9. The portion of the nucleotide sequence beginning with the first "TTG" and ending with "CCA" represents SEQ ID NO:10;

FIG. 12 presents semi-quantitative plots of cytometric data for a hybrid blocked single chain antibody having a protease recognition sequence spliced therein as illustrated in the accompanying diagram;

DETAILED DESCRIPTION

Figure 1A:
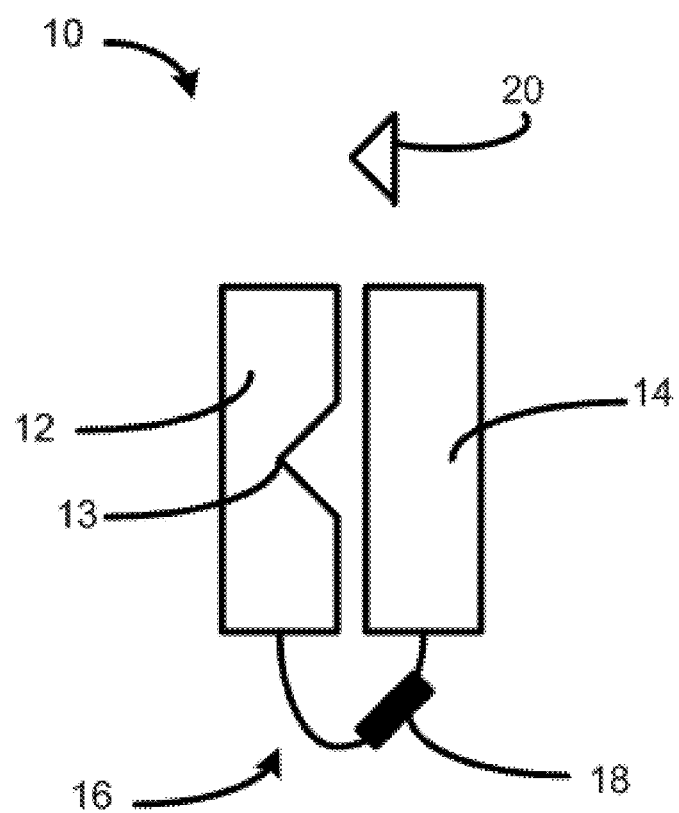
FIGS. 1A and 1B are diagrams illustrating the functionality of a biosensor construct according to various embodiments disclosed herein.

In the present application, including the claims, other than where otherwise indicated, all numbers expressing quantities, values or characteristics are to be understood as being modified in all instances by the term "about." Thus, numbers may be read as if preceded by the word "about" even though the term "about" may not expressly appear with the number. Accordingly, unless indicated to the contrary, any numerical parameters set forth in the following description may vary depending on the desired properties one seeks to obtain in the compositions and methods according to the present disclosure. At the very least, and not as an attempt to limit the application of the doctrine of equivalents to the scope of the claims, each numerical parameter described in the present description should at least be construed in light of the number of reported significant digits and by applying ordinary rounding techniques.

Any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The articles "a" and "an" are used herein to refer to one or to more than one (i.e., to at least one) of the grammatical object of the article. By way of example, "an element" means one element or more than one element.

As used herein, the term "amino acid" is intended to embrace all molecules, whether natural or synthetic, which include both an amino functionality and a carboxylate functionality and capable of being included in a poly(amino acid) polymer. Exemplary amino acids include, for example, naturally-occurring amino acids; analogs, derivatives and congeners thereof; amino acid analogs having variant side chains; and all stereoisomers of any of the foregoing.

As used herein, the terms "peptide," "polypeptide", and "protein" are synonymous and used interchangeably to refer to a polymer or oligomer of amino acids. In addition, as used herein, the terms "peptide," "polypeptide", and "protein" may refer to a discrete sub-unit of a larger peptide construct. As used herein, the term "peptide construct" refers to a peptide comprising discrete peptide domains covalently linked to form the larger peptide construct. The constituent peptides of a peptide construct may be covalently linked through peptide bonds. Any one or more constituent peptides of a peptide construct may also respectively possess an active domain that possesses various activity or functionality, including, but not limited to, receptor-ligand functionality, ligand-target functionality, enzyme-substrate functionality, and antibody-antigen functionality.

As used herein, the term "ligand" refers to a binding moiety for a specific target molecule. The molecule may comprise a cognate receptor, a protein, a small molecule, a hapten, an epitope, or any other relevant molecule. The molecule may comprise an analyte of interest. As used herein, the term "epitope" refers to a structure on a molecule that interacts with another molecule, such as, for example, an antibody or antibody fragment. In various embodiments, epitope refers to a desired region on a target molecule that specifically interacts with another molecule comprising a cognate ligand.

As used herein, "interact" and "interaction" are meant to include detectable interactions between molecules, such as may be detected using, for example, a hybridization assay. The terms "interact" and "interaction" also includes molecular associations including, but not limited to binding and complexation interactions between molecules. Interactions may be, for example, protein-protein, protein-nucleic acid, protein-small molecule or small molecule-nucleic acid, and include for example, antibody-antigen binding, enzyme-substrate binding, receptor-ligand binding, hybridization, and other forms of binding. In various embodiments, an interaction between a ligand and a specific target will lead to the formation of a complex, wherein the ligand and the target are unlikely to dissociate. Such affinity for a ligand and its target can be defined by the dissociation constant ($K_d$) as known in the art. A complex may include a ligand for a specific dye and is referred to herein as a "ligand-dye" complex.

As used herein, the term "antibody" refers to an immunoglobulin, derivatives thereof which maintain specific binding ability, and proteins having a binding domain which is homologous or largely homologous to an immunoglobulin binding domain. As such, an antibody operates as a ligand for its cognate antigen, which can be virtually any molecule. Natural IgG antibodies comprise two heavy chains and two light chains and are bi-valent. The interaction between the variable regions of heavy and light chain forms a binding site capable of specifically binding an antigen. The term "$V_H$" refers herein to a heavy chain variable region of an antibody. The term "$V_L$" refers herein to a light chain variable region of an antibody. Antibodies may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. In various embodiments, antibodies and antibody fragments used with the methods and compositions described herein are derivatives of the IgG class.

As used herein, the term "antibody fragment" refers to any derivative of an antibody which is less than full-length. In various embodiments, the antibody fragment retains at least a significant portion of the full-length antibody's specific binding ability. Examples of antibody fragments include, but are not limited to, Fab, Fab', F(ab)$_2$, Fv, dsFv, scFv, and Fd fragments. The antibody fragment may be produced by any means. For instance, the antibody fragment may be enzymatically or chemically produced by fragmentation of an intact antibody, or it may be recombinantly or partially synthetically produced using genetic engineering methods. An antibody fragment may comprise a single chain antibody fragment. Alternatively, an antibody fragment may comprise multiple chains which are linked together, for instance, by disulfide linkages. An antibody fragment may also comprise a multimolecular complex.

The term "Fab" refers herein to an antibody fragment that is essentially equivalent to that obtained by digestion of immunoglobulin (typically IgG) with the enzyme papain. The heavy chain segment of the Fab fragment is the Fd piece. Such fragments may be enzymatically or chemically produced by fragmentation of an intact antibody, recombinantly produced from a gene encoding the partial antibody sequence, or it may be wholly or partially synthetically produced. Methods for preparing Fab fragments are known in the art. See, for example, Tijssen, Practice and Theory of Enzyme Immunoassays (Elsevier, Amsterdam, 1985).

The term "F(ab')$_2$" refers herein to an antibody fragment that is essentially equivalent to a fragment obtained by digestion of an immunoglobulin (typically IgG) with the enzyme pepsin at pH 4.0-4.5. Such fragments may be enzymatically or chemically produced by fragmentation of an intact antibody, recombinantly produced from a gene encoding the partial antibody sequence, or it may be wholly or partially synthetically produced.

The term "Fab'" refers herein to an antibody fragment that is essentially equivalent to that obtained by reduction of the disulfide bridge or bridges joining the two heavy chain pieces in an F(ab')$_2$ fragment. Such fragments may be enzymatically or chemically produced by fragmentation of an intact antibody, recombinantly produced from a gene encoding the partial antibody sequence, or it may be wholly or partially synthetically produced.

The term "Fv" refers herein to an antibody fragment that consists of one $V_H$ and one $V_L$ domain held together by non-covalent interactions. The term "dsFv" is used herein to refer to an Fv with an engineered intermolecular disulfide bond to stabilize the $V_H$-$V_L$ pair. Methods for preparing Fv fragments are known in the art. See, for example, U.S. Pat. No. 4,462,334; Hochman et al., Biochemistry 12, 1130, 1973; Sharon et al., Biochemistry 15, 1591, 1976; and U.S. Pat. No. 4,355,023.

The terms "single chain antibody," "single-chain Fv," and "scFv" refer herein to an antibody fragment comprising the variable light chain ($V_L$) and variable heavy chain ($V_H$) antibody domains covalently connected to one another by a peptide linker moiety. Either the $V_L$ or the $V_H$ may be the amino-terminal domain. The peptide linker may be of variable length and composition. In various embodiments, peptide linkers may comprise segments of glycine and serine residues, optionally with some glutamic acid or lysine residues interspersed in the peptide linker sequence. Methods for preparing scFvs are known in the art. See, for example, International Application No. PCT/US/87/02208 and U.S. Pat. Nos. 4,704,692; 4,946,778, each of which is incorporated by reference herein in its entirety.

The term "single domain antibody" or "Fd" refers herein to an antibody fragment comprising a $V_H$ domain or a $V_L$ domain that interacts with a given antigen. A given Fd does not comprise both a $V_H$ domain and a $V_L$ domain. Methods for preparing single domain antibodies are known in the art. See, for example, Ward et al., Nature 341:644-646 (1989) and EP0368684.

As used herein, the term "fluorogen" refers to a chemical moiety that exhibits fluorogenic properties. Fluorogens include, but are not limited to, fluorogenic dyes, such as, for example, thiazole orange, malachite green, dimethyl indol red, and derivatives thereof. Not wishing to be bound by theory, the fluorogenic properties of dyes such as, for example, thiazole orange, malachite green, dimethyl indol red, and derivatives thereof are believed to be due to an environmentally sensitive conformational relaxation pathway (Magde et al., Chem. Phys. Letters 24, 144-148, 1974; Duxbury, Chem. Rev. 93, 381-433, 1993; Furstenberg et al., JACS 128, 7661-7669, 2006; Silvia et al., JACS 129, 5710-5718, 2007).

In solution, excitation of fluorogenic dyes with visible light may cause them to undergo rotation and/or torsion around one or more constituent intramolecular bonds. This may result in non-radiative decay of the exited state molecules back to the ground state. Therefore, fluorogenic dyes tend to exhibit very low fluorescence levels in solution. However, when a fluorogenic dye molecule is conformationally constrained, such as, for example, in the active domain of a cognate protein or peptide, the rotational and/or torsional molecular motion induced by visible excitation may be inhibited. As a result, the excitation energy may be given off radiatively when a fluorogenic dye relaxes to the ground state energy level while interacting with a cognate moiety. Examples of fluorogens that find utility in the embodiments disclosed herein are described in International Application Nos. PCT/US2003/029289 and PCT/US2008/051962; and U.S. Application No. 60/418,834; Ser. Nos. 11/077,999; 60/897,120; and 61/013,098, each of which is incorporated by reference herein in its entirety.

As used herein, in reference to fluorescence, the terms "modulate" and "modulation" refer to a change in fluorescence signal intensity, fluorescence lifetime, fluorescence wavelength, or any other measurable property of a fluorescing moiety.

The term "sequence homology" refers to the proportion of base matches between two nucleic acid sequences or the proportion of amino acid matches between two amino acid sequences. When sequence homology is expressed as a percentage, e.g., 50%, the percentage denotes the proportion of matches over the length of sequence from a desired sequence (e.g., SEQ. ID NO: 1) that is compared to some other sequence. Gaps (in either of the two sequences) are permitted to maximize matching; gap lengths of 15 bases or less are usually used, 6 bases or less are used more frequently, with 2 bases or less used even more frequently. The term "sequence identity" means that sequences are identical (i.e., on a nucleotide-by-nucleotide basis for nucleic acids or amino acid-by-amino acid basis for polypeptides) over a window of comparison. The term "percentage of sequence identity" is calculated by comparing two optimally aligned sequences over the comparison window, determining the number of positions at which the identical amino acids occur in both sequences to yield the number of matched positions, dividing the number of matched positions by the total number of positions in the comparison window, and multiplying the result by 100 to yield the percentage of sequence identity. Methods to calculate sequence identity are known to those of skill in the art.

A selectivity component may be any molecule which is capable of selectively interacting with a desired target molecule, including an antibody or antibody fragment. For example, selectivity components may be monoclonal antibodies, or derivatives or analogs thereof, including without limitation: Fv fragments and single chain Fv (scFv) fragments. In certain embodiments, a biosensor may comprise a selectivity component having at least about 85% sequence identity with a sequence within SEQ ID NO:21 through 40. In certain other embodiments, an isolated, purified biosensor may comprise a selectivity component having at least about 85% sequence identity with a sequence within SEQ ID NO:21 through 40. In certain embodiments, a vector may comprise a nucleic acid sequence having at least about 85% sequence identity to a polynucleotide encoding a protein with the appropriate sequence corresponding to SEQ ID NO:21 through 40. In certain other embodiments, a vector may comprise a nucleic acid sequence having at least about 95% sequence identity to a polynucleotide encoding a protein with the appropriate sequence corresponding to SEQ ID NO:21 through 40.

Various embodiments disclosed herein are directed to linked peptide fluorogenic biosensors. The disclosed biosensors comprise a peptide construct. The peptide construct may comprise a fluorogen-activating peptide and a blocking peptide. The fluorogen-activating peptide comprises an active domain that specifically interacts with a fluorogen to modulate the fluorescence signal produced by the fluorogen. The fluorogen-activating peptide is linked to the blocking peptide through a peptide linker.

The peptide linker may comprise an amino acid sequence that is specifically recognized as a modification substrate by a cognate enzyme. The blocking peptide may specifically associate with the fluorogen-activating peptide, thereby blocking the active domain of the fluorogen-activating peptide, when the peptide linker is in an unmodified state. The fluorogen-activating peptide and the blocking peptide may at least partially disassociate when the peptide linker is modified by a cognate enzyme, thereby allowing the fluorogen-activating peptide to interact with a cognate fluorogen and modulate a fluorescence signal.

In various embodiments, the present disclosure is directed to biosensors comprising a fluorogen-activating peptide comprising a variable domain of an antibody, and a blocking peptide comprising a variable domain of an antibody. One of the fluorogen-activating peptide and the blocking peptide may comprise a variable heavy chain domain of an antibody and the other peptide may comprise a variable light chain domain of a different antibody. The fluorogen-activating peptide may comprise a single domain antibody. The blocking peptide may be linked to the fluorogen-activating peptide through a peptide linker comprising an amino acid sequence that is specifically recognized as a cleavage substrate by a cognate protease. The blocking peptide may associate with the fluorogen-activating peptide thereby blocking the active domain of the fluorogen-activating peptide when the linker is intact. The fluorogen-activating peptide and the blocking peptide may at least partially disassociate when the linker is cleaved by a cognate protease, thereby allowing the fluorogen-activating peptide to interact with a cognate fluorogen and modulate a fluorescence signal.

In various embodiments, the present disclosure is directed to biosensors comprising a fluorogen-activating peptide comprising a variable domain of an antibody, a blocking peptide comprising a variable domain of an antibody, and a phospho(amino acid) binding peptide linked to the fluorogen-activating peptide or the blocking peptide. One of the fluorogen-activating peptide and the blocking peptide may comprise a variable heavy chain domain of an antibody and the other peptide may comprise a variable light chain domain of a different antibody. The fluorogen-activating peptide may comprise a single domain antibody. The blocking peptide may be linked to the fluorogen-activating peptide through a peptide linker comprising an amino acid sequence that may be specifically recognized as a phosphorylation substrate by a cognate protein kinase. The blocking peptide may associate with the fluorogen-activating peptide thereby blocking the active domain of the fluorogen-activating peptide when the peptide linker is not phosphorylated. The fluorogen-activating peptide and the blocking peptide may at least partially disassociate when the peptide linker is phosphorylated by a cognate protein kinase, thereby allowing the fluorogen-activating peptide to interact with a cognate fluorogen and produce a fluorescence signal.

In various embodiments, the present disclosure is directed to biosensors comprising a fluorogen-activating peptide comprising a variable domain of an antibody, a blocking peptide comprising a variable domain of an antibody, and a bromo-domain peptide that is linked to the fluorogen-activating peptide or the blocking peptide. One of the fluorogen-activating peptide and the blocking peptide may comprise a variable heavy chain domain of an antibody and the other peptide may comprise a variable light chain domain of a different antibody. The fluorogen-activating peptide may comprise a single domain antibody. The blocking peptide may be linked to the fluorogen-activating peptide through a peptide linker comprising an amino acid sequence that may be specifically recognized as an acetylation substrate by a cognate acetyltransferase. The blocking peptide may associate with the fluorogen-activating peptide thereby blocking the active domain of the fluorogen-activating peptide when the peptide linker is not acetylated. The fluorogen-activating peptide and the blocking peptide may at least partially disassociate when the peptide linker is acetylated by a cognate acetyltransferase, thereby allowing the fluorogen-activating peptide to interact with a cognate fluorogen and produce a fluorescence signal.

In various embodiments, the present disclosure is directed to a composition comprising a fluorogen and a biosensor as disclosed herein. Fluorogens finding utility in the compositions disclosed herein include, but are not limited to, thiazole orange, malachite green, dimethyl indole red, and derivatives thereof. In various embodiments, the present disclosure is directed to methods for analyzing enzyme activity. The disclosed methods may comprise contacting a medium comprising an analyte enzyme with a composition comprising a fluorogen and a biosensor as disclosed herein, and detecting a fluorescence signal produced by an interaction between a fluorogen-activating peptide of the biosensor construct and the fluorogen.

Figure 1B:
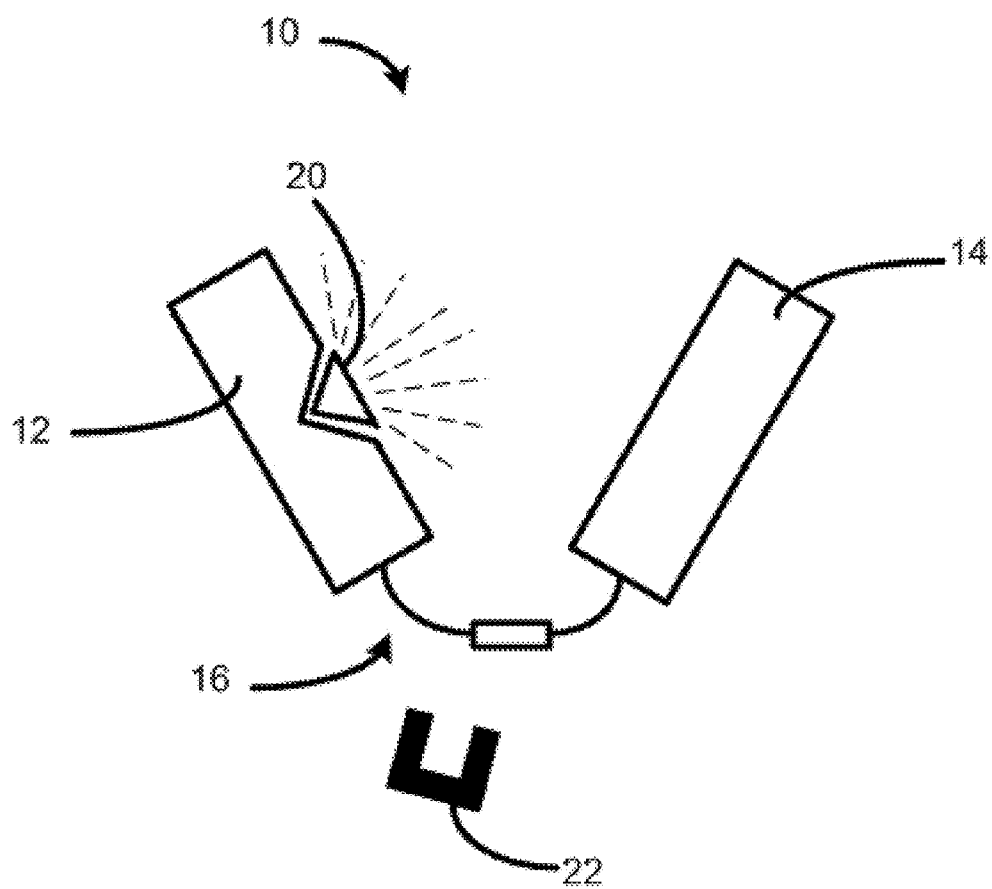

FIGS. 1A and 1B illustrate a biosensor according to various embodiments disclosed herein. Biosensor 10 comprises a fluorogen-activating peptide 12 having an active domain 13 that is capable of specifically interacting with a cognate fluorogen 20 to modulate a fluorescence signal produced by the fluorogen. The fluorogen-activating peptide 12 is linked to a blocking peptide 14 through a peptide linker 16. The peptide linker 16 comprises an amino acid sequence 18 that is specifically recognized as a modification substrate by a cognate enzyme 22. As illustrated in FIG. 1A, the blocking peptide 14 associates with the fluorogen-activating peptide 12 thereby blocking the active domain 13 of the fluorogen-activating peptide 12 when the peptide linker 16 is in an unmodified state. As illustrated in FIG. 1B, the fluorogen-activating peptide 12 and the blocking peptide 14 at least partially disassociate when the linker 16 is modified by a cognate enzyme 22, thereby allowing the fluorogen-activating peptide 12 to interact with the cognate fluorogen 20 and modulate a fluorescence signal.

In various embodiments, the peptide linker may be a synthetic flexible chain of from 15 amino acids in length to 30 amino acids in length. The peptide linker may comprise relatively small amino acid residues, including, but not limited to, glycine. Small amino acid residues may reduce the steric bulk and increase the flexibility of the peptide linker. The peptide linker may also comprise polar amino acids, including, but not limited to, serine. Polar amino acid residues may increase the aqueous solubility of the peptide linker. In various embodiments, the peptide linker may comprise an amino acid sequence comprising $(Gly_4Ser)_3$ (SEQ ID NO:1), and an amino acid sequence that is specifically recognized as a modification substrate by a cognate enzyme. In various embodiments, the peptide linker may comprise a site-specific modification amino acid sequence located on the N-terminal end of a $(Gly_4Ser)_3$ sequence; and in various embodiments the peptide linker may comprise a site-specific modification amino acid sequence located on the C-terminal end of a $(Gly_4Ser)_3$ sequence.

In various embodiments, the disclosed biosensors may comprise a peptide linker that comprises a site-specific protease recognition amino acid sequence (i.e., an amino acid sequence that is specifically recognized as a proteolysis substrate by a cognate protease). As used herein, the term "protease" refers to an enzyme involved in proteolysis, that is, catabolic hydrolysis of peptide bonds that link amino acids together in peptide chains. A peptide linker comprising a site-specific protease recognition amino acid sequence as a modification substrate may be cleaved by a cognate protease.

Figure 2A:
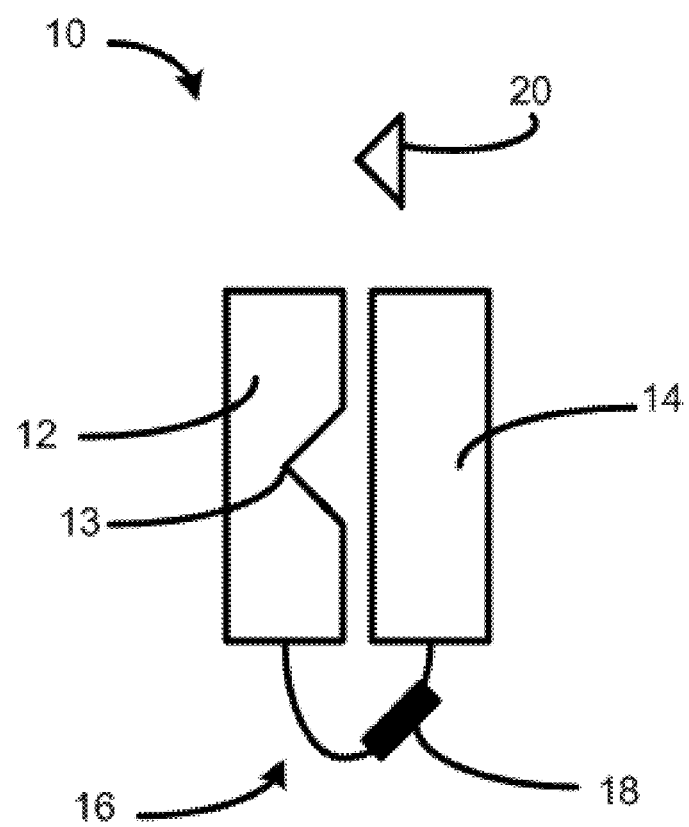
FIGS. 2A and 2B are diagrams illustrating the functionality of a biosensor construct according to various embodiments disclosed herein.
Figure 2B:
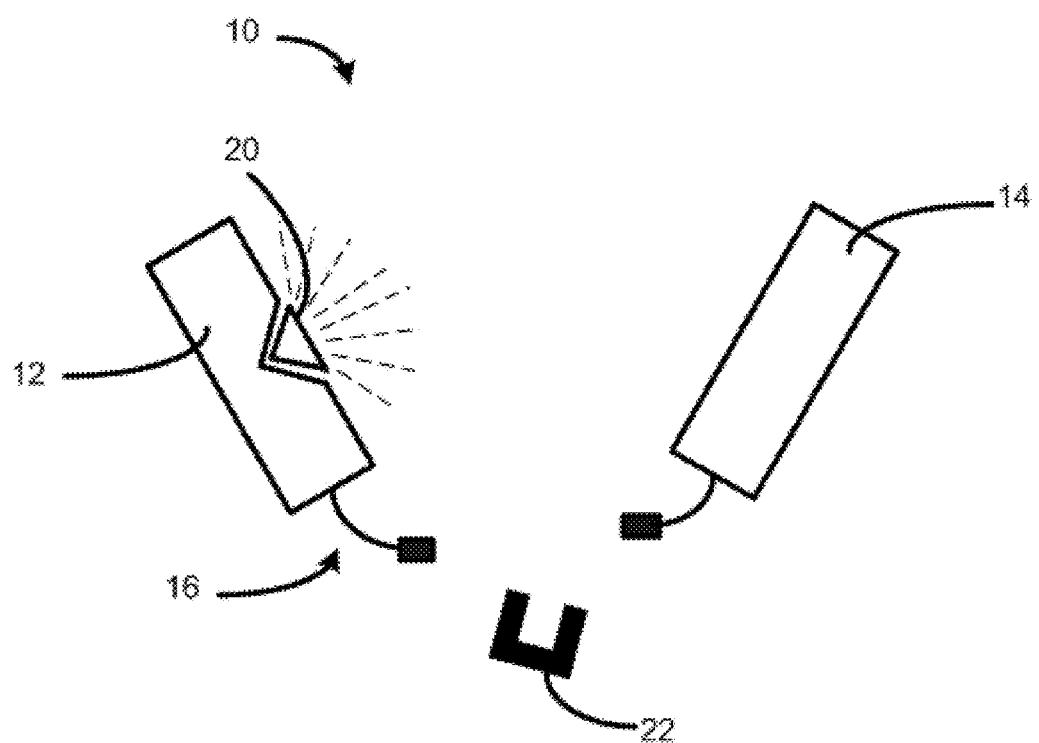

In various embodiments disclosed herein, when a protease recognizes a site-specific amino acid sequence contained in a peptide linker, the peptide linker may be cleaved, thereby breaking the covalent linkage between the fluorogen-activating peptide and the blocking peptide. The fluorogen-activating peptide and the blocking peptide may then at least partially dissociate or completely dissociate and diffuse away from each other. Not wishing to be bound by theory, the at least partial dissociation may be driven at least in part by an increase in translational entropy. When the fluorogen-activating peptide is at least partially disassociated from the blocking peptide, the active domain of the fluorogen-activating peptide may become un-blocked, and therefore, may become free to interact with a cognate fluorogen and modulate a fluorescence signal produced by the fluorogen. FIGS. 2A and 2B illustrate a biosensor according to this embodiment.

In various embodiments, the peptide linker may comprise a site-specific protease recognition amino acid sequence specifically recognized as a cleavage site by a protease selected from the group consisting of a serine protease, a threonine protease, a cysteine protease, an aspartic acid protease, a matrix metalloproteinase, and a glutamic acid protease. In various embodiments, the peptide linker may comprise a site-specific protease recognition amino acid sequence specifically recognized as a cleavage substrate by a protease selected from the group consisting of furan protease, tobacco etch virus ("TEV") protease, a 3C protease, a caspase, and a matrix metalloproteinase, for example.

In various embodiments, the disclosed peptide linker may comprise an amino acid sequence specifically recognized as a cleavage site by furin. Furin is a protease that is involved in a protein secretory pathway in eukaryotic cells. In mammalian cells, for example, furin is localized to the protein secretory pathway between the trans-Golgi network and the cell surface. A consensus recognition sequence for furin protease has been reported as Arg-Xaa-(Lys/Arg)-Arg-Ser (SEQ ID NO:64). By way of example, furin protease may specifically recognize a short recognition sequence (e.g., Arg-Lys-Lys-Arg-Ser) or a long recognition sequence (e.g., Asn-Ser-Arg-Lys-Lys-Arg-Ser-Thr-Ser-Ala). In various embodiments, the disclosed peptide linker may comprise an amino acid sequence comprising Arg-Xaa-(Lys/Arg)-Arg-Ser. In various embodiments, the disclosed peptide linker may comprise an amino acid sequence comprising Arg-Lys-Lys-Arg-Ser (SEQ ID NO:3). In various embodiments, the disclosed peptide linker may comprise an amino acid sequence comprising Asn-Ser-Arg-Lys-Lys-Arg-Ser-Thr-Ser-Ala (SEQ ID NO:5).

In various embodiments, the disclosed peptide linker may comprise an amino acid sequence specifically recognized as a cleavage site by TEV protease. TEV protease is a site-specific cysteine protease that is found in the tobacco etch virus. TEV protease is used, for example, to remove affinity tags from purified proteins. A consensus recognition sequence for TEV protease has been reported as Glu-Asn-Leu-Tyr-Phe-Gln-Gly, with cleavage occurring between the Gln and Gly residues. In various embodiments, the disclosed peptide linker may comprise an amino acid sequence comprising Glu-Asn-Leu-Tyr-Phe-Gln-Gly (SEQ ID NO:7).

In various embodiments, the disclosed peptide linker may comprise an amino acid sequence specifically recognized as a cleavage site by a 3C protease. 3C proteases are viral enzymes that cleave viral precursor polyproteins to form functional proteins, and are thought to be involved in viral replication. A consensus recognition sequence for human rhinovirus 3C ("HRV-3C") protease, for example, has been reported as Leu-Glu-Val-Leu-Phe-Gln-Gly-Pro, with cleavage occurring between the Gln and Gly residues. In various embodiments, the disclosed peptide linker may comprise an amino acid sequence comprising Leu-Glu-Val-Leu-Phe-Gln-Gly-Pro (SEQ ID NO:9).

In various embodiments, the disclosed peptide linker may comprise an amino acid sequence specifically recognized as a cleavage site by a caspase. Caspases (cysteine-aspartic acid proteases) are a family of cysteine proteases thought to be involved in apoptosis, necrosis and inflammation, for example. Eleven caspases have been identified in humans. A consensus recognition sequence for caspase 1, for example, has been reported as Tyr-Val-Ala-Asp. A consensus recognition sequence for caspase 3, for example, has been reported as Asp-Glu-Val-Asp. In various embodiments, the disclosed peptide linker may comprise an amino acid sequence comprising the sequence Tyr-Val-Ala-Asp (SEQ ID NO:11). In various embodiments, the disclosed peptide linker may comprise an amino acid sequence comprising the sequence Asp-Glu-Val-Asp (SEQ ID NO:13).

In various embodiments, the disclosed peptide linker may comprise an amino acid sequence specifically recognized as a cleavage site by a matrix metalloproteinase. Matrix metalloproteinases ("MMPs") are zinc-dependent proteases capable of cleaving a number of extracellular matrix proteins and cell surface receptors, for example. MMPs are thought to be involved in the release of apoptotic ligands and chemokine activation/inactivation. MMPs are also thought to be involved in cell proliferation, migration (adhesion/dispersion), differentiation, angiogenesis, and host defense, for example. A number of MMPs have been identified. A consensus recognition sequence for MMP25, for example, has been reported as Val-Met-Arg-Leu-Val-Val. In various embodiments, the disclosed peptide linker may comprise an amino acid sequence comprising Val-Met-Arg-Leu-Val-Val (SEQ ID NO:15).

In various embodiments, the disclosed biosensors may comprise a peptide linker comprising a site-specific kinase recognition amino acid sequence (i.e., an amino acid sequence that is specifically recognized as a phosphorylation substrate by a cognate protein kinase). As used herein, the term "kinase" refers to an enzyme involved in phosphorylation, that is, enzymatic transfer of phosphate groups from donor molecules (e.g., ATP) to specific target substrates. As used herein, the terms "kinase" and "phosphotransferase" are synonymous. As used herein, the term "protein kinase" refers to a kinase that recognizes a site-specific amino acid sequence and phosphorylates a peptide comprising such a recognition sequence. A peptide linker comprising a site-specific kinase recognition amino acid sequence as a modification substrate may be phosphorylated by a cognate kinase.

In various embodiments disclosed herein, when a kinase recognizes a site-specific amino acid sequence contained in a peptide linker, the peptide linker may be phosphorylated, thereby modifying the linkage between the fluorogen-activating peptide and the blocking peptide. The modification of the linker may change the chemical and physical conditions within the microenvironment surrounding the peptide linker. As used herein, the term "microenvironment" refers to localized conditions within a larger area. For example, modification of a peptide sequence may alter the local chemical and/or physical conditions surrounding the peptide sequence, which may result in a conformational change in the intramolecular secondary or tertiary structure of a peptide construct comprising the peptide sequence. In this regard, the microenvironment surrounding the peptide sequence may be changed when the peptide sequence is modified.

A conformational change in a peptide construct according to the disclosed embodiments may result in at least partial dissociation between a fluorogen-activating peptide and a blocking peptide. Not wishing to be bound by theory, the at least partial dissociation may be driven at least in part by a change in the chemical and/or physical conditions in the microenvironment surrounding the phosphorylated peptide linker. When the fluorogen-activating peptide is at least partially disassociated from the blocking peptide, the active domain of the fluorogen-activating peptide may become un-blocked, and therefore, may become free to interact with a cognate fluorogen and modulate a fluorescence signal. Referring to FIGS. 1A and 1B, enzyme 22 may be a kinase that recognizes amino acid sequence 18 and phosphorylates peptide linker 16. As a result, the change in the microenvironment surrounding the peptide linker 16 may induce at least partial dissociation between the fluorogen-activating peptide 12 and the blocking peptide 14.

In various embodiments, the disclosed peptide linker may comprise an amino acid sequence specifically recognized as a phosphorylation substrate by protein kinase A ("PKA"). PKA is a cAMP-dependent kinase involved in numerous parallel signaling networks and pathways. A consensus recognition sequence for PKA, for example, has been reported as Leu-Arg-Arg-Ala-Ser-Leu-Gly (SEQ ID NO:59) (also known as PKA kemptide phosphorylation sequence). Various modified PKA kemptide phosphorylation sequences are also known to be specifically-recognized by PKA, for example, the amino acid sequences Leu-Arg-Arg-Ala-Ser-Leu-Pro (SEQ ID NO:60) and Leu-Leu-Arg-Arg-Ala-Ser-Leu-Gly-Pro (SEQ ID NO:17). In various embodiments, the disclosed peptide linker may comprise an amino acid sequence comprising a Leu-Arg-Arg-Ala-Ser-Leu-Gly sequence; a Leu-Arg-Arg-Ala-Ser-Leu-Pro sequence; or a Leu-Leu-Arg-Arg-Ala-Ser-Leu-Gly-Pro sequence.

In various embodiments, a biosensor comprising a peptide linker comprising a site-specific kinase recognition amino acid sequence may further comprise a phospho(amino acid) binding peptide linked to the fluorogen-activating peptide or the blocking peptide. As used herein, the term "phospho (amino acid) binding peptide" refers to a peptide comprising a domain that specifically interacts with another peptide comprising a phosphorylated amino acid. For example, a phospho(amino acid) binding peptide may preferentially complex with a peptide comprising a phosphorylated amino acid. A peptide construct comprising a fluorogen-activating peptide and a blocking peptide connected through a peptide linker comprising a site-specific kinase recognition amino acid sequence, and a phospho(amino acid) binding peptide linked to the fluorogen-activating peptide or the blocking peptide, may exhibit a conformational change when the peptide linker is phosphorylated by a kinase. Not wishing to be bound by theory, the intramolecular interaction between the phosphorylated peptide linker and the phospho(amino acid) binding peptide may substantially change the orientation of the peptide construct such that the fluorogen-activating peptide and the blocking peptide at least partially disassociate.

Figure 3A:
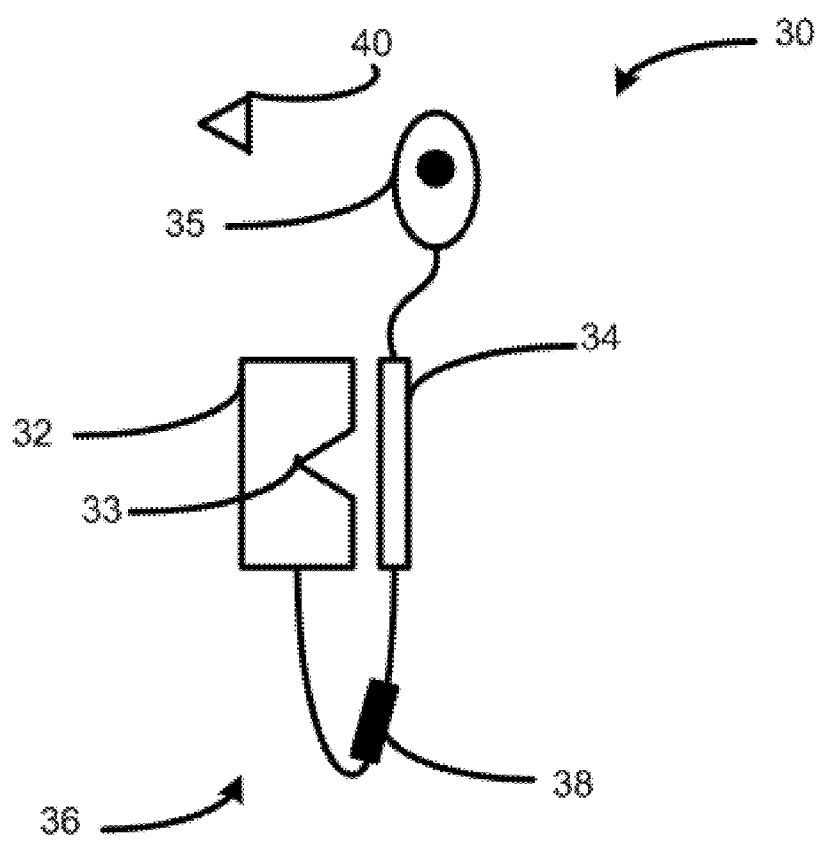
FIGS. 3A and 3B are diagrams illustrating the functionality of a biosensor construct according to various embodiments disclosed herein.
Figure 3B:
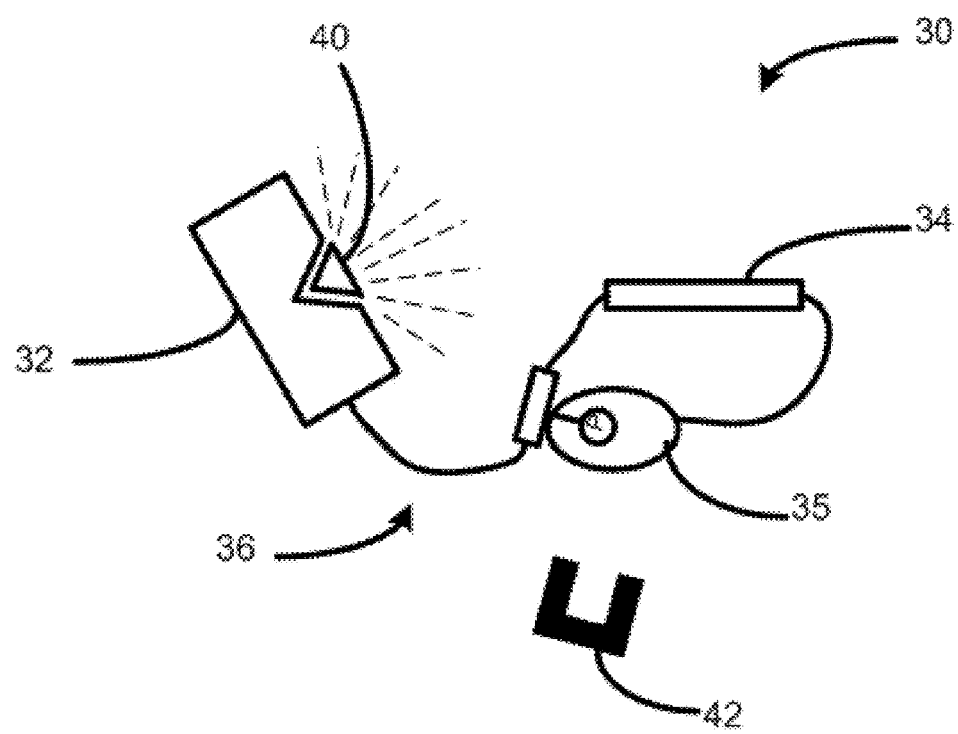

FIGS. 3A and 3B illustrate a biosensor according to the embodiments disclosed herein. Biosensor 30 comprises a fluorogen-activating peptide 32 having an active domain 33 that is capable of specifically interacting with a cognate fluorogen 40 to modulate a fluorescence signal produced by the fluorogen. The fluorogen-activating peptide 32 is linked to a blocking peptide 34 through a peptide linker 36. The peptide linker 36 comprises a site-specific kinase recognition amino acid sequence 38 that is specifically recognized by a cognate kinase 42. As illustrated in FIG. 3A, the blocking peptide 34 associates with the fluorogen-activating peptide 32 thereby blocking the active domain 33 of the fluorogen-activating peptide 32 when the peptide linker 36 is not phosphorylated.

As illustrated in FIG. 3B, when kinase 42 phosphorylates peptide linker 36, the peptide linker 36 interacts with a phospho(amino acid) binding peptide 35. This interaction induces a conformational change in the peptide construct resulting in at least partial dissociation between the fluorogen-activating peptide 32 and the blocking peptide 34, thereby allowing the fluorogen-activating peptide 32 to interact with the cognate fluorogen 40 and modulate a fluorescence signal.

In various embodiments, the disclosed biosensors may comprise a peptide construct comprising a phospho(amino acid) binding peptide, a fluorogen-activating peptide, a peptide linker comprising a site-specific kinase recognition amino acid sequence, and a blocking peptide. In various embodiments, the phospho(amino acid) binding peptide is linked to the fluorogen-activating peptide. In various embodiments, the phospho(amino acid) binding peptide is linked to the blocking peptide. In various embodiments, the phospho(amino acid) binding peptide comprises 14-3-3τ protein. 14-3-3τ protein is a phospho-serine binding protein which recognizes and interacts with phosphorylated serine amino acid residues in peptides (Zhang et al., *Proc. Natl. Acad. Sci. USA* 98, 14997-15002, 2001, which is incorporated by reference herein in its entirety).

In various embodiments, the disclosed biosensors comprise a peptide linker that comprises a site-specific acetyltransferase recognition amino acid sequence (i.e., an amino acid sequence that is specifically recognized as an acetylation substrate by a cognate acetyltransferase). As used herein, the term "acetyltransferase" refers to an enzyme involved in acetylation, that is, enzymatic transfer of acetyl groups from donor molecules (e.g., acetyl CoA) to specific target substrates. As used herein, the term "acetyltransferase" also refers to an enzyme that recognizes a site-specific amino acid sequence and acetylates a peptide comprising such a recognition sequence. A peptide linker comprising a site-specific acetyltransferase recognition amino acid sequence as a modification substrate may be acetylated by a cognate acetyltransferase.

In various embodiments disclosed herein, when an acetyltransferase recognizes a site-specific amino acid sequence contained in a peptide linker, the peptide linker may be acetylated, thereby modifying the linkage between the fluorogen-activating peptide and the blocking peptide. The modification of the linker may change the chemical and physical conditions within the microenvironment surrounding the peptide linker. The acetylation of a peptide sequence may alter the local chemical and/or physical conditions surrounding the peptide sequence, which may result in a conformational change in the intramolecular secondary or tertiary structure of a peptide construct comprising a peptide sequence. In this regard, the microenvironment surrounding a peptide sequence may be changed when the peptide sequence is acetylated.

A conformational change in a peptide construct according to the disclosed embodiments may result in at least partial dissociation between the fluorogen-activating peptide and the blocking peptide. Not wishing to be bound by theory, the at least partial dissociation may be driven at least in part by a change in the chemical and/or physical conditions in the microenvironment surrounding the acetylated peptide linker. When the fluorogen-activating peptide is at least partially disassociated from the blocking peptide, the active domain of the fluorogen-activating peptide may become un-blocked, and therefore, may become free to interact with a cognate fluorogen and modulate a fluorescence signal. Referring to FIGS. 1A and 1B, enzyme 22 may be an acetyltransferase that recognizes amino acid sequence 18 and acetylates peptide linker 16. As a result, the change in the microenvironment surrounding the peptide linker 16 induces at least partial dissociation between the fluorogen-activating peptide 12 and the blocking peptide 14.

In various embodiments, the disclosed peptide linker may comprise an amino acid sequence specifically recognized as an acetylation substrate by a histone acetyltransferase ("HAT"). For example, acetylation of histone H3 lysine 56 ("H3-K56") is reported to be mediated by HATs that recognize the amino acid sequence Ile-Arg-Arg-Phe-Gln-Lys-Ser-Thr-Asp-Leu-Leu. In various embodiments, the disclosed peptide linker may comprise an amino acid sequence comprising Ile-Arg-Arg-Phe-Gln-Lys-Ser-Thr-Asp-Leu-Leu (SEQ ID NO:19).

In various embodiments, a biosensor comprising a peptide linker comprising a site-specific acetyltransferase recognition amino acid sequence may further comprise an acetyl (amino acid) binding peptide linked to the fluorogen-activating peptide or the blocking peptide. As used herein, the term "acetyl(amino acid) binding peptide" refers to a peptide comprising a domain that specifically interacts with a peptide comprising an acetylated amino acid. For example, an acetyl(amino acid) binding peptide may preferentially complex with a peptide comprising an acetylated amino acid. A peptide construct comprising a fluorogen-activating peptide and a blocking peptide connected through a peptide linker comprising a site-specific acetyltransferase recognition amino acid sequence, and an acetyl(amino acid) binding peptide linked to either the fluorogen-activating peptide or the blocking peptide, may exhibit a conformational change when the peptide linker is acetylated by an acetyltransferase. Not wishing to be bound by theory, the intramolecular interaction between the acetylated peptide linker and the acetyl(amino acid) binding peptide may substantially change the orientation of the peptide construct such that the fluorogen-activating peptide and the blocking peptide at least partially disassociate.

A biosensor according to this embodiment may function analogously to the biosensors illustrated in FIGS. 3A and 3B comprising a peptide linker comprising a site-specific kinase recognition amino acid sequence and a phospho(amino acid) binding peptide. In this embodiment, the interaction would occur between a site-specific acetyltransferase recognition amino acid sequence and an acetyl(amino acid) binding peptide. This interaction may induce a conformational change in the peptide construct resulting in at least partial dissociation between the fluorogen-activating peptide and the blocking peptide, thereby allowing the fluorogen-activating peptide to interact with the cognate fluorogen and modulate a fluorescence signal.

In various embodiments, the disclosed biosensors may comprise a peptide construct comprising an acetyl(amino acid) binding peptide, a fluorogen-activating peptide, a peptide linker comprising a site-specific acetyltransferase recognition amino acid sequence, and a blocking peptide. In various embodiments, the acetyl(amino acid) binding peptide is linked to the fluorogen-activating peptide. In various embodiments, the acetyl(amino acid) binding peptide is linked to the blocking peptide. In various embodiments, the acetyl(amino acid) binding peptide comprises a bromo-domain protein. Bromo-domain proteins are acetyl-lysine binding proteins which recognize and interact with acetylated lysine amino acid residues in peptides (Mujtaba et al,

*Oncogene* 26, 5521-5527, 2007, which is incorporated by reference herein in its entirety).

Figure 4:
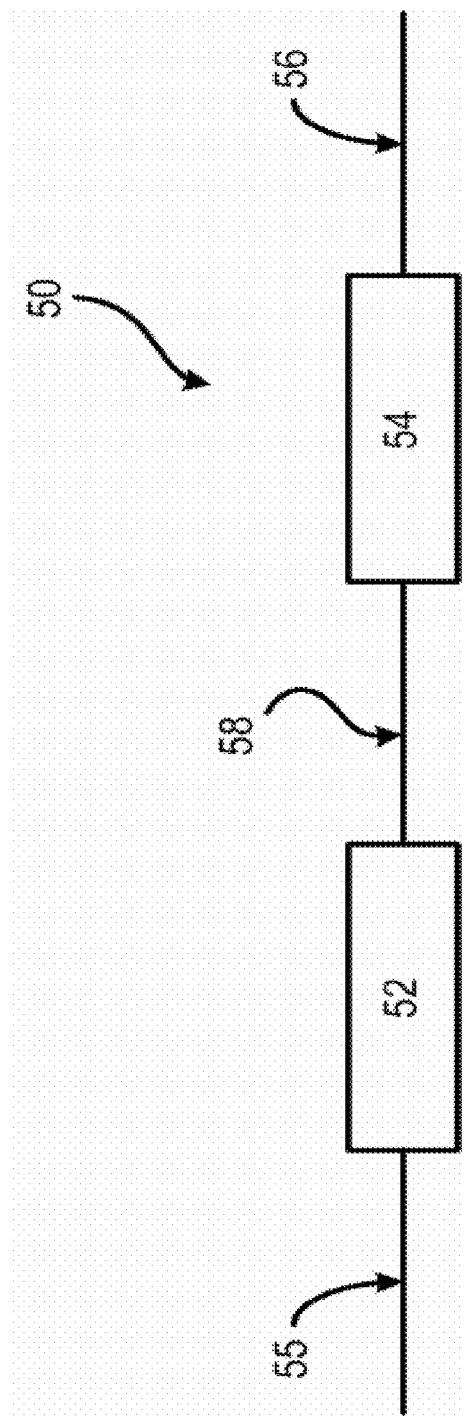
FIG. 4 is a diagram illustrating the structure of peptide constructs according to various embodiments disclosed herein.

In various embodiments, the disclosed biosensors may comprise a peptide construct having a linear peptide structure as illustrated in FIG. 4. Peptide construct 50 may comprise peptide regions 52, 54, 55, 56 and 58. Peptide region 52 may comprise a fluorogen-activating peptide and peptide region 54 may comprise a blocking peptide. Peptide regions 52 and 54 are linked by a peptide region 58, which may comprise a peptide linker. In various embodiments, peptide region 58 may comprise a site-specific kinase recognition amino acid sequence or a site-specific acetyltransferase recognition amino acid sequence, and either peptide region 55 or peptide region 56 may comprise a phospho (amino acid) binding peptide or an acetyl(amino acid) binding peptide. In various embodiments, peptide region 58 may comprise a phospho(amino acid) binding peptide or an acetyl(amino acid) binding peptide, and peptide region 55 and/or peptide region 56 may comprise either a site-specific kinase recognition amino acid sequence or a site-specific acetyltransferase recognition amino acid sequence. In various embodiments, peptide region 55 may comprise a phospho(amino acid) binding peptide or an acetyl(amino acid) binding peptide, and peptide region 56 may comprise either a site-specific kinase recognition amino acid sequence or a site-specific acetyltransferase recognition amino acid sequence.

Accordingly, a site-specific kinase recognition amino acid sequence or a site-specific acetyltransferase recognition amino acid sequence may be located in peptide region 55, 56 or 58, and a phospho(amino acid) binding peptide or an acetyl(amino acid) binding peptide may be located in peptide region 55, 56 or 58, provided however, that the kinase or acetyltransferase recognition substrate is not located in the same peptide region as a binding peptide. Thus, the biosensors disclosed herein are not limited to a construction wherein a peptide linker comprises an enzyme recognition sequence, and a binding peptide is located at the end of a fluorogen-activating peptide or blocking peptide, opposite the peptide linker. In various embodiments, the biosensors disclosed herein comprise a peptide linker comprising a binding peptide, and a site-specific enzyme recognition sequence located at an end of a fluorogen-activating peptide and/or a blocking peptide, opposite the peptide linker. In various embodiments, the biosensors disclosed herein comprise a site-specific enzyme recognition sequence located at an end of a fluorogen-activating peptide or a blocking peptide, opposite the peptide linker, and a binding peptide located at the opposite end of the peptide construct.

In various embodiments, the disclosed biosensors may function in a reversible manner. For example, biosensors comprising a fluorogen-activating peptide, a blocking peptide, a peptide linker comprising a site-specific kinase recognition amino acid sequence, and, optionally, a phospho (amino acid) binding peptide may function as biosensors for kinase and phosphatase activity. As a kinase biosensor, the peptide constructs according to embodiments disclosed herein may undergo a conformational change as a result of phosphorylation of the peptide linker, which may result in an at least partial disassociation between the fluorogen-activating peptide and the blocking peptide, which may result in an increase in fluorescence produced by an interaction between a fluorogen and the fluorogen-activating peptide.

In various embodiments, a kinase-activated (i.e., phosphorylated) biosensor may comprise a complex between a fluorogen molecule and the fluorogen-activating peptide. If this complex comes into contact with a phosphatase enzyme, the complex may be de-phosphorylated. The de-phosphorylation may cause the peptide construct to revert back to its original conformation, which may disrupt the interaction between the fluorogen and the fluorogen-activating peptide. This may result in a decrease in fluorescence. Thus, a phosphorylated biosensor according to various embodiments described herein may function as a phosphatase biosensor.

In addition, as an acetyltransferase biosensor, the peptide constructs according to embodiments disclosed herein may undergo a conformational change as a result of acetylation of the peptide linker, which may result in an at least partial disassociation between the fluorogen-activating peptide and the blocking peptide, which may result in an increase in fluorescence produced by an interaction between a fluorogen and the fluorogen-activating peptide.

In various embodiments, an acetyltransferase-activated (i.e., phosphorylated) biosensor may comprise a complex between a fluorogen molecule and the fluorogen-activating peptide. If this complex comes into contact with a de-acetylase enzyme, the complex may be de-acetylated. The de-acetylation may cause the peptide construct to revert back to its original conformation, which may disrupt the interaction between the fluorogen and the fluorogen-activating peptide. This may result in a decrease in fluorescence. Thus, an acetylated biosensor according to various embodiments described herein may function as a de-acetylase biosensor.

In various embodiments, the fluorogen-activating peptide and the blocking peptide may comprise an antibody or antibody fragment. Examples of antibody fragments finding utility in the disclosed embodiments include, but are not limited to, Fab, Fab', F(ab')$_2$, Fv, dsFv, scFv, and Fd fragments. In various embodiments, the fluorogen-activating peptide and the blocking peptide may comprise a variable chain domain ($V_H$ or $V_L$) of an antibody. In various embodiments, the fluorogen-activating peptide may comprise a variable heavy chain domain ($V_H$) of an antibody and the blocking peptide may comprise a variable light chain domain ($V_L$) of an antibody, and in other embodiments, the fluorogen-activating peptide may comprise a variable light chain domain ($V_L$) of an antibody and the blocking peptide may comprise a variable heavy chain domain ($V_H$) of an antibody. In various embodiments, the fluorogen-activating peptide may comprise a single-chain antibody. In various embodiments, the variable heavy chain domain ($V_H$) and the variable light chain domain ($V_L$) may be derived from different antibodies.

In various embodiments, the variable chain domains ($V_H$ or $V_L$) comprising the fluorogen-activating peptide and the blocking peptide may be derived from scFvs. scFvs may be derived by genetic engineering manipulations of antibody DNA. Using genetic engineering techniques known in the art, synthetic scFv genes may be constructed from gene segments coding for the variable domains of the heavy and light chains ($V_H$ and $V_L$) covalently linked by a synthetic DNA segment that codes for a peptide linker. The peptide linker may be of sufficient length (for example, 15 or more amino acid residues in length) to allow the $V_H$ and $V_L$ domains to associate intramolecularly into a characteristic $V_H/V_L$ conformation found at the antigen binding ends of native antibodies. A complex human scFv library comprising approximately $10^9$ synthetically recombined heavy and light chain variable regions is available in a yeast surface display format. See, for example, Feldhaus et al., *Nat. Biotechnol.* 21, 163-170, 2003; and Boder et al. *Nat. Bio-* technol. 15, 553-557, 1997, each of which is incorporated by reference herein in its entirety.

Specific interactions between particular target molecules and particular scFvs may be determined by screening a yeast surface-display scFv library. See, for example, Wittrup et al., *Methods Enzymol.* 328, 430-444, 2000; Boder et al, *Proc. Natl. Acad. Sci. USA* 97, 10701-10705, 2000; and Swers et al. *Nucleic Acids Res.* 32, e36, 2004, each of which is incorporated by reference herein in its entirety. Particular scFvs that specifically interact with particular fluorogens may be determined, for example, by screening a yeast surface-display scFv library. See, for example, Ozhalici-Unal et al., *JACS* 130, 12620-12621, 2008; and Szent-Gyorgyi et al., *Nat. Biotechnol.* 26, 235-240, 2008, each of which is incorporated by reference herein in its entirety. Other genetic selection methods for screening scFvs for specific interaction with target molecules are known in the art, such as, for example, phage display methods. Phage display systems, their construction and operation, and associated screening methods are described in detail, for example, in U.S. Pat. Nos. 5,702,892; 5,750,373, 5,821,047; 5,948,635; and 6,127,132, each of which is incorporated by reference herein in its entirety.

Examples of scFvs that specifically interact with thiozole orange derivatives and scFvs that specifically interact with malachite green derivatives are described in Szent-Gyorgyi et al., *Nat. Biotechnol.* 26, 235-240, 2008, and in International Patent Application No. PCT/US2008/051962, each of which is incorporated by reference herein in its entirety. In some embodiments, scFvs require both the $V_H$ and $V_L$ domains for fluorogen interaction. In other embodiments, only the $V_H$ domain or the $V_L$ domain, alone, is necessary for a scFv to specifically interact with a fluorogen and modulate the fluorescence signal produced by the fluorogen. In these embodiments, the associated partner domain may contribute nothing to (or in fact inhibit) interaction between the scFv and a cognate fluorogen. Functional single-domain (either $V_H$ or $V_L$) scFvs may interact with cognate fluorogens with a high degree of affinity and specificity without an associated partner domain (either $V_L$ or $V_H$, respectively). In these embodiments, the fluorogen-activating variable domain may be described as a single domain antibody.

In some embodiments, a functional $V_H$ or $V_L$ domain may be paired with a non-functional partner domain comprising a $V_H$ or $V_L$ domain from a different antibody (or different scFv). In these embodiments, if the functional fluorogen-interacting domain is a $V_H$ domain, then the non-functional partner domain may be a $V_L$ domain. If the functional fluorogen-interacting domain is a $V_L$ domain, then the non-functional partner domain may be a $V_H$ domain. The functional domain and the non-functional partner domain may be covalently linked through a peptide linker, thereby forming a peptide construct comprising a synthetic hybrid scFv structure.

Figure 5:
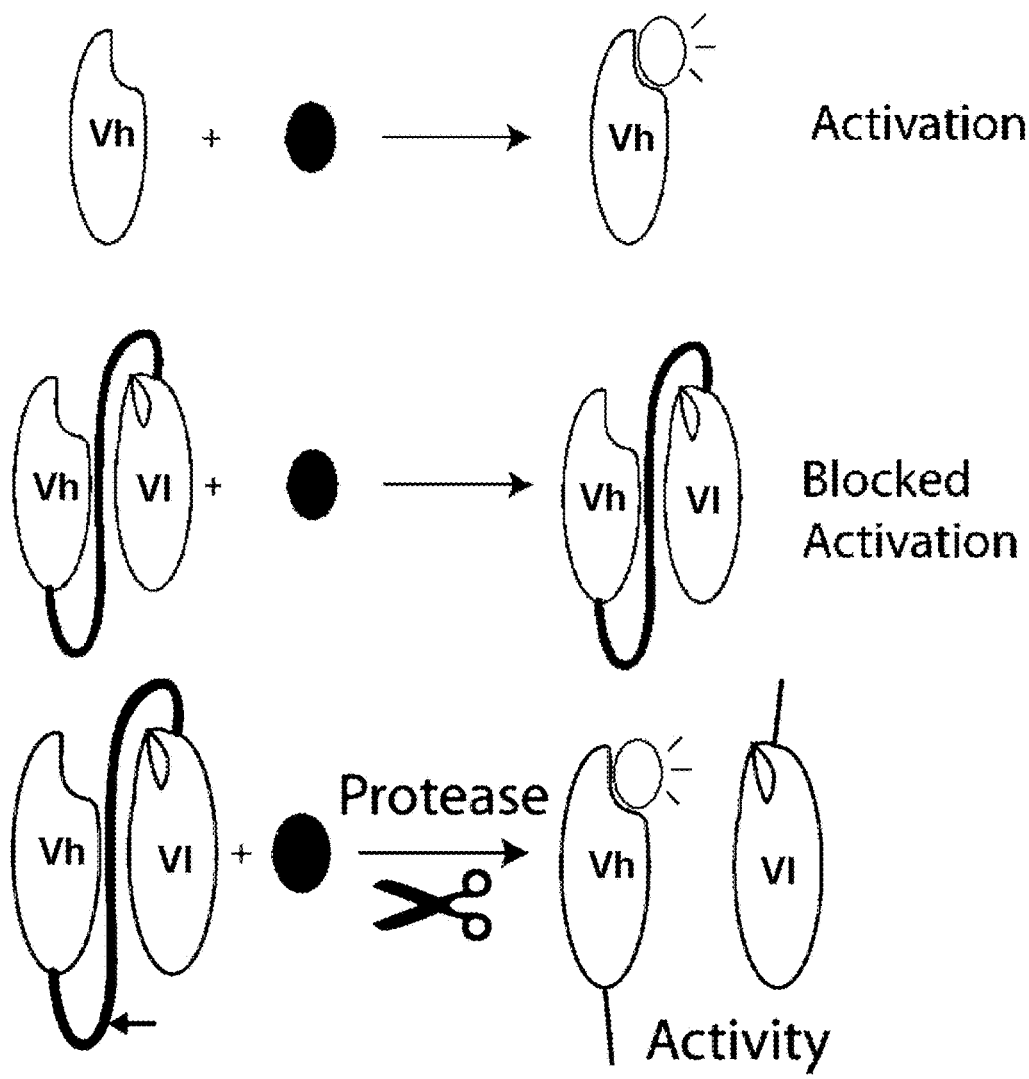
FIG. 5 is a diagram illustrating a single-domain antibody comprising a variable heavy chain domain fragment, a blocked hybrid scFv comprising the variable heavy chain domain fragment, and a protease biosensor construct comprising the variable heavy chain domain fragment according to various embodiments disclosed herein.

The non-functional partner domain may associate with the functional domain when covalently linked through a peptide linker. The association may partially or totally block the active portion of the functional domain, which may interfere with the fluorogen-interaction and partially or totally inhibit the activity of the functional domain. In this embodiment, the non-functional partner domain operates as a blocking domain. As illustrated in FIG. 5 for a protease cleavage embodiment, if the peptide linker is cleaved (or otherwise modified resulting in a conformational change in the peptide construct), then the non-functional blocking domain and the functional domain may at least partially dissociate. The at least partial dissociation may at least partially unblock the active portion of the functional domain, which may allow the functional domain to interact with a fluorogen and modulate its fluorescence signal.

The selection of a non-functional blocking domain to pair with a functional domain to form a synthetic hybrid scFv may be conducted using known genetic engineering techniques. Synthetic two-domain scFv genes may be constructed, for example, by digesting with appropriate restriction enzymes the full-length, two-domain plasmids coding for the scFvs selected from a yeast library as described above. The DNA coding for the variable domain of the scFv that does not contribute to the fluorogen interaction activity of the scFv may be removed from the digested plasmids. The removed DNA may be replaced with a new variable domain segment from a different scFv to form a hybrid plasmid. The fusion protein expressed from the hybrid plasmid may comprise a peptide construct comprising a synthetic hybrid scFv.

A hybrid scFv expressed as a surface protein (in a yeast surface-display system for example) from a hybrid plasmid as described above may be assayed for fluorogen interaction by flow cytometry, for example. In this manner, the fluorogen-interaction activity of a two-domain synthetic hybrid scFv may be determined, and non-functional blocking domains may be selected that inhibit (or completely block) the fluorogen-interaction activity of a functional domain.

The construction using molecular cloning methods of an artificial peptide construct comprising a pairing of unrelated $V_H$ and $V_L$ domains (one of which possesses fluorogen-interaction activity and one of which does not) covalently linked through a peptide linker, may serve as a platform for various embodiments described herein. Not wishing to be bound by theory, the natural association of some $V_H$ and $V_L$ domains and the interaction of their complementarity determining region ("CDR") loops in the two-domain scFv architecture may somehow interfere with fluorogen interaction by the functional single domain in a hybrid scFv. By way of example, the interface between associated $V_H$ and $V_L$ domains may wholly or partially block the fluorogen-interacting active domain in the single functional $V_H$ or $V_L$ domain. Alternatively, or in addition, the association of the $V_H$ and $V_L$ domains may result in a rearrangement of the three-dimensional structure of the CDR loops of the active domain in the single functional $V_H$ or $V_L$ domain, which may inhibit interaction with a cognate fluorogen.

In various embodiments, the disclosed biosensors may comprise a peptide construct comprising a fluorogen-activating peptide comprising a functional fluorogen-interacting $V_H$ or $V_L$ domain, and a blocking peptide comprising a non-functional blocking domain of the opposite type. In various embodiments, the fluorogen-activating peptide comprising a $V_H$ or $V_L$ domain, and the blocking peptide comprising a variable domain of the opposite type may be linked through a peptide linker comprising an amino acid sequence that is specifically recognized as a cleavage substrate by a cognate protease, as a phosphorylation substrate by a cognate kinase, or as an acetylation substrate by a cognate acetyltransferase. In various embodiments, the biosensors may further comprise a phospho(amino acid) binding peptide or an acetyl(amino acid) binding peptide.

In various embodiments, when the peptide linker is modified (e.g., cleaved, phosphorylated, or acetylated), the peptide comprising a functional fluorogen-interacting $V_H$ or $V_L$ domain, and the peptide comprising a variable blocking domain of the opposite type, at least partially dissociate such that the peptide comprising a functional fluorogen-interacting $V_H$ or $V_L$ domain may interact with a fluorogen, thereby modulating the fluorescence signal produced by the fluorogen. In this manner, a peptide construct comprising a fluorogen-activating peptide linked to a blocking peptide through a peptide linker may function as a biosensor to detect and analyze enzyme (e.g., protease, kinase, acetyltransferase) activity.

Various embodiments disclosed herein will now be illustrated in the following, non-limiting examples.

EXAMPLES

Example 1: scFvs that Specifically Interact with Fluorogen scFvs that elicited fluorescence enhancement from three fluorogenic dyes (thiazole orange ("TO"), dimethyl indol red ("DIR"), and malachite green ("MG")) were isolated. The scFvs were isolated using a yeast cell surface display library comprising approximately $10^9$ recombinant human scFvs derived from cDNA representing a naïve germline repertoire. The yeast cell surface display library was obtained from Pacific Northwest National Laboratory (PNNL). The materials, methods and protocols for using the PNNL yeast cell surface display library are described in the "Yeast Display scFv Antibody Library User's Manual," Revision: MF031112, available from PNNL, Richland, Wash. 99352, USA (http://www.sysbio.org/dataresources/index.stm), the contents of which is incorporated by reference herein in its entirety. The methodology for the PNNL Yeast Display scFv Antibody Library was originally described in Feldhaus et al., Nat. Biotechnol. 21, 163-170, 2003.

The PNNL scFv library is specifically designed to display full-length scFvs whose expression on the yeast cell surface can be monitored with either N-terminal hemagglutinin ("HA") or C-terminal c-myc epitope tags. These epitope tags allow monitoring by flow cytometry of scFv clones, or libraries of scFv clones, for surface expression of full-length scFv, for example. The extra cellular surface display of scFv by Saccharomyces cerevisiae also allows the detection of appropriately labeled antigen-antibody interactions by flow cytometry, for example. As a eukaryote, S. cerevisiae offers the advantage of post-translational modifications and processing of mammalian proteins, and therefore, is well suited for expression of human derived antibody fragments. In addition, the short doubling time of S. cerevisiae allows for the rapid analysis and isolation of antigen-specific scFv antibodies.

The PNNL yeast display system uses the a-agglutinin yeast adhesion receptor to display recombinant proteins on the surface of S. cerevisiae (Boder et al., Biotechnol. Prog. 14, 55, 1998; Boder et al., Nat. Biotechnol. 15, 553, 1997). In S. cerevisiae, the a-agglutinin receptor acts as an adhesion molecule to stabilize cell-cell interactions and facilitate fusion between mating "a" and q haploid yeast cells. The receptor consists of two proteins, Aga1 and Aga2. Aga1 is secreted from the cell and becomes covalently attached to b-glucan in the extra cellular matrix of the yeast cell wall. Aga2 binds to Aga1 through two disulfide bonds, and after secretion remains attached to the cell via Aga1. The yeast display system takes advantage of the association of Aga1 and Aga2 proteins to display a recombinant scFv on the yeast cell surface.

The gene of interest is cloned into the pYD1 vector (Invitrogen), or a derivative of it, in frame with the AGA2 gene. The resulting construct is transformed into the EBY100 S. cerevisiae strain containing a chromosomal integrant of the AGA1 gene. Expression of both the Aga2 fusion protein from pYD1 and the Aga1 protein in the EBY100 host strain is regulated by the GAL1 promoter, a tightly regulated promoter that does not allow any detectable scFv expression in absence of galactose. Upon induction with galactose, the Aga1 protein and the Aga2 fusion protein associate within the secretory pathway, and the epitope-tagged scFv antibody is displayed on the cell surface. Molecular interactions with the scFv antibody can be easily assayed by incubating the cells with a ligand of interest. A combination of two rounds of selection using magnetic particles followed by two rounds of flow cytometric sorting will generally allow recovery of clones of interest.

The PNNL yeast display system may be utilized to isolate higher affinity clones from small mutagenic libraries generated from a unique antigen binding scFv clone (Boder et al., Proc. Natl. Acad. Sci. USA 97, 10701, 2000). Mutagenic libraries are constructed by amplifying the parental scFv gene to obtain higher affinity variants using error-prone PCR to incorporate 3 to 7 point mutations/scFv, for example. The material is cloned into the surface expression vector using the endogenous homologous recombination system present in yeast, known as "Gap-Repair". Gap repair is an endogenous homologous recombination system in S. cerevisiae that allows gene insertion in chromosomes or plasmids at exact sites by utilizing as little as 30 base pair regions of homology between a gene of interest and its target site. This allows mutated libraries of clones to be rapidly generated and screened by selecting the brightest antigen binding fraction of the population using decreasing amounts of antigen relative to the IQ of the starting parental clone.

The PNNL yeast display system was utilized to clone scFvs that specifically bind the fluorogenic dyes thiazole orange ("TO"), malachite green ("MG"), dimethyl indol red ("DIR"), and derivatives thereof. EBY100 was host to the yeast display library and YVH10 was used to secrete scFvs as described in Feldhaus et al., Nat. Biotechnol. 21, 163-170, 2003. For analysis of individual scFvs, pPNL6 plasmids were transferred to JAR200 (Mat a ura3-52, trp1, leu2δ200, his3δ200, pep4:HIS3, prbd1.6R, can1, GAL, GAL promoter-AGA1::URA3:G418R). A modified PBS buffer (PBS pH 7.4, 2 mM EDTA, 0.1% w/v Pluronic F-127 (Molecular Probes, Invitrogen)) was used for magnetic bead enrichment, fluorescence-activated cell sorting ("FACS") experiments, and all assays of yeast surface displayed or purified scFvs.

As used herein, the names of isolated and characterized scFvs consist of three components: i) the scFv chain configuration, with H designating the heavy variable ($V_H$) region and L designating the light variable ($V_L$) region; ii) a unique numerical identifier designating the parent isolate and its affinity maturation lineage in the format "parent#.1stgeneration#.2ndgeneration#" and iii) the fluorogenic dye used to isolate the scFv. Thus, for example, "HL1-TO1" indicates the parent isolate of the TO-activating, $V_H$ and $V_L$ clone 1, and "L5.1-MG" indicates the first affinity matured variant of the MG-activating, $V_L$-only clone 5.

The results are reported and discussed in Szent-Gyorgyi et al., Nat. Biotechnol. 26, 235-240, 2008; and in International Patent Application No. PCT/US2008/051962, each of which is incorporated by reference herein in its entirety. The DNA and amino acid sequences of the scFv fragments are disclosed in PCT/US2008/051962 and reproduced herein as SEQ ID NOS:21-40. These sequences are incorporated by reference herein in their entirety as though expressly listed herein.

Figure 6:
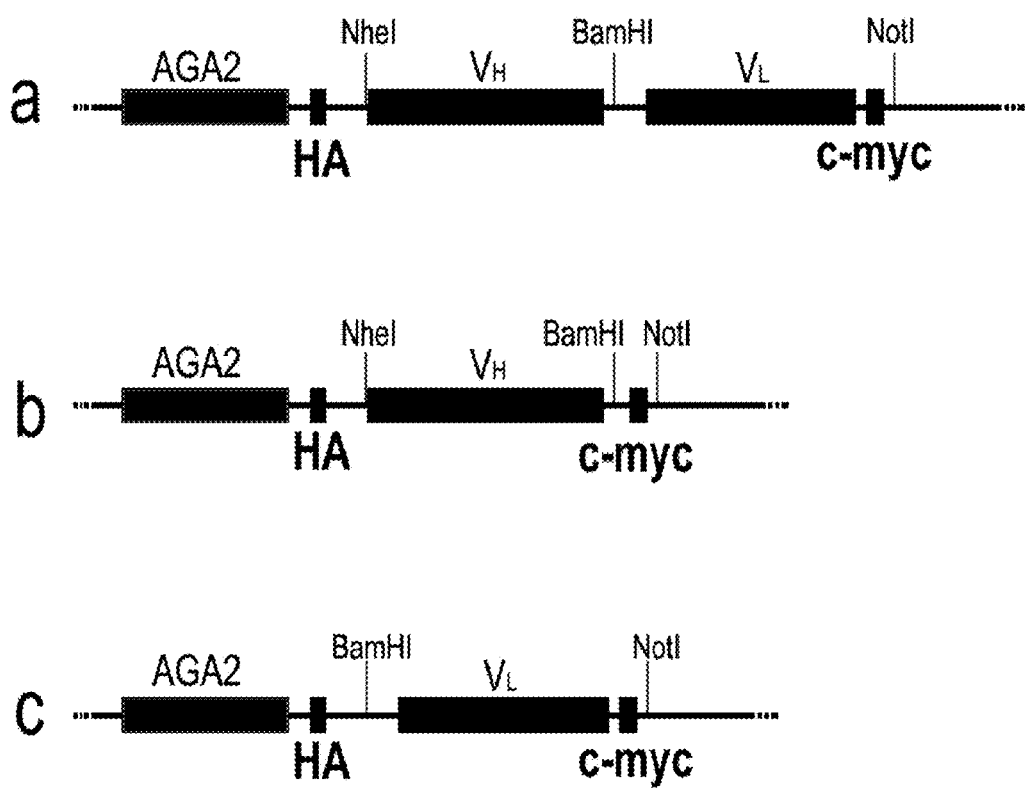
FIG. 6 presents diagrams depicting the genetic structure of single chain antibodies in a pPNL6 plasmid as described herein; diagram (a) depicts a plasmid segment comprising DNA coding for a variable heavy chain antibody fragment and a variable light chain antibody fragment; diagram (b) depicts a plasmid segment comprising DNA coding for a variable heavy chain antibody fragment where the DNA coding for a variable light chain antibody fragment has been excised; diagram (c) depicts a plasmid segment comprising DNA coding for a variable light chain antibody fragment where the DNA coding for a variable heavy chain antibody fragment has been excised.

Example 2: Genetic Dissection of Two-Domain scFvs scFv genes in the Pacific Northwest National Laboratory yeast surface display library were cloned in a pPNL6 plasmid, where they were expressed as fusion proteins between an N-terminal HA-tagged AGA2p protein and a C-terminal c-myc epitope as shown in FIG. 6a. The $V_H$ and $V_L$ gene segments were linked by a flexible 15 amino acid peptide linker comprising 3 repeats of the sequence Gly$_4$Ser. Two-domain ($V_H$ and $V_L$) scFv clones which were found to activate fluorescence in TO, MG and DIR fluorogens were reduced to their $V_H$-only and/or $V_L$-only plasmids by DNA manipulation.

Single variable domain reduction plasmids were constructed using restriction sites within the pPNL6 vector and the (Gly$_4$Ser)$_3$ peptide linker. $V_H$ only plasmids were constructed by subcloning the $V_H$ domain-coding restriction fragments into an empty pPNL6 vector. After cleavage with NheI and BamH1 restriction enzymes, $V_H$ domain-coding fragments from 2-domain scFvs were separated from the rest of the plasmid DNA by agarose gel electrophoresis and purified with a QIAGEN Gel Extraction Kit (Qiagen Inc., Valencia, Calif. 91355, USA). A partial BamH1 restriction enzyme digest of an HL-A8-DIR 2-domain fluorogen-activating scFv was performed due to an internal BamHI restriction enzyme site in the A8-DIR $V_H$ domain. Empty pPNL6 vector was cut using the same pair of restriction enzymes to remove the NheI/BamH1 stuffer fragment and the backbone was purified in a similar manner to prepare for ligation. $V_H$ domains were then ligated into the pPNL6 vector backbone following the suggested protocol in an NEB Quick Ligation™ Kit (New England Biolabs Inc., Ipswich, Mass. 01938, USA).

A special vector pPNL6(HL1-TO1 $V_L$) was constructed in which to clone $V_L$ domains. pPNL6 carrying the scFv gene HL1-TO1 was digested with BmtI (an isoschizomer of NheI) and BamH1. The DNA ends were treated with T4 DNA polymerase (according to the NEB protocol for blunting DNA ends, NEB Quick Blunting™ Kit). DNA was purified from this reaction using the QIAGEN PCR Cleanup Kit (Qiagen Inc., Valencia, Calif. 91355, USA). DNA molecules were circularized by ligation at a total DNA concentration <1 µg/ml. This series of enzymatic treatments deleted the HL1-TO1 $V_H$ domain-coding DNA while retaining the $V_L$ domain-coding DNA. It also restored the BamH1 site and preserved the reading frame between the Aga2 gene and the remaining $V_L$ domain. $V_L$ only plasmids were constructed by gel purifying the $V_L$ domain-coding restriction fragments from all other two-domain plasmids after cleavage with BamH1 and NotI. The pPNL6(HL1-TO1 $V_L$) vector was cut using the same pair of enzymes to remove the HL1-TO1 $V_L$ stuffer fragment and the backbone gel purified to prepare for ligation. $V_L$ domains were ligated into this vector backbone following the suggested protocol in the NEB Quick Ligation™ Kit.

The modified single-domain ($V_H$ or $V_L$) scFv genes were expressed from pPNL6 plasmids that generated surface displayed fusion proteins tagged with both HA and c-myc epitopes (FIGS. 6b and 6c).

Example 3: Single Variable Domains of scFvs that Specifically Interact with Fluorogen Flow cytometry was used to measure both the amount of scFv (c-myc epitope) expressed, and the amount of fluorogen activating activity of the modified, surface-expressed scFvs. For each induced and un-induced sample, $10^6$ cells were washed twice in wash buffer (1× phosphate buffered saline, 2 mM EDTA, 0.1% Pluronic F-127) and re-suspended in 100 µl wash buffer containing 2 µg mouse monoclonal anti-c-myc antibody (Roche clone 9E10). Following a 1-hour incubation on ice, the cells are washed twice in wash buffer and re-suspended in 100 µl wash buffer containing 0.8 µg appropriately labeled goat anti-mouse secondary antibody. Alexa-fluor 647 conjugated secondary antibodies were used for TO dye activating scFvs. Alexa-fluor 488 conjugated secondary antibodies were used for MG and DIR activating scFvs. Alexa-fluor antibodies are available from Invitrogen.

The cells were again washed twice and re-suspended in 500 µl of wash buffer to which fluorogen was added to a concentration 10× the measured cell-surface $K_d$ for the particular scFv. A parallel set of samples was treated with a 1 µM final concentration of propidium iodide, a vital dye used as a marker for cell viability. scFv activation of the fluorogen was assessed by flow-cytometry on a Becton Dickinson FACS Vantage SE cytometer. Fluorescence was excited using the 488 nm laser for TO fluorogen and the Alexa-fluor 488 conjugated antibodies and fluorescence signals were measured at 530 nm. MG and DIR fluorogen and Alexa-fluor 647 conjugated antibodies were excited using the 635 nm laser and fluorescence signals were measured at 685 nm. A ratio of fluorescence signal from the appropriate fluorogen channel and the c-myc channel was calculated to determine signal per scFv molecule in order to allow comparison of one scFv expressing cell sample to another.

Figure 7:
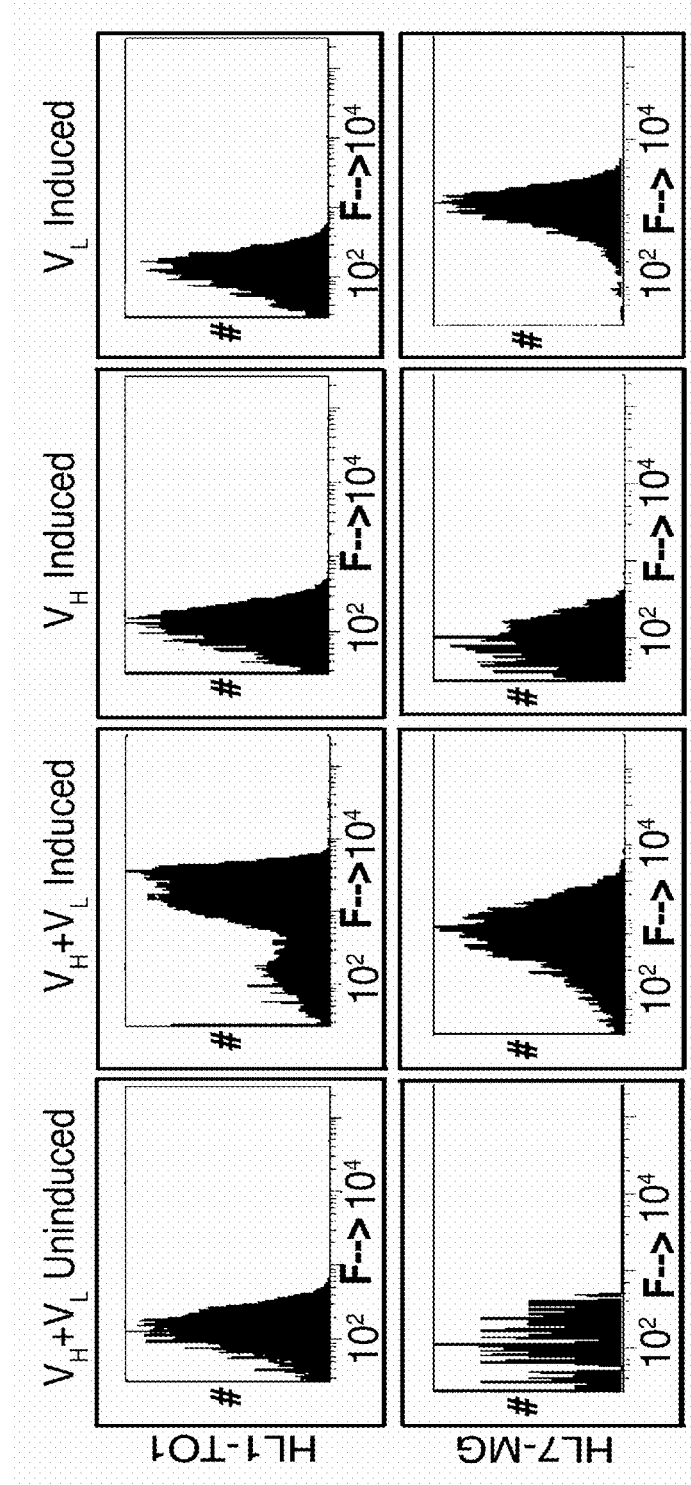
FIG. 7 presents qualitative plots of cytometric data for single chain antibodies and fragments thereof displayed on the surface of yeast ("FL" refers to full length single chain antibodies, "HO" refers to variable heavy single-domain antibody fragments, and "LO" refers to variable light single-domain antibody fragments)

Analysis of the two-domain and single-domain peptides expressed from the engineered plasmids described in Example 2 provided results that fell into two distinct groupings, illustrated by the cytometric analyses shown in FIG. 7 ("FL" refers to full length scFvs, "HO" refers to variable heavy domain only single-domain scFv fragments, and "LO" refers to variable light domain only single-domain scFv fragments). For one group, illustrated, for example, by the scFv HL1-TO1, the full-length two-domain (FL) scFv shows typical fluorescence activation of the fluorogen compared to un-induced cells (significant numbers of cells appearing at higher fluorescence). However, neither of the individual $V_H$ or $V_L$ domains ($V_H$-only (HO) and $V_L$-only (LO), respectively) activated the fluorogen (no difference compared to un-induced cells). The other group, illustrated, for example, by HL7-MG, also shows typical fluorescence activation of the fluorogen by the full-length two-domain scFv compared to un-induced cells. However, the molecular dissection of the $V_H$ and $V_L$ domains reveals that the fluorogen-activating activity resides completely in the $V_L$ domain.

Example 4: Quantification of Fluorogen Activation by Single-Domains of scFvs The amount of scFv expressed on the surface of the yeast cells described in Example 3 was determined by fluorescence labeling of the c-myc epitope fused to the C-terminal end of each scFv. The population average fluorescent intensity of the c-myc signal was used to normalize the population average fluorogen activation signal to provide a quantification of the fluorogen activation by the surface-displayed scFvs. These results are presented in Table 1, where the fluorogenic activity of each dissected construct (i.e., the isolated single-domain scFvs) is expressed as a percentage of the fluorogenic activity of its parent two-domain clone (ΔH and ΔL refer to the removed domain in each dissected construct).

TABLE 1

Fluorogen activating activity of scFvs

| scFv | Percent Fluorogenic Activity |
|---|---|
| HL1-TO1 | 100.0 |
| H(ΔL)1-TO1 | 9.6 |
| (ΔH)L1-TO1 | 6.4 |
| HL4-MG | 100.0 |
| H(ΔL)4-MG | 1.7 |
| (ΔH)L4-MG | 1.7 |
| HL7-MG | 100.0 |
| H(ΔL)7-MG | 3.7 |
| (ΔH)L7-MG | 114.8 |
| HL9-MG | 100.0 |
| H(ΔL)9-MG | 7.1 |
| (ΔH)L9-MG | 111.9 |
| HL-A8-DIR | 100.0 |
| H(ΔL)-A8-DIR | 4.2 |
| (ΔH)L-A8-DIR | 3.9 |
| HL-J6-DIR | 100 |
| H(ΔL)-J6-DIR | 3.2 |
| (ΔH)L-J6-DIR | 3.1 |
| HL-K7-DIR | 100.0 |
| H(ΔL)-K7-DIR | 3.2 |
| (ΔH)L-K7-DIR | 4.2 |
| HL-K10-DIR | 100.0 |
| H(ΔL)-K10-DIR | 16.8 |
| (ΔH)L-K10-DIR | 88.6 |
| HL-M8-DIR | 100.0 |
| H(ΔL)-M8-DIR | 18.9 |
| (ΔH)L-M8-DIR | 72.0 |

The quantitative data presented in Table 1 indicate that five of the scFvs require both $V_H$ and $V_L$ domains for fluorogen activation activity. That is, individual $V_H$ or $V_L$ domains retain only a few percent of the fluorogen activation activity of the parent scFv. The data also indicate that four scFvs possessed fluorogen activation activity that can be attributed to a single variable domain. Expression of the $V_L$ domain of HL7-MG, HL9-MG, HL-K10-DIR, or HL-M8-DIR is sufficient to activate the fluorescence of the cognate fluorogen for each scFv. Sequence analysis of the individual domains of HL7-MG and HL9-MG reveals 92% sequence identity at the protein level for the $V_L$ domains, while the $V_H$ domains share approximately 75% sequence identity. The $V_L$ domains of HL-K10-DIR and HL-M8-DIR are 100% identical while the $V_H$ domains share approximately 46% sequence identity.

Example 5: Construction of Synthetic Hybrid Two-Domain scFvs

Synthetic two-domain hybrid scFvs comprising various single active variable domains and single inactive variable domains of the opposite type were constructed and the activity of the hybrids was measured. For the single active variable domains in certain hybrids, a $V_H$ domain (H6-MG) was used. For the single active variable domains in certain other hybrids, $V_L$ domains from HL7-MG, HL9-MG, L5.1-MG, and HL-M8-DIR were used.

The synthetic two-domain scFv genes were constructed by DNA manipulation of the corresponding gene segments in the yeast surface-display vector pPNL6. Full-length, two-domain plasmids were digested with appropriate restriction enzyme to remove the variable domain-coding DNA of interest, which was then physically replaced with a new variable domain segment. All scFv genes were in pPNL6 vector backbones. Thus for swapping $V_H$ domains NheI/BamHI restriction digests were performed to remove and replace $V_H$ domains. BamHI/NotI restriction digests were performed to remove and replace $V_L$ domains (FIG. 6a). Plasmid backbones and domain fragments were purified by gel electrophoresis. Purified $V_H$ and $V_L$ domains and plasmid backbones from different starting plasmids were combined and joined by DNA ligation to form new full-length hybrid genes.

Plasmid DNA in ligation reactions were transformed into chemically competent TOP10 or Mach1™ *E. coli* (Invitrogen) or electroporation competent DH5α *E. coli* (Bioline). Plasmid DNA was extracted from *E. coli* using a miniprep kit (QIAGEN). scFv genes in all plasmids were re-sequenced to confirm they contained the correct fragments and were in frame with the c-myc epitope (GeneWiz).

Selective growth media (SD+CAA) and induction media (SGR+CAA) for yeast carrying the pPNL6 surface display plasmid have been previously described (see, e.g., Feldhaus et al., *Nat. Biotechnol.* 21, 163-170, 2003; and Yeast Display scFv Antibody Library User's Manual," Revision: MF031112, available from PNNL, Richland, Wash. 99352, USA). pPNL6 plasmids containing the scFv hybrid gene constructs were transformed into EBY100 yeast by EZ Yeast Transformation Kit (BIO 101, Vista, Calif. 92083, USA). The EBY100 yeast transformants were grown for 48 hours at 30° C. in SD+CAA selective growth media. When the cultures reached an optical density at 660 nm of >1.0 (>2×10$^7$ cells/ml) the yeast cells were harvested by centrifugation and re-suspended in SGR+CAA selective induction medium at a concentration of 2×10$^7$ cells/ml. These induction cultures were incubated with shaking for 72 hours at 20° C. For each transformant, an additional culture was maintained in selective growth media as an un-induced control.

Example 6: Quantification of Fluorogen Activation by Hybrid Two-Domain scFvs

Fusion proteins expressed on the surface of yeast were assayed for fluorogen activation by flow cytometry and normalized, as above, by determining the total amount of surface displayed c-myc-tagged fusion protein. The activity of the parent single active variable domain was set to 100% and the hybrid scFv activity expressed relative to the parent. The results are presented in Table 2.

TABLE 2

Fluorogen activating activity of hybrid scFvs

| $V_H$ domain | $V_L$ domain | Percent Fluorogenic Activity |
|---|---|---|
| H6-MG | — | 100 |
| H6-MG | HL1-TO1 | 0.7 |
| H6-MG | HL4-MG | 79.5 |
| — | HL7-MG | 100 |
| HL4-MG | HL7-MG | 4.3 |
| HL9-MG | HL7-MG | 45.7 |
| — | HL9-MG | 100 |
| HL4-MG | HL9-MG | 5.4 |
| HL7-MG | HL9-MG | 95.6 |
| — | L5.1-MG | 100 |
| HL4-MG | L5.1-MG | 38.3 |
| HL1-TO1 | L5.1-MG | 130.1 |
| HL7-MG | L5.1-MG | 125.2 |
| HL9-MG | L5.1-MG | 87.8 |

TABLE 2-continued

Fluorogen activating activity of hybrid scFvs

| $V_H$ domain | $V_L$ domain | Percent Fluorogenic Activity |
|---|---|---|
| — | HL-M8-DIR | 100 |
| HL1-TO1 | HL-M8-DIR | 23.4 |
| HL4-MG | HL-M8-DIR | 3.1 |

As shown in Table 2, the fluorogen activating activity of some of the active single-domains is inhibited (or blocked) by the presence of various partner domains. For example, the fluorogen-activating activity of the $V_H$ domain H6-MG is blocked greater than 99% by the presence of the $V_L$ domain of HL1-TO1, and the activity of the $V_L$ domains of HL7-MG, HL9-MG and HL-M8-DIR is blocked approximately 95% by the $V_H$ domain of HL4-MG.

Example 7: Isolation and Purification of One-Domain scFvs and Two-Domain Hybrid scFvs In order to verify that the activity modulation of the single-domain scFvs was not due to an artifact of the yeast surface display of the protein, soluble versions of the fluorogenically active $V_H$ single-domain of H6-MG and the "blocked construct" hybrid scFv comprising the $V_H$ domain of H6-MG and the $V_L$ domain of HL1-TO1 were expressed in E. coli, isolated and purified.

The genes encoding for single-domain scFvs and hybrid blocked two-domain scFvs were isolated from pPNL6 clones and tailed with SfiI restriction enzyme sites by anchored PCR. The forward primer for amplifying and SfiI-tailing the H6-MG gene is:

(SEQ ID NO: 61)
5'-GGCCCAGCCGGCCATGGCGCAGGTGCAGCTGCAGGAGTGC-3'.

The reverse primer for amplifying and SfiI-tailing the H6-MG gene is:

(SEQ ID NO: 62)
5'-GGCCCCCGAGGCCTCGGAGACAGTGACCAGGGTACC-3'.

The forward primer for amplifying and SfiI-tailing the two-domain hybrid containing the VH domain of H6-MG and the VL domain of HL1-TO1 is the same. The reverse primer for amplifying and SfiI-tailing the two-domain hybrid containing the VH domain of H6-MG and the VL domain of HL1-TO1 is:

(SEQ ID NO: 63)
5'-GGCCCCCGAGGCCCCTAGGACGGTGAGCTTGGTCC-3'.

PCR products were TOPO cloned (Invitrogen) and sequenced to verify faithful amplification. SfiI fragments were gel purified after SfiI digestion and ligated into SfiI-digested pAK400 (Krebber et al., J. Immuno. Meth. 201, 35-55, 1997) between a pelB leader sequence and His$_6$ tag. pAK400 is an E. coli periplasmic secretion vector for high-level expression of scFvs under the control of a wild-type lac promoter and IPTG inducible promoter. E. coli transformed with the pAK400 plasmids were grown to late log phase and induced with 1 mM IPTG in fresh media for 5 hours at 25° C.

Periplasmic proteins were isolated by osmotic shock (Maynard et al., J. Immuno. Meth. 306, 51-67, 2005) and dialyzed in a 10 mM Tris, 500 mM NaCl buffer, pH 8.0. Periplasmic, secreted scFvs were purified via the C-terminal His$_6$-tag by Nickel-NTA chromatography (QIAGEN). The periplasmic protein extract from 1 liter of culture was incubated with 0.5 ml settled volume of Nickel-NTA resin for 1 hour. The column was poured with this resin and the flow-through applied to the column a second time. The column was washed with buffer containing 20 mM imidazole, 10 mM Tris, 100 mM sodium phosphate, 300 mM NaCl, pH 8.0. His$_6$-tagged protein was eluted in buffer containing 250 mM imidazole, 10 mM Tris, 100 mM sodium phosphate, 300 mM NaCl, pH 8.0, and collected in 8, 500 μL fractions. All purification steps and storage of proteins were performed at 4° C. All fractions along with initial flow through and washes were analyzed by 15% SDS-PAGE gel electrophoresis to monitor purification.

This procedure was used to successfully produce isolated homogenous and soluble versions of the fluorogenically active $V_H$ single-domain of H6-MG and the "blocked construct" hybrid comprising the $V_H$ domain of H6-MG and the $V_L$ domain of HL1-TO1.

Example 8: Isolated One-Domain scFv and Two-Domain Hybrid scFv Activity Assay

Figure 8:
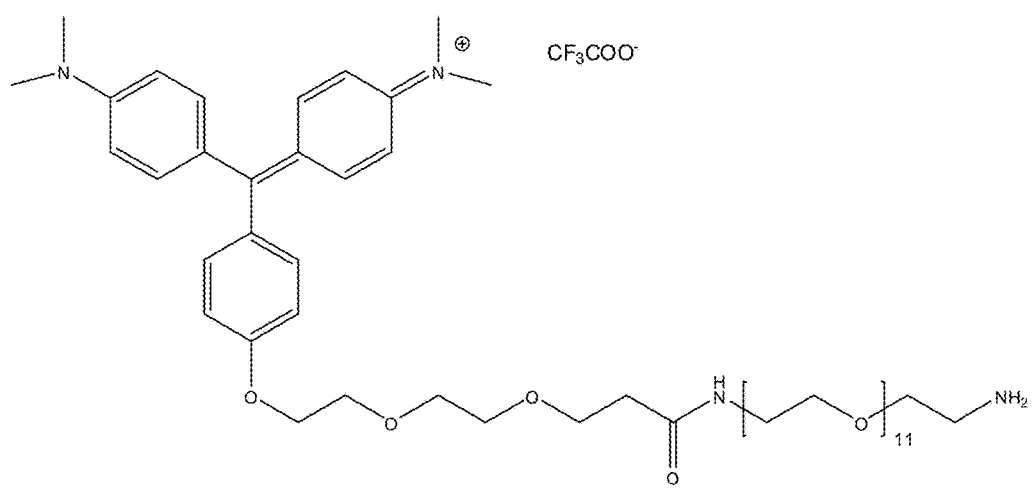
FIG. 8 is a molecular schematic of a malachite green fluorogen derivative.

Fluorogen-titration experiments were performed with the soluble proteins isolated in Example 7 to determine the $K_d$ of MG for each protein. The fluorogen titration analyses were performed on a TECAN Saffire2 plate reader in black, 96-well, flat bottom microtiter plates. 500 ng of purified protein was mixed with MG-11P-NH$_2$ fluorogen (FIG. 8) in wash buffer in a final volume of 100 Fluorogen concentrations varied from 0 to 20 μM in a 3-fold serial dilution series. MG fluorogen samples were excited at 625 nm and emission was detected at 660 nm.

Figure 9:
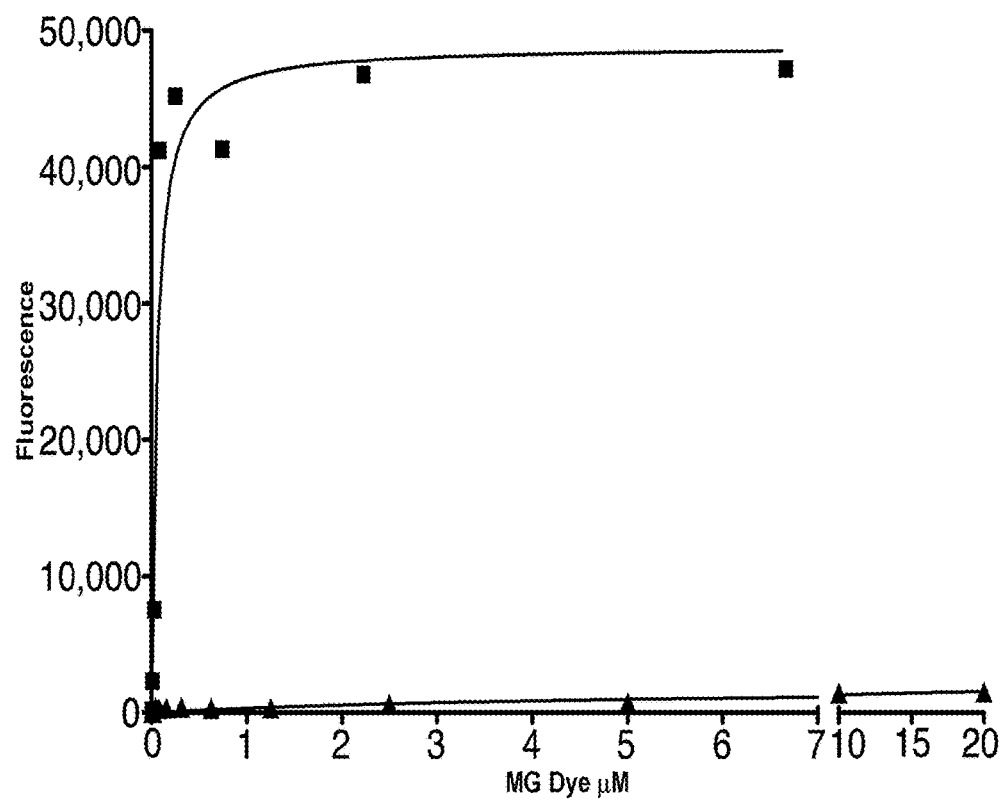
FIG. 9 is a graph presenting the results of a fluorogen titration analysis of a variable heavy single-domain antibody fragment (square-shaped data points) and a hybrid blocked single chain antibody (triangle-shaped data points)

The results of the titrations are shown in FIG. 9. The $K_d$ of H6-MG was measured in these experiments to be 50 nM. The apparent $K_d$ of the blocked construct was at least 4.9 μM. The solution $K_d$ of the blocked construct is at least two orders of magnitude higher than the active single-domain that is contained in the hybrid scFv. These results confirm that it is the partnering of the two domains in the hybrid that inhibits the activity of the H6-MG $V_H$ domain and not some artifact of the protein's location on the yeast cell surface.

Example 9: Comparison of the Fluorogenic Activity for a One-Domain scFv and a Two-Domain Hybrid scFv As described above, the MG fluorogen-activating protein H6-MG comprises a single $V_H$ domain, and the TO fluorogen-activating protein HL1-TO1 comprises a two-domain ($V_H$ and $V_L$) structure. The DNA for the $V_H$ domain of H6-MG was combined in vitro with the DNA for the $V_L$ domain of HL1-TO1 to form a fusion peptide construct of the two unrelated domains. This construct DNA was introduced into yeast and the protein product produced on the surface of the yeast as described above. The surface-expressed hybrid scFv construct was assayed for the ability to bind and activate MG fluorogen by FACS. The results are presented in FIG. 10, wherein "MG1" indicates the single $V_H$ domain of H6-MG, "scFv1" indicates the $V_L$ domain of HL1-TO1, and "HRV-3C" indicates human rhinovirus 3C protease.

Figure 10:
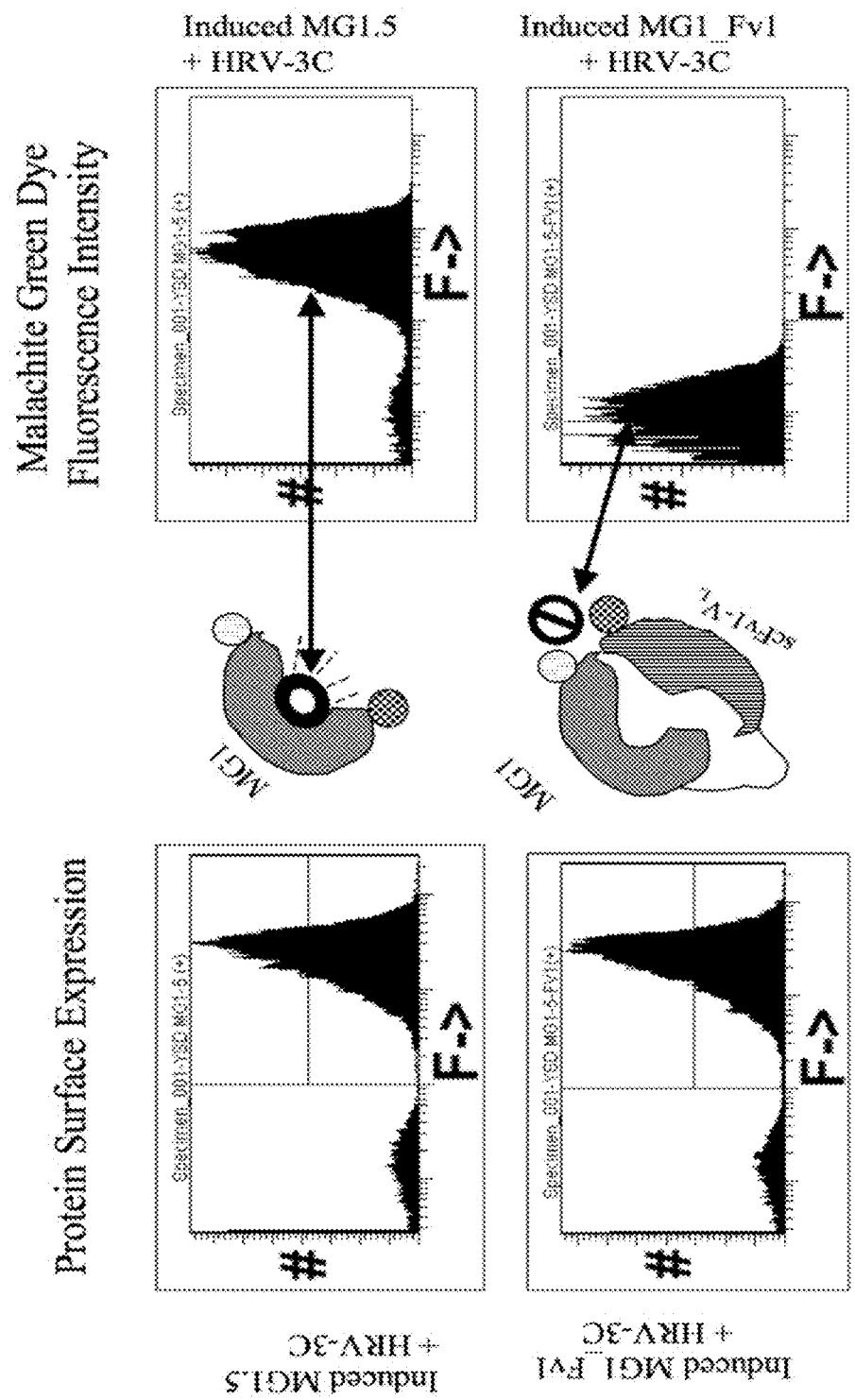
FIG. 10 presents semi-quantitative plots of cytometric data for single chain antibodies displayed on the surface of yeast; the plots on the left side of the Figure correspond to c-myc surface expression; the plots on the right side of the Figure correspond to fluorogen activity; the plots on the top half of the Figure correspond to a variable heavy single-domain antibody fragment (as illustrated in the accompanying diagram); and the plots on the bottom half of the Figure correspond to a hybrid blocked single chain antibody comprising the variable heavy single-domain antibody fragment (as illustrated in the accompanying diagram)

The left hand column of FACS data in FIG. 10 indicate that both the single $V_H$ domain of H6-MG and the hybrid H6-MG ($V_H$)/HL1-TO1($V_L$) construct are well expressed on the surface of yeast as determined by number of counts (area of the peak) in the P5 window, which correlates with the amount of c-myc epitope expressed on the surface of the yeast cells. The amount of MG fluorogen activation by the two different scFvs is shown by the counts between the $10^3$ and $2 \times 10^4$ units on the X-axis of the right-hand column of FACS data. The data indicate that while the single domain H6-MG scFv activates the MG fluorogen, the fluorogen is not activated by the hybrid H6-MG ($V_H$)/HL1-TO1($V_L$) construct (>99% inhibition). Accordingly, the hybrid H6-MG ($V_H$)/HL1-TO1($V_L$) construct is effectively blocked. The respective scFvs are illustrated by the diagrams presented between the two columns of FACS data (the diagrams match the respective plots of FACS data).

Example 10: Construction of a Blocked scFv Having an HRV-3C Protease Substrate

The DNA sequence coding for the peptide linker that covalently links the $V_H$ and $V_L$ domains in the blocked scFvs described in Example 9 was manipulated to add a DNA sequence (SEQ ID NO:10) that would code for the peptide sequence Leu-Glu-Val-Leu-Phe-Gln-Gly-Pro (SEQ ID NO:9). This peptide sequence is recognized and cleaved by the Human Rhinovirus 3C ("HRV-3C") protease between the Gln and Gly residues.

Figure 11A:
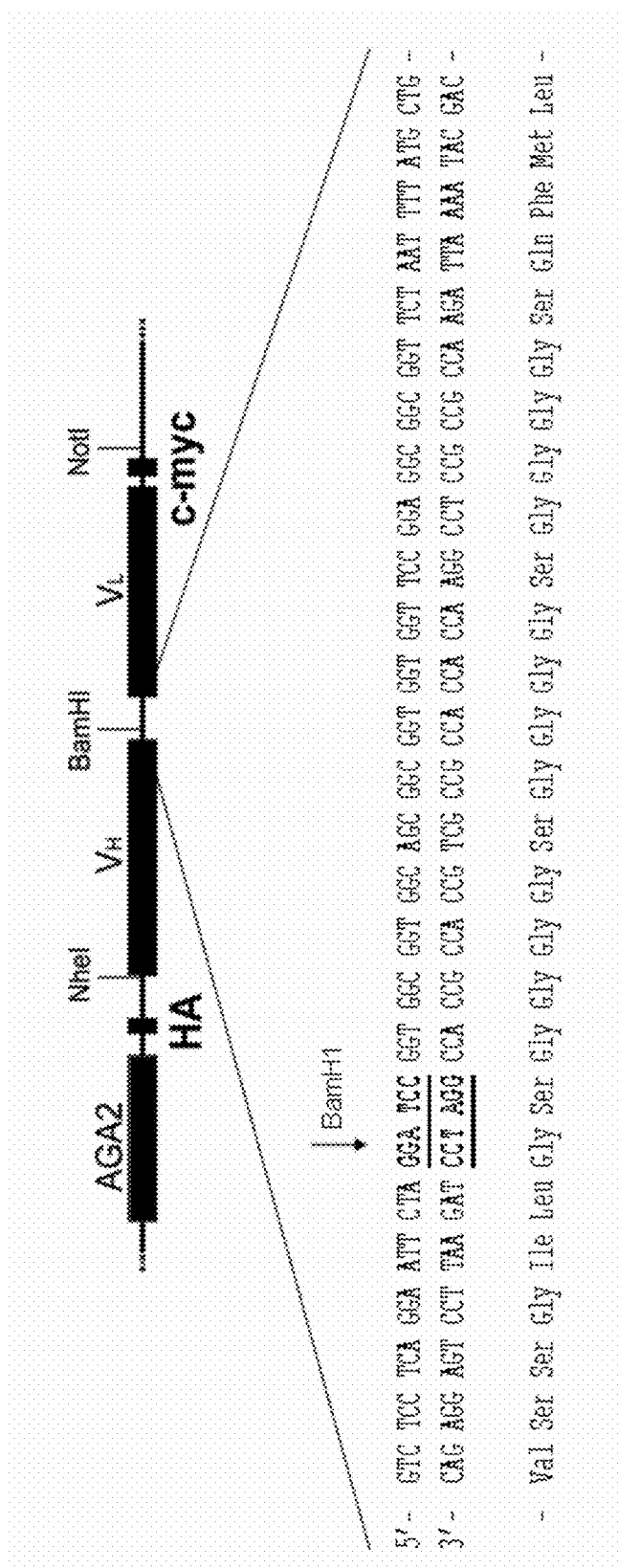
FIG. 11A presents a diagram depicting the nucleotide and amino acid sequences in a peptide linker region in a single chain antibody construct. The portion of the amino acid sequence depicted in FIG. 11A beginning with the third "Gly" and ending with the sixth "Ser" represents SEQ ID NO:1. The portion of the nucleotide sequence beginning with the first "GGT" and ending with "TCT" represents SEQ ID NO:2.
Figure 11B:
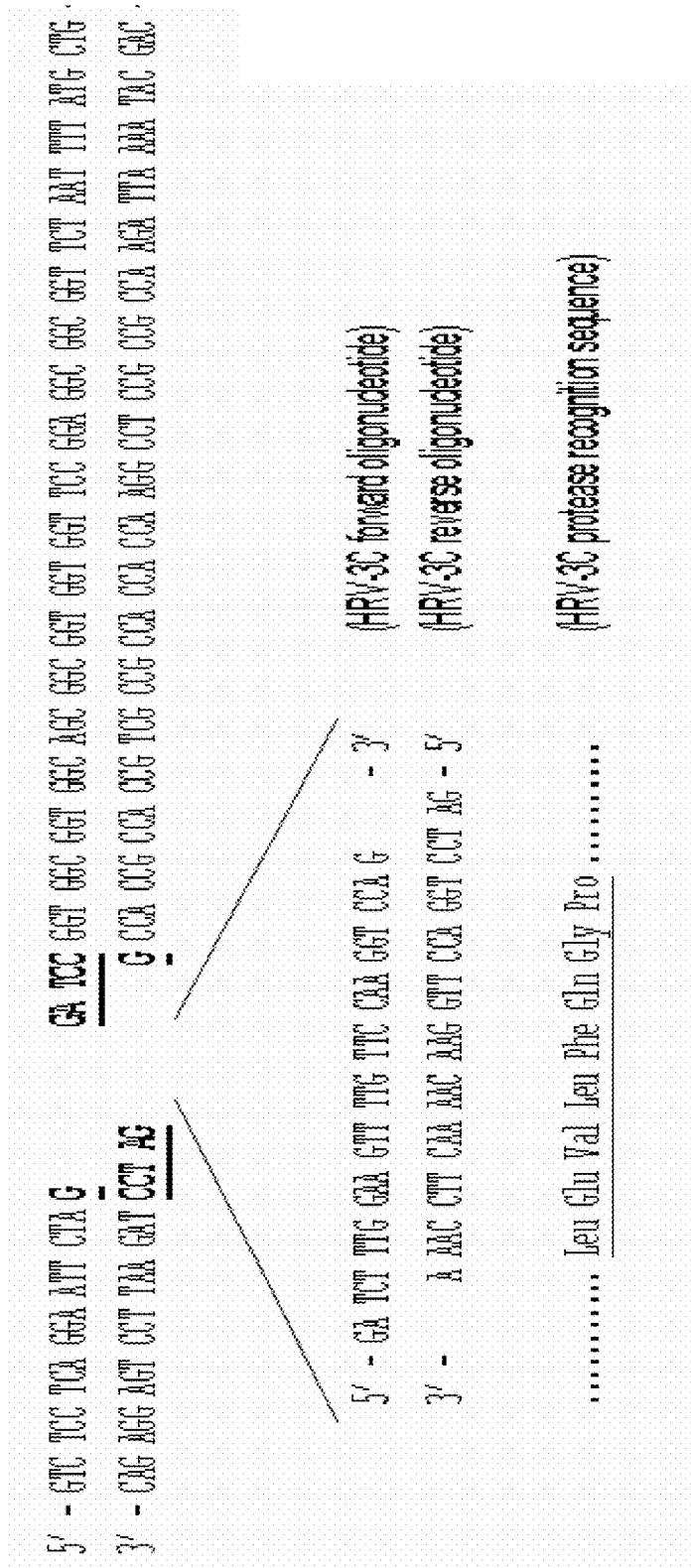
FIG. 11B presents a diagram detailing the cleavage of the DNA depicted in FIG. 11A by a restriction enzyme, and the ligation of an enzyme recognition sequence for HRV-3C protease into the peptide linker region.

The gene segment shown in FIG. 11A is part of the plasmid pPNL6. The plasmid pPNL6 was used to construct blocked scFvs as described above. The DNA encoding for the peptide linker segment connecting the $V_H$ and $V_L$ domains in the blocked scFvs comprised a recognition sequence that was cleaved by BamH1 restriction enzyme. In this example, the DNA comprised a 5'-GGA TCC-sequence and a 3'-CCT AGG-sequence, which was cleaved by BamH1 restriction enzyme as indicated in FIG. 11B.

A DNA segment coding for the peptide sequence Leu-Glu-Val-Leu-Phe-Gln-Gly-Pro and comprising BamH1 compatible ends was joined to the BamH1-cleaved plasmid using standard DNA ligation techniques known in the art. The two complementary DNA fragments encoding for the peptide sequence Leu-Glu-Val-Leu-Phe-Gln-Gly-Pro (i.e., the HRV-3C recognition sequence forward and reverse oligonucleotides) were synthesized and used to form duplex DNA using standard annealing techniques. The double stranded oligonucleotide was ligated into the cleaved plasmid in the peptide linker region. The modified DNA sequence (and expressed peptide) is illustrated in FIG. 11C. The resulting plasmid comprised a DNA sequence (SEQ ID NO:48) comprising an HRV-3C protease recognition sequence, which when expressed, resulted in a peptide construct (SEQ ID NO:47) comprising a fluorogen-activating peptide and a blocking peptide linked to the fluorogen-activating peptide through a peptide linker comprising an amino acid sequence that was specifically recognized as a modification substrate by a cognate enzyme, in this example HRV-3C protease.

Example 11: Fluorogenic Activity of a Blocked scFv Having a Protease Substrate

Figure 12:
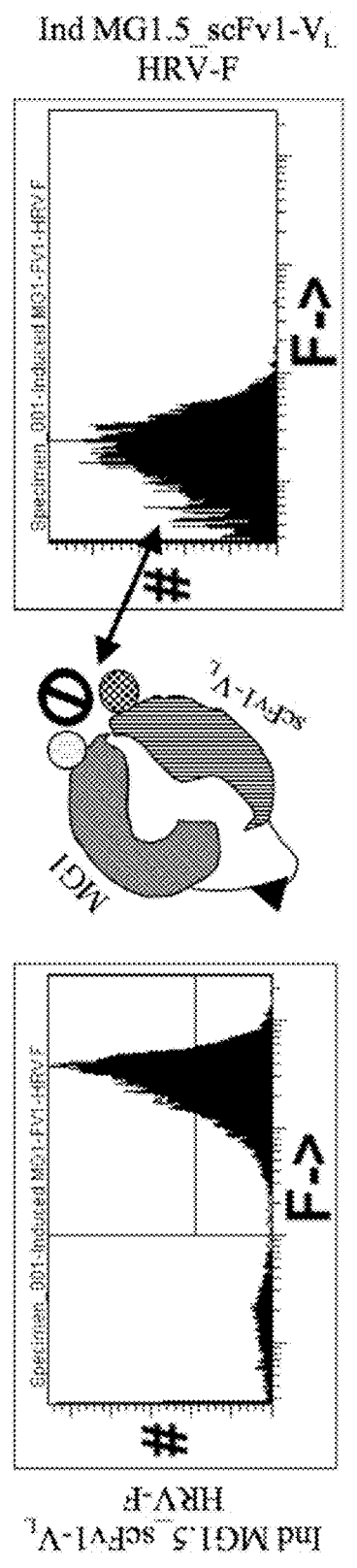

The scFv gene described in Example 10 (comprising SEQ ID NO:48) was introduced into yeast and the protein product expressed on the surface of yeast using the methods described above. The surface-displayed peptide constructs were assayed using FACS for the ability of the constructs to interact with and activate MG fluorogen. The results of the FACS analyses are shown in FIG. 12 (the plot on the left hand side corresponds to c-myc and the plot on the right hand side corresponds to fluorogen). A data analysis similar to that described in connection with FIG. 10, above, indicated that the scFv comprising the modified linker was still well expressed on the surface of the yeast (area of the peak in the P5 window in the left panel) and still fails to show fluorogenic activation of MG (lack of a peak between $10^3$ and $2 \times 10^4$ units on the X-axis of the plot in the right panel). The diagram between the two plots depicts the same domains as in FIG. 10 with the addition of the HRV-3C protease cleavage substrate.

Example 12: Fluorogenic Activity of a Blocked scFv Having a Protease Substrate and Treated with Protease Yeast cells comprising surface-displayed scFv comprising the modified linker described in Example 11 were assayed by FACS to determine surface expression of the peptide construct. The yeast cells were then treated with 1 unit of HRV-3C protease overnight at 4° C. and then re-assayed by FACS to quantify cleavage (indicated by the loss of c-myc epitope signal) and to quantify MG fluorescence activation. The results of the FACS analyses are shown in FIG. 13 (the plot on the left corresponds to c-myc and the plot on the right corresponds to fluorogen).

Figure 13:
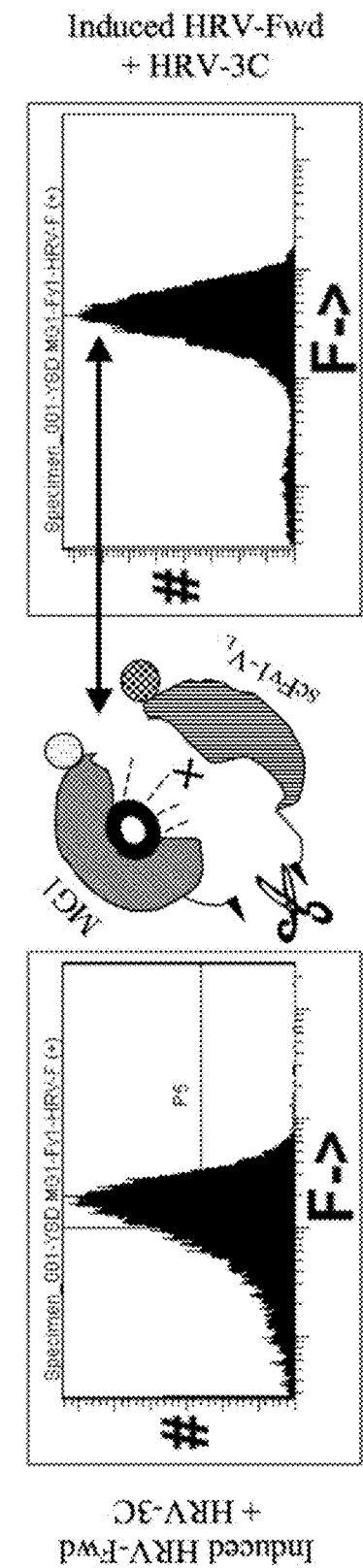
FIG. 13 presents semi-quantitative plots of cytometric data for a hybrid blocked single chain antibody having a protease recognition sequence spliced therein and treated with cognate protease as illustrated in the accompanying diagram.

Comparing the data presented in FIG. 12 with the data presented in FIG. 13 indicates that the majority of the c-myc epitope was cleaved off of the surface of the yeast (reduced area of the peak in the P5 window in the left panel) concomitant with a large fluorogenic activation of MG (shift of the peak to between $10^3$ and $2 \times 10^4$ units on the X-axis of the right-hand panel). The diagram between the two plots schematically depicts this data by showing the cleavage of the HRV-3C substrate, the dissociation of the two domains from each other, and the activation of the fluorogen molecule.

The peptide constructs produced in the above examples comprised a fluorogen-activating peptide (comprising H6-MG ($V_H$)) and a blocking peptide (comprising HL1-TO1 ($V_L$)) linked to the fluorogen-activating peptide through a peptide linker comprising an amino acid sequence that is specifically recognized as a cleavage substrate by an HRV-3C protease. The constructs find utility as biosensors for protease activity.

Example 13: Kinetic Analysis of Yeast Surface Displayed HRV-3C Biosensors

The potential for the biosensor described in Example 12 to be used as a real time assay for detecting the amount of protease in a sample was explored by evaluating the kinetics of fluorescence activation for the biosensor and other control constructs in a TECAN analytical fluorimeter. In these analyses, $10^6$ yeast cells expressing different scFv constructs on their cell surface were treated with 1 unit of HRV-3C protease at 25° C. All incubations were conducted in the presence of MG fluorogen. The ability of the constructs to activate MG fluorescence was measured over a period of 2 hours.

Figure 14:
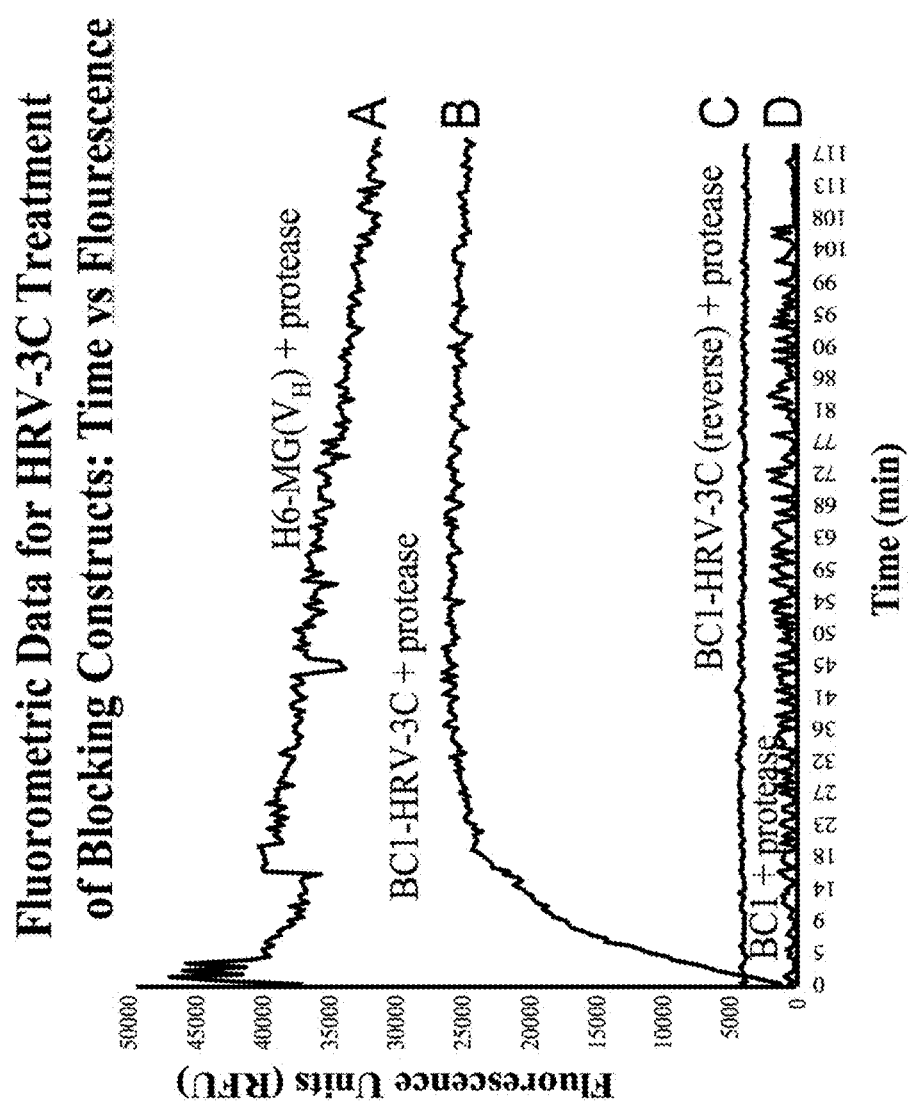
FIG. 14 is a graph presenting the results of a kinetic protease assay for an HRV-3C protease biosensor according to an embodiment disclosed herein.

FIG. 14 shows the data for this kinetic assay of the activation of the HRV-3C protease biosensor. Line B is the activation curve for the biosensor described in Example 12. Activation of the biosensor is complete by 30 minutes of incubation. The fluorescence signal plateaus for the remainder of the assay time. The length of time to reach the plateau may be used as a measure of the protease concentration. Line C is the response of the same blocked construct when a different amino acid sequence (which is not a protease substrate) of the same length was inserted into the peptide linker. There was no change in activity upon treatment with HV-3C protease. Line D is the activation profile of the "blocked construct" without any added amino acid sequence in the peptide linker There was a very small signal that did not change with time. Line A is the signal of the active single-domain H6-MG $V_H$ domain expressed on the surface of yeast.

Example 14: Construction of a Blocked scFv Having a Caspase 3 Protease Substrate The DNA sequence coding for the peptide linker that covalently links the $V_H$ and $V_L$ domains in the blocked scFvs described in Example 9 was manipulated to add a DNA sequence (SEQ ID NO:14) that would code for the peptide sequence Asp-Glu-Val-Asp (SEQ ID NO:13). This peptide sequence is recognized and cleaved by caspase 3 protease.

Figure 15:
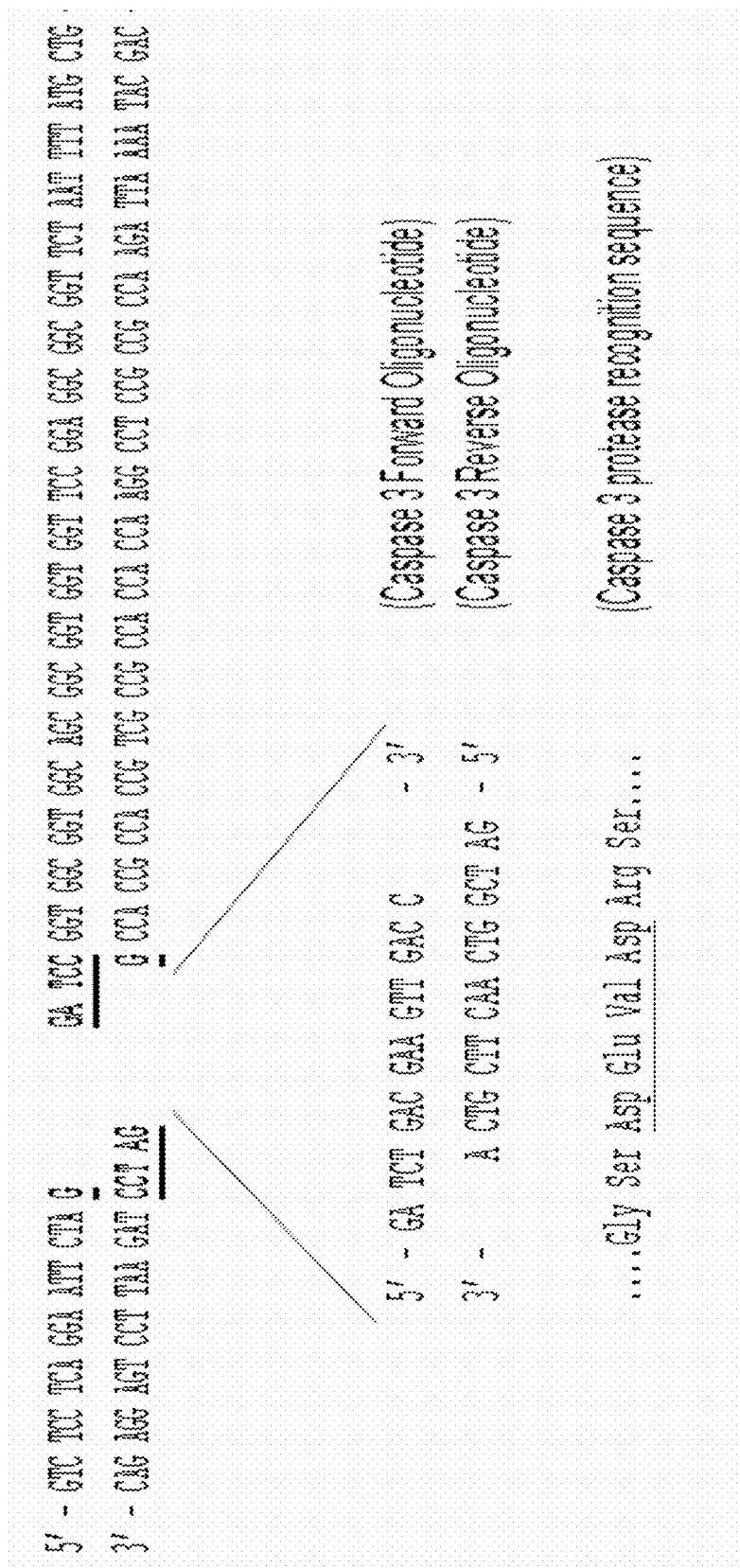
FIG. 15 presents a diagram depicting the nucleotide sequence for a peptide linker region in a single chain antibody construct, and detailing the cleavage of the DNA by a restriction enzyme and the ligation of an enzyme recognition sequence for Caspase 3 protease into the peptide linker region. The portion of the forward oligonucleotide sequence beginning with the first "GAC" and ending with the second "GAC" represents the Caspase 3 protease recognition sequence, SEQ ID NO:14. The portion of the amino acid sequence beginning with the first "Asp" and ending with the second "Asp" represents the Caspase 3 protease recognition sequence, SEQ ID NO:13.

The plasmid pPNL6 was used to construct blocked scFvs as described above. The DNA encoding for the peptide linker segment connecting the $V_H$ and $V_L$ domains in the blocked scFvs comprised a recognition sequence that was cleaved by BamH1 restriction enzyme. In this example, the DNA comprised a 5'-GGA TCC-sequence and a 3'-CCT AGG-sequence, which was cleaved by BamH1 restriction enzyme as indicated in FIG. 15.

A DNA segment coding for the peptide sequence Asp-Glu-Val-Asp and comprising BamH1 compatible ends was joined to the BamH1-cleaved plasmid using standard DNA ligation techniques known in the art. The resulting plasmid comprised a DNA sequence (SEQ ID NO:52) comprising a caspase 3 protease recognition sequence, which when expressed, resulted in a peptide construct (SEQ ID NO:51) comprising a fluorogen-activating peptide and a blocking peptide linked to the fluorogen-activating peptide through a peptide linker comprising an amino acid sequence that is specifically recognized as a modification substrate by a cognate enzyme, in this example caspase 3 protease.

The peptide constructs produced in this example comprised a fluorogen-activating peptide (comprising H6-MG ($V_H$)) and a blocking peptide (comprising HL1-TO1 ($V_L$)) linked to the fluorogen-activating peptide through a peptide linker comprising an amino acid sequence that was specifically recognized as a cleavage substrate by caspase 3 protease. The constructs find utility as biosensors for protease activity.

Example 15: Kinetic Analysis of Yeast Surface Displayed Caspase 3 Biosensors The potential for the biosensor described in Example 14 to be used as a real time assay for detecting the amount of protease in a sample was explored by evaluating the kinetics of fluorescence activation for the biosensor and other control constructs in a TECAN analytical fluorimeter. In these analyses, $10^6$ yeast cells expressing different scFv constructs on their cell surface were treated with 1 unit of caspase 3 protease at 25° C. All incubations were conducted in the presence of MG fluorogen. The ability of the constructs to activate MG fluorescence was measured over a period of 2 hours.

Figure 16:
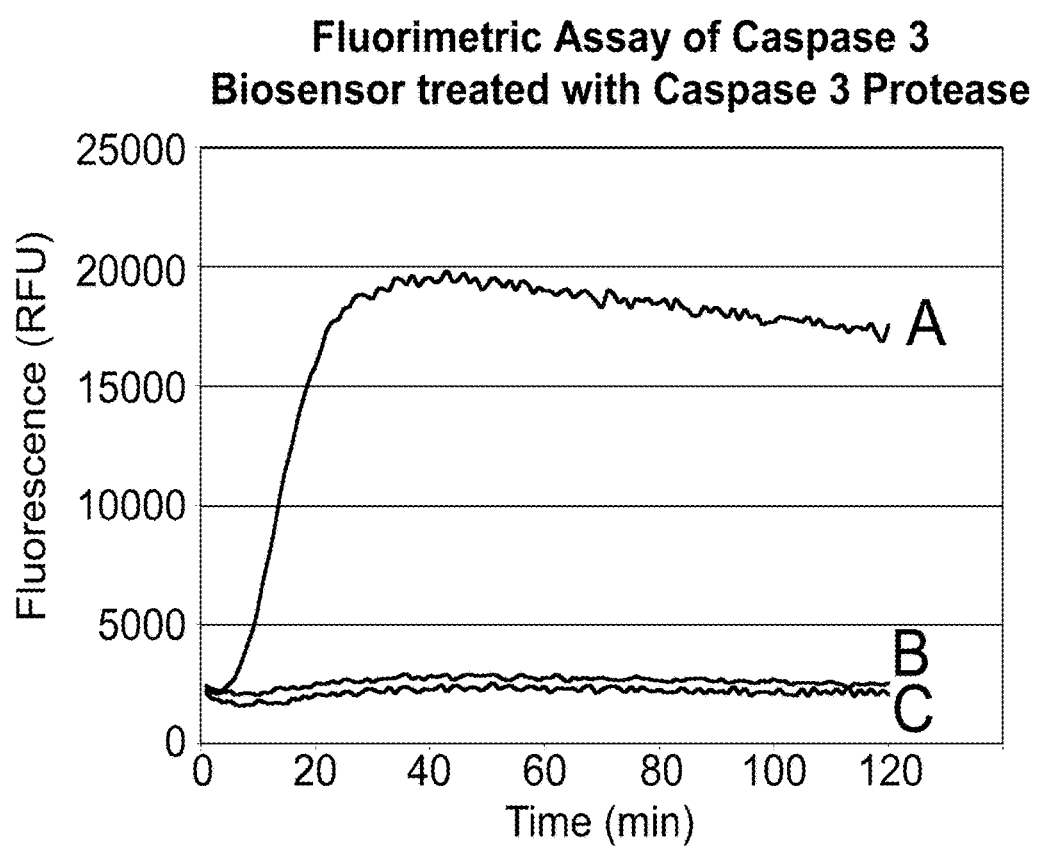
FIG. 16 is a graph presenting the results of a kinetic protease assay for a caspase 3 protease biosensor according to an embodiment disclosed herein.

FIG. 16 shows the data for this kinetic assay of the activation of the caspase 3 protease biosensor. Line A is the activation curve for the biosensor described in Example 14. Activation of the biosensor is complete by 30 minutes of incubation. The fluorescence signal plateaus for the remainder of the assay time. The length of time to reach the plateau may be used as a measure of the protease concentration. Line B is the activation profile of the biosensor in the absence of caspase 3 protease. Line C is the activation profile of the "blocked construct" without any added amino acid sequence in the peptide linker.

Example 16: Isolation and Purification of Caspase 3 Biosensors

Figure 17:
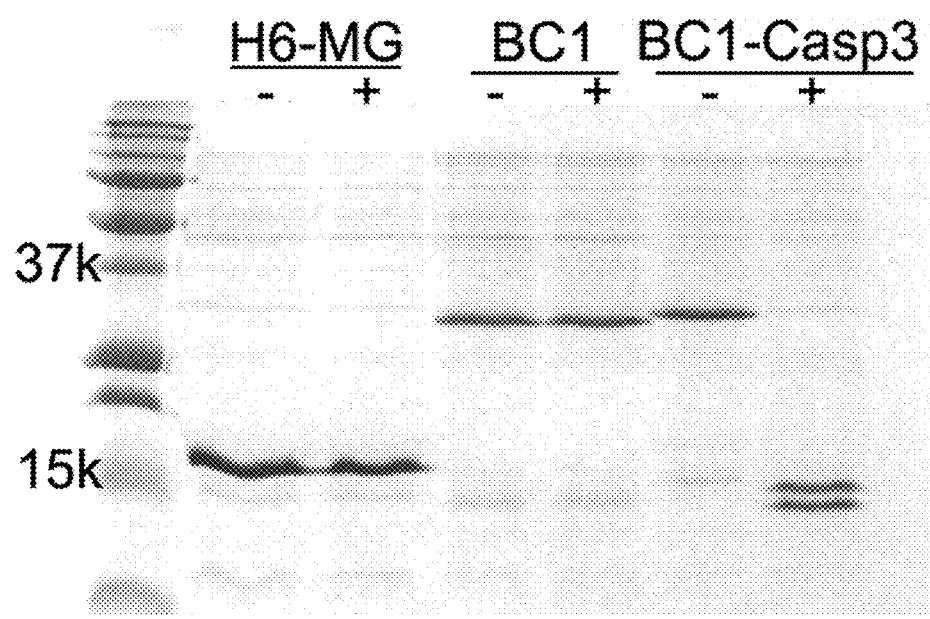
FIG. 17 is photograph of an SDS gel of a single-domain antibody comprising a variable heavy chain domain fragment (H6-MG), a blocked hybrid scFv comprising the variable heavy chain domain fragment (BC1), and a caspase 3 protease biosensor construct comprising the variable heavy chain domain fragment according to an embodiment disclosed herein.

Caspase 3 biosensors as described in Example 14 were isolated and purified as described in Example 7. 1 µg of single-domain active $V_H$, 1 µg of blocked scFv without modified peptide linker, and 1 µg of purified biosensor were respectively mixed with 1 unit of caspase 3 or buffer solution and incubated overnight at 4° C. The proteins were run on an 18% SDS gel and stained with coomasie blue. A photograph of the gel is presented in FIG. 17 ("H6-MG" indicates single domain $V_H$, "BC1" indicates a blocked peptide construct without a recognition sequence inserted into the peptide linker, and "BC1-Casp3" indicates the active biosensor construct; (−) indicates incubation with buffer alone, and (+) indicates incubation with caspase 3 protease).

Example 17: In Vivo Stability and Functionality of Caspase 3 Biosensors

Figure 18:
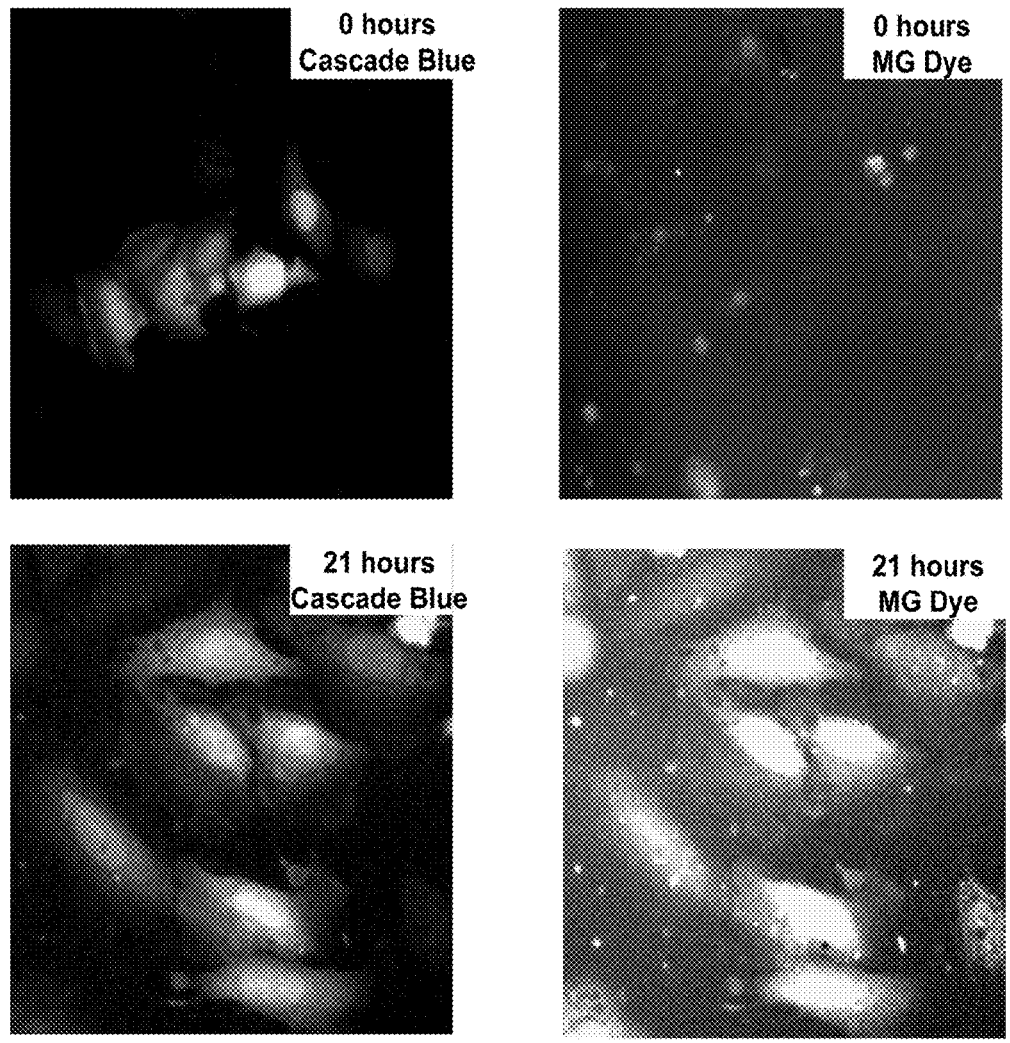
FIG. 18 presents microscopy images of HeLa cells injected with Cascade Blue dextran tracking solution containing isolated and purified biosensors according to an embodiment disclosed herein.

The in vivo stability and functionality of isolated and purified caspase 3 biosensors as described in Example 16 were evaluated. HeLa cells were injected with Cascade Blue dextran tracking solution comprising 12 mg/ml biosensor and 10 µg MG fluorogen. The cells were treated with 10 µg/ml etoposide. Microscopy images were acquired in both the blue and MG channels immediately after injection and at 21 hours post-injection. Representative microscopy images are presented in FIG. 18.

Example 18: Construction of an HRV-3C Protease Biosensor

Figure 19:
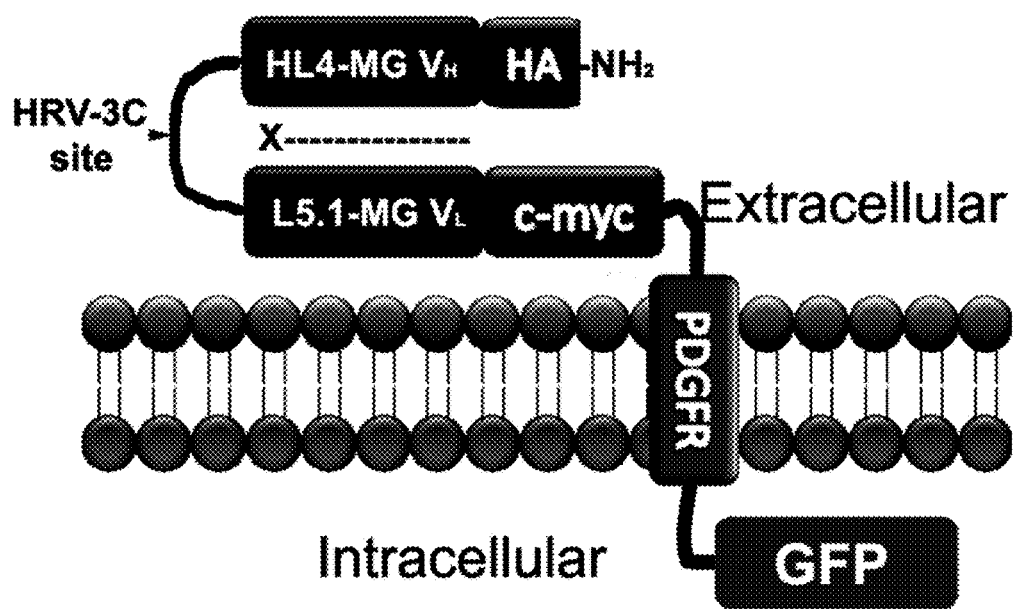
FIG. 19 is a diagram depicting a transmembrane fused HRV-3C protease biosensor according to an embodiment disclosed herein.

A membrane-bound biosensor was constructed in a pBabe-Sac-Lac retroviral vector using genetic engineering methods known in the art. The fluorogen-activating peptide of the biosensor comprised the L5.1-MG $V_L$ domain and the blocking peptide of the biosensor comprised the HL4-MG $V_H$ domain (Example 6). The peptide linker was modified as described in Example 10 to include an HRV-3C protease recognition site. NIH 3T3 cells were transduced with the retroviral vector expressing the HRV-3C biosensor using genetic engineering methods known in the art. The biosensor is illustrated in FIG. 19. The biosensor is positioned extracellularly, connected to green fluorescent protein ("GFP") through a transmembrane PFGER peptide.

Figure 20:
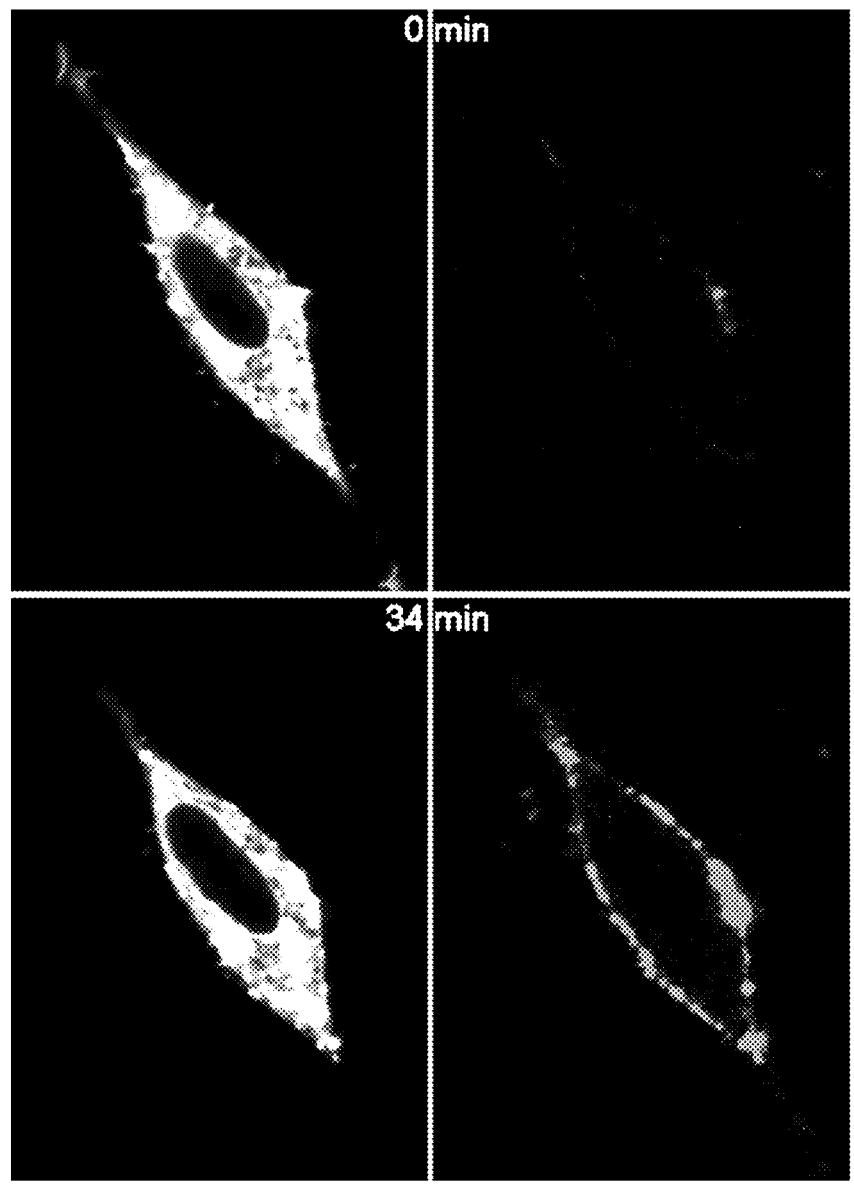
FIG. 20 presents microscopy images of NIH 3T3 cells transduced with a retroviral vector expressing the HRV-3C biosensor as illustrated in FIG. 18.

The NIH T3T cells expressing the biosensor-GFP fusion protein construct were treated with HRV-3C protease. Microscopy images were acquired in both the GFP channel and MG channel immediately after contact and after 34 minutes incubation. Representative microscopy images are presented in FIG. 20 (left panels in GFP channel, right panels in MG channel).

Example 19: Construction of a Caspase 1 Protease Biosensor

The DNA sequence coding for the peptide linker that covalently links the $V_H$ and $V_L$ domains in the blocked scFvs described in Example 9 was manipulated to add a DNA sequence (SEQ ID NO:12) that would code for the peptide sequence Tyr-Val-Ala-Asp (SEQ ID NO:11). This peptide sequence is recognized and cleaved by caspase 1 protease.

Figure 21:
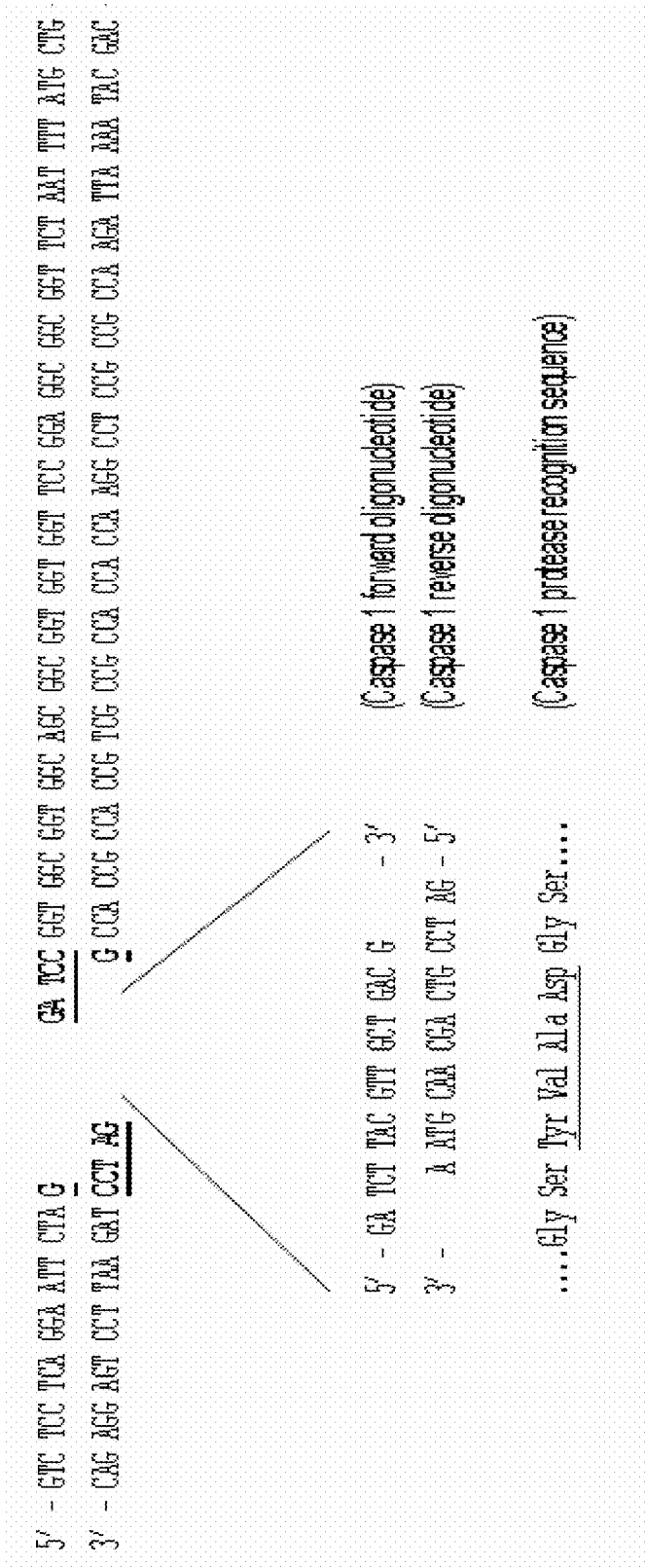
FIG. 21 presents a diagram depicting the nucleotide sequence for a peptide linker region in a single chain antibody construct, and detailing the cleavage of the DNA by a restriction enzyme and the ligation of an enzyme recognition sequence for Caspase 1 protease into the peptide linker region. The portion of the forward oligonucleotide sequence beginning with the nucleotides "TAC" and ending with "GAC" represents the Caspase 1 protease recognition sequence, SEQ ID NO:12. The portion of the amino acid sequence beginning with the amino acid "Tyr" and ending with "Asp" represents the Caspase 1 protease recognition sequence, SEQ ID NO: 11.

The plasmid pPNL6 was used to construct blocked scFvs as described above. The DNA encoding for the peptide linker segment connecting the $V_H$ and $V_L$ domains in the blocked scFvs comprised a recognition sequence that was cleaved by BamH1 restriction enzyme. In this example, the DNA comprised a 5'-GGA TCC-sequence and a 3'-CCT AGG-sequence, which was cleaved by BamH1 restriction enzyme as indicated in FIG. 21.

A DNA segment coding for the peptide sequence Tyr-Val-Ala-Asp and comprising BamH1 compatible ends was joined to the BamH1-cleaved plasmid using standard DNA ligation techniques known in the art. The resulting plasmid comprised a DNA sequence (SEQ ID NO:50) comprising a caspase 1 protease recognition sequence, which when expressed, resulted in a peptide construct (SEQ ID NO:49) comprising a fluorogen-activating peptide and a blocking peptide linked to the fluorogen-activating peptide through a peptide linker comprising an amino acid sequence that is specifically recognized as a modification substrate by a cognate enzyme, in this example caspase 1 protease.

The peptide constructs produced in this example comprise a fluorogen-activating peptide (comprising H6-MG ($V_H$)) and a blocking peptide (comprising HL1-TO1 ($V_L$)) linked to the fluorogen-activating peptide through a peptide linker comprising an amino acid sequence that is specifically recognized as a modification substrate by a protease. The constructs may find utility as biosensors for protease activity.

Example 20: Construction of a TEV Protease Biosensor

The DNA sequence coding for the peptide linker that covalently links the $V_H$ and $V_L$ domains in the blocked scFvs described in Example 9 is manipulated to add a DNA sequence (SEQ ID NO:8) that would code for the peptide sequence Glu-Asn-Leu-Tyr-Phe-Gln-Gly (SEQ ID NO:7). This peptide sequence is recognized and cleaved by TEV protease.

Figure 22:
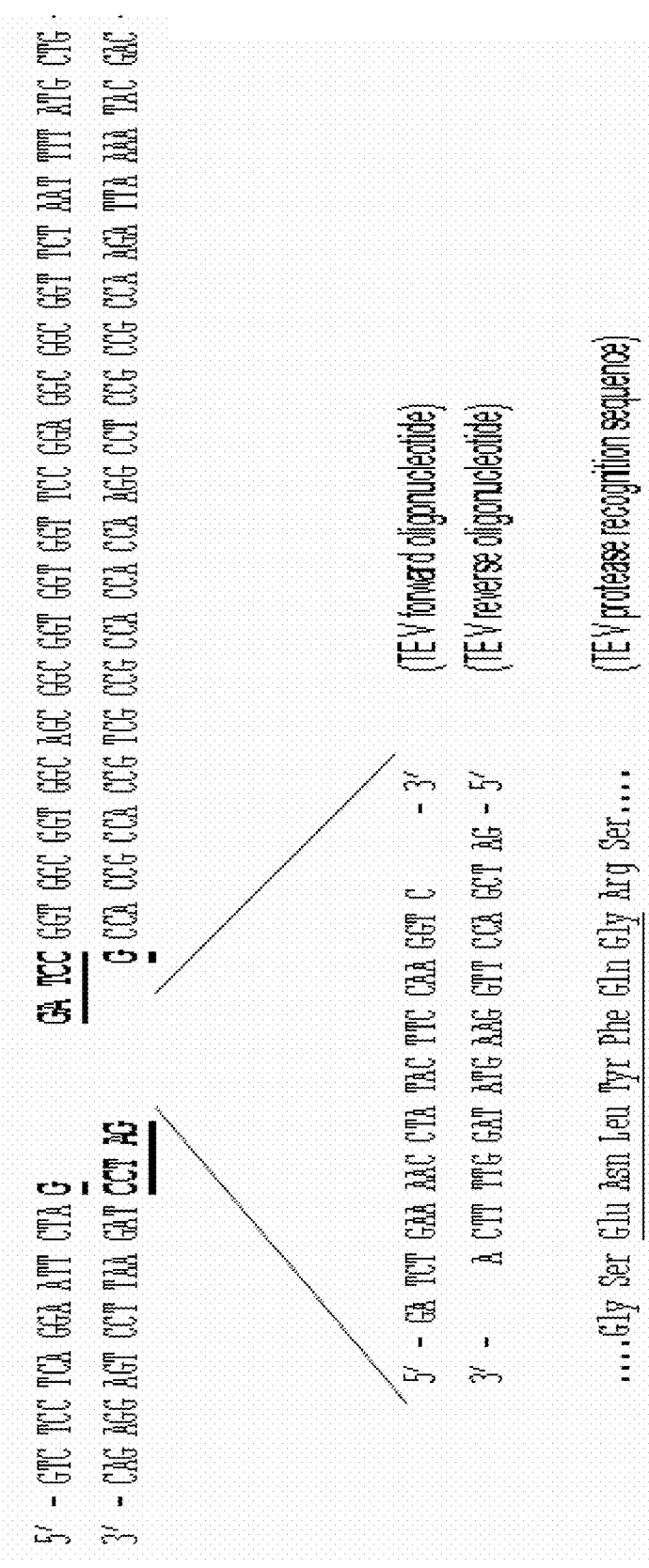
FIG. 22 presents a diagram depicting the nucleotide sequence for a peptide linker region in a single chain antibody construct, and detailing the cleavage of the DNA by a restriction enzyme and the ligation of an enzyme recognition sequence for TEV protease into the peptide linker region. The portion of the forward oligonucleotide sequence beginning with the nucleotides "GAA" and ending with "GGT" represents the TEV protease recognition sequence, SEQ ID NO:8. The portion of the amino acid sequence beginning with the amino acid "Glu" and ending with the second "Gly" represents the TEV protease recognition sequence, SEQ ID NO:7.

The plasmid pPNL6 is used to construct blocked scFvs as described above. The DNA encoding for the peptide linker segment connecting the $V_H$ and $V_L$ domains in the blocked scFvs comprises a recognition sequence that is cleaved by BamH1 restriction enzyme. In this example, the DNA comprised a 5'-GGA TCC-sequence and a 3'-CCT AGG-sequence, which is cleaved by BamH1 restriction enzyme as indicated in FIG. 22.

A DNA segment coding for the peptide sequence Glu-Asn-Leu-Tyr-Phe-Gln-Gly and comprising BamH1 compatible ends is joined to the BamH1-cleaved plasmid using standard DNA ligation techniques known in the art. The resulting plasmid comprises a DNA sequence (SEQ ID NO:46) comprising a TEV protease recognition sequence, which when expressed, results in a peptide construct (SEQ ID NO:45) comprising a fluorogen-activating peptide and a blocking peptide linked to the fluorogen-activating peptide through a peptide linker comprising an amino acid sequence that is specifically recognized as a modification substrate by a cognate enzyme, in this example TEV protease.

Peptide constructs produced according to this example comprise a fluorogen-activating peptide (comprising H6-MG $V_H$ domain) and a blocking peptide (comprising HL1-TO1 $V_L$ domain) linked to the fluorogen-activating peptide through a peptide linker comprising an amino acid sequence that is specifically recognized as a modification substrate by a protease. The constructs may find utility as biosensors for protease activity.

Example 21: Construction of a Furin Protease Biosensor

The DNA sequence coding for the peptide linker that covalently links the $V_H$ and $V_L$ domains in the blocked scFvs described in Example 9 was manipulated to add a DNA sequence (SEQ ID NO:4) that would code for the peptide sequence Arg-Lys-Lys-Arg-Ser (furin short recognition sequence) (SEQ ID NO:3). This peptide sequence is recognized and cleaved by furin protease.

Figure 23:
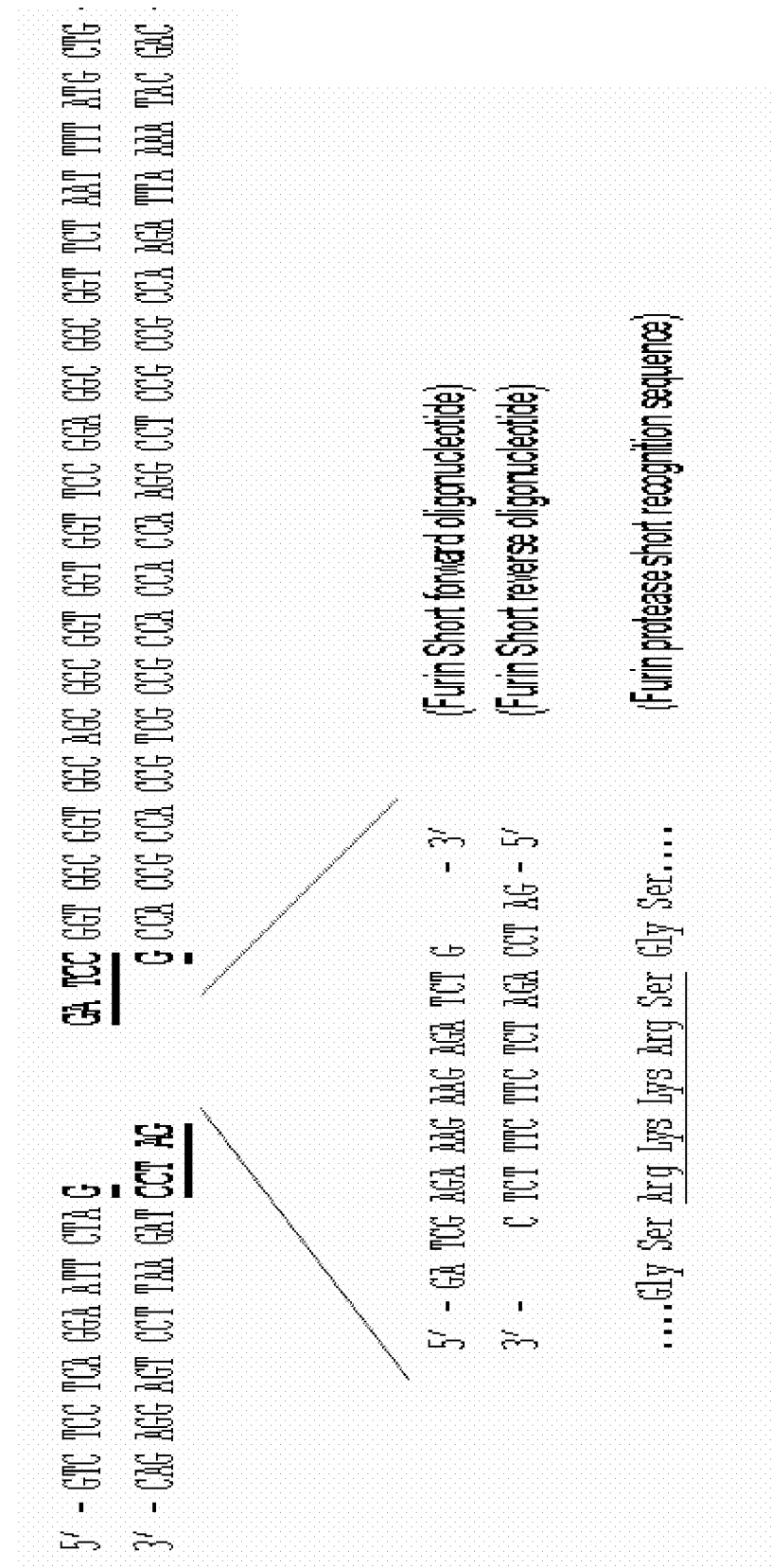
FIG. 23 presents a diagram depicting the nucleotide sequence for a peptide linker region in a single chain antibody construct, and detailing the cleavage of the DNA by a restriction enzyme and the ligation of an enzyme short recognition sequence for furin protease into the peptide linker region. The portion of the forward oligonucleotide sequence beginning with the first "AGA" and ending with "TCT" represents the Furin protease short recognition sequence, SEQ ID NO:4. The portion of the amino acid sequence beginning with the first "Arg" and ending with the second "Ser" represents the Furin protease short recognition sequence, SEQ ID NO:3.

The plasmid pPNL6 was used to construct blocked scFvs as described above. The DNA encoding for the peptide linker segment connecting the $V_H$ and $V_L$ domains in the blocked scFvs comprised a recognition sequence that was cleaved by BamH1 restriction enzyme. In this example, the DNA comprised a 5'-GGA TCC-sequence and a 3'-CCT AGG-sequence, which is cleaved by BamH1 restriction enzyme as indicated in FIG. 23.

A DNA segment coding for the peptide sequence Arg-Lys-Lys-Arg-Ser and comprising BamH1 compatible ends was joined to the BamH1-cleaved plasmid using standard DNA ligation techniques known in the art. The resulting plasmid comprised a DNA sequence (SEQ ID NO:42) comprising a furin protease short recognition sequence, which when expressed, resulted in a peptide construct (SEQ ID NO:41) comprising a fluorogen-activating peptide and a blocking peptide linked to the fluorogen-activating peptide through a peptide linker comprising an amino acid sequence that was specifically recognized as a modification substrate by a cognate enzyme, in this example furin protease.

The peptide constructs produced in this example comprised a fluorogen-activating peptide (comprising H6-MG $V_H$ domain) and a blocking peptide (comprising HL1-TO1 $V_L$ domain) linked to the fluorogen-activating peptide through a peptide linker comprising an amino acid sequence that was specifically recognized as a modification substrate by a protease. The constructs find utility as biosensors for furin protease activity.

Example 22: Construction of a Furin Protease Biosensor

The DNA sequence coding for the peptide linker that covalently links the $V_H$ and $V_L$ domains in the blocked scFvs described in Example 9 was manipulated to add a DNA sequence (SEQ ID NO:6) that would code for the peptide sequence Asn-Ser-Arg-Lys-Lys-Arg-Ser-Thr-Ser-Ala (furin long recognition sequence) (SEQ ID NO:5). This peptide sequence is recognized and cleaved by furin protease.

Figure 24:
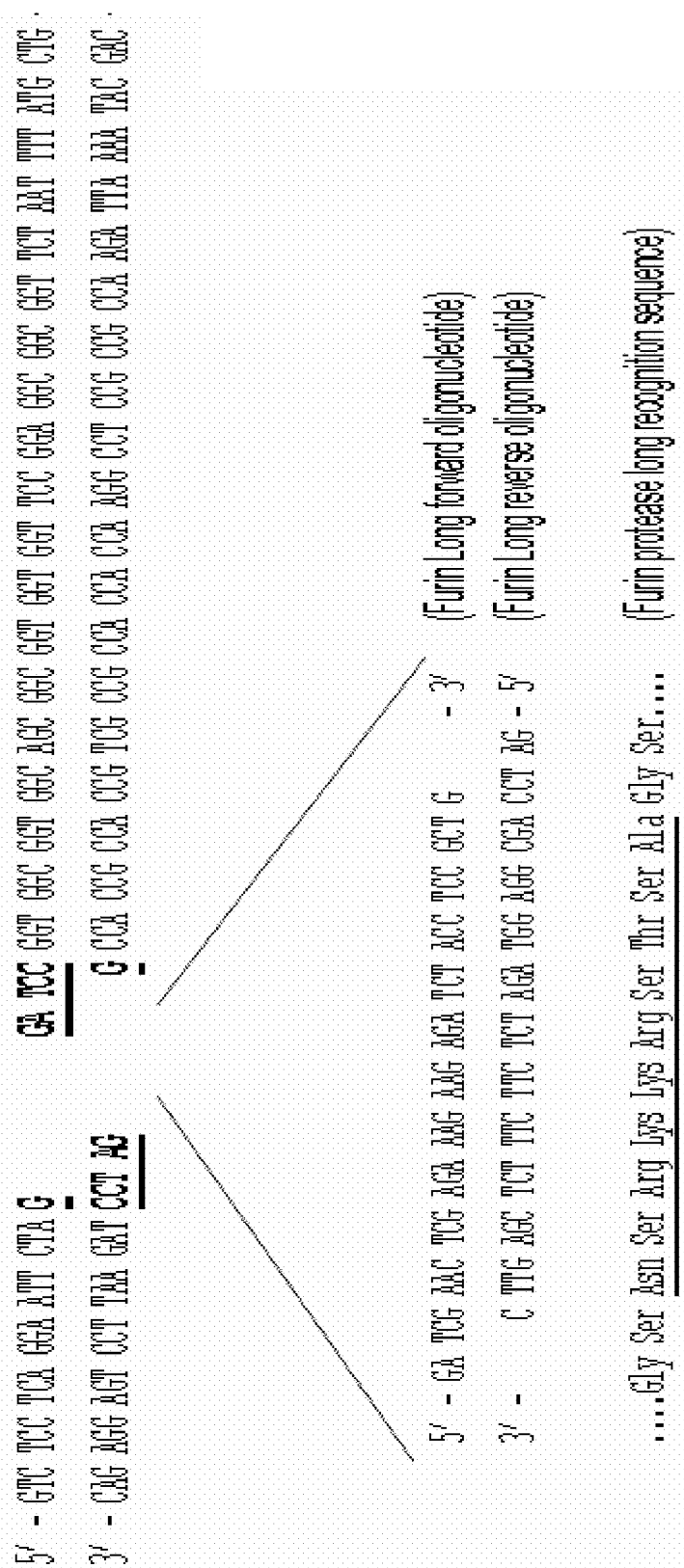
FIG. 24 presents a diagram depicting the nucleotide sequence for a peptide linker region in a single chain antibody construct, and detailing the cleavage of the DNA by a restriction enzyme and the ligation of an enzyme long recognition sequence for furin protease into the peptide linker region. The portion of the forward oligonucleotide sequence beginning with "AAC" and ending with "GCT" represents the Furin protease long recognition sequence, SEQ ID NO:6. The portion of the amino acid sequence beginning with "Asn" and ending with "Ala" represents the Furin protease long recognition sequence, SEQ ID NO:5.

The plasmid pPNL6 was used to construct blocked scFvs as described above. The DNA encoding for the peptide linker segment connecting the $V_H$ and $V_L$ domains in the blocked scFvs comprised a recognition sequence that was cleaved by BamH1 restriction enzyme. In this example, the DNA comprised a 5'-GGA TCC-sequence and a 3'-CCT AGG-sequence, which was cleaved by BamH1 restriction enzyme as indicated in FIG. 24.

A DNA segment coding for the peptide sequence Asn-Ser-Arg-Lys-Lys-Arg-Ser-Thr-Ser-Ala and comprising BamH1 compatible ends was joined to the BamH1-cleaved plasmid using standard DNA ligation techniques known in the art. The resulting plasmid comprised a DNA sequence (SEQ ID NO:44) comprising a furin protease long recognition sequence, which when expressed, resulted in a peptide construct (SEQ ID NO:43) comprising a fluorogen-activating peptide and a blocking peptide linked to the fluorogen-activating peptide through a peptide linker comprising an amino acid sequence that was specifically recognized as a modification substrate by a cognate enzyme, in this example furin protease.

The peptide constructs produced in this example comprised a fluorogen-activating peptide (comprising H6-MG $V_H$ domain) and a blocking peptide (comprising HL1-TO1 $V_L$ domain) linked to the fluorogen-activating peptide through a peptide linker comprising an amino acid sequence that was specifically recognized as a modification substrate by a protease. The constructs find utility as biosensors for furin protease activity.

Example 23: Isolation and Purification of Furin Biosensors

Figure 25:
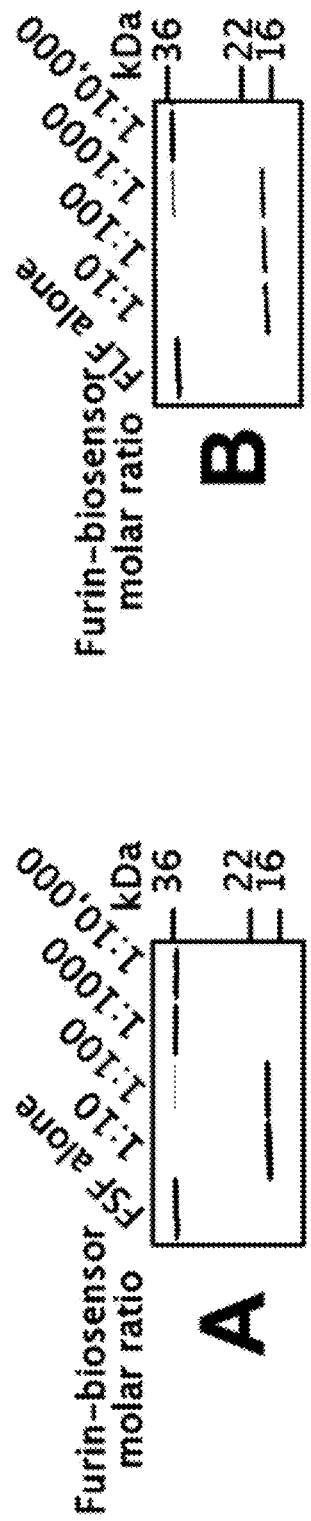
FIG. 25 presents SDS gels for purified and soluble furin in protease biosensors treated with furin in the indicated molar ratios.

Furin biosensors as described in Examples 21 and 22 were isolated and purified as described in Example 7. The biosensors comprising the short furin recognition sequence ("FSF") (Example 21) and the long furin recognition sequence ("FLF") (Example 22) were respectively mixed with purified furin protease under conditions suitable for enzymatic activity (100 mM HEPES buffer pH 7.5, 1 mM $CaCl_2$, 1 mM beta-mercaptoethanol, for 1 hour at 37° C.) in the following molar ratios: 1:10; 1:100; 1:1000; 1:10000. Coomasie blue stained SDS polyacrylamide electrophoresis gels of the purified furin biosensors treated with furin are presented in FIG. 25 (gel A corresponds to FSF; gel B corresponds to FLF).

Referring to FIG. 25A (FSF), the biosensor without furin treatment was not cleaved, as was expected. Cleavage of the biosensors was complete or nearly complete at 1:10 and 1:100 mixture ratios. The two proteolytic fragments of the biosensor were so close in size that they were not resolved on the SDS gel system. The biosensor was not cleaved at 1:1000 and 1:10000 mixture ratios.

Referring to FIG. 25B (FLF), the biosensor was stable when not contacted with furin. Cleavage of the sensor was complete at ratios of 1:10, 1:100, and 1:1000. No cleavage was apparent at the 1:10000 ratio.

Example 24: Kinetic Analysis of Isolated and Purified Furin Biosensors

Figure 26:
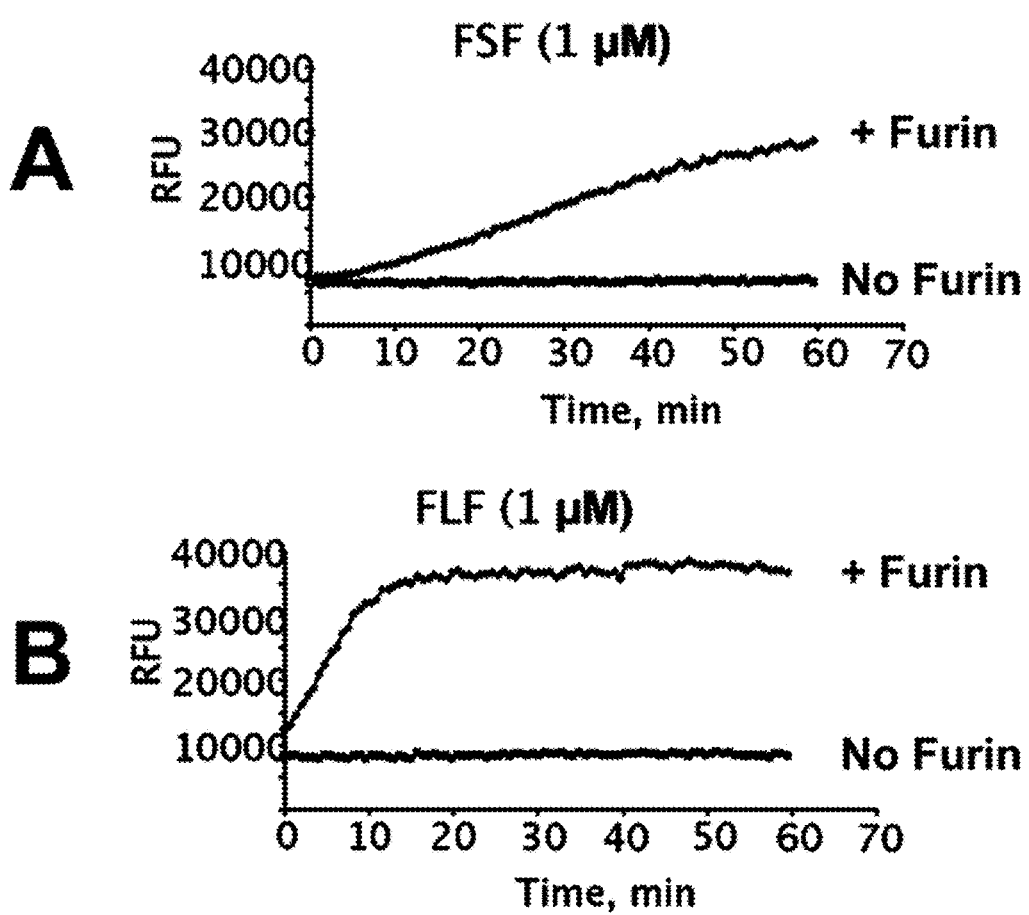
FIG. 26 presents graphs presenting the results of kinetic protease assays for purified and soluble furin protease biosensors according to an embodiment disclosed herein.

The potential for the biosensors described in Example 23 to be used as a real time assay for detecting the amount of furin protease in a sample was explored by evaluating the kinetics of fluorescence activation for the biosensor in a BioTek Synergy HT Fluorimeter (excitation at 590 nm, emission recorded at 645 nm, the gain (PMT) was 150). 1 µM of short sequence furin biosensor and 1 µM of long sequence furin biosensor were respectively incubated with 0.01 µM furin in 100 mM HEPES pH 7.5, 1 mM $CaCl_2$, 1 mM beta-mercaptoethanol, 0.1% w/v Pluronic F127, and 100 nM MG fluorogen, for 1 hour at room temperature. FIG. 26 shows the data for the kinetic assays of the activation of the furin protease biosensors (top curves represent biosensor treated with furin, bottom curves represent biosensors without furin contact).

Example 25: Construction of an MMP Protease Biosensor

The DNA sequence coding for the peptide linker that covalently links the $V_H$ and $V_L$ domains in the blocked scFvs described in Example 9 was manipulated to add a DNA sequence (SEQ ID NO:16) that would code for the peptide sequence Val-Met-Arg-Leu-Val-Val (SEQ ID NO:15). This peptide sequence is recognized and cleaved by MMP25 protease.

Figure 27:
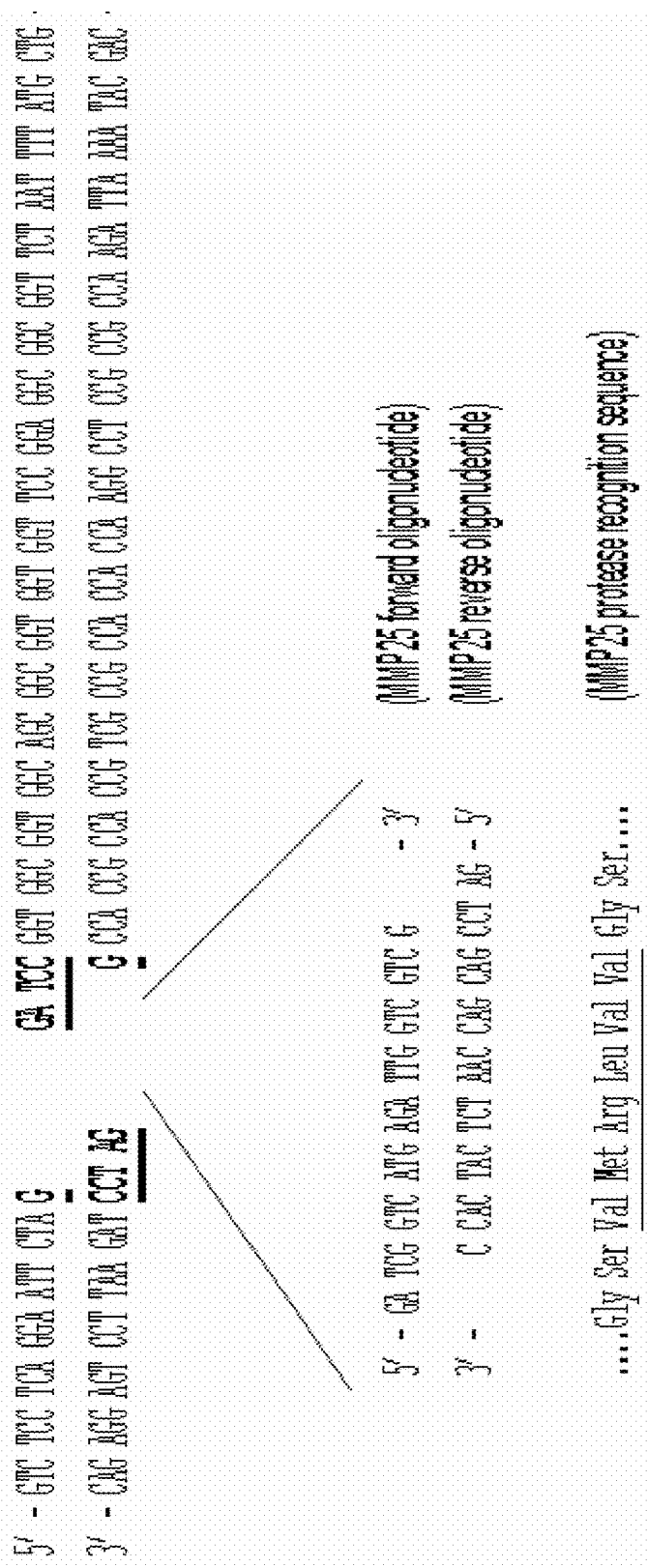
FIG. 27 presents a diagram depicting the nucleotide sequence for a peptide linker region in a single chain antibody construct, and detailing the cleavage of the DNA by a restriction enzyme and the ligation of an enzyme recognition sequence for MMP25 protease into the peptide linker region. The portion of the forward oligonucleotide sequence beginning with the first "GTC" and ending with the third "GTC" represents the MMP25 protease recognition sequence, SEQ ID NO:16. The portion of the amino acid sequence beginning with the first "Val" and ending with the third "Val" represents the MMP25 protease recognition sequence, SEQ ID NO:15.

The plasmid pPNL6 was used to construct blocked scFvs as described above. The DNA encoding for the peptide linker segment connecting the $V_H$ and $V_L$ domains in the blocked scFvs comprised a recognition sequence that was cleaved by BamH1 restriction enzyme. In this example, the DNA comprised a 5'-GGA TCC-sequence and a 3'-CCT AGG-sequence, which was cleaved by BamH1 restriction enzyme as indicated in FIG. 27.

A DNA segment coding for the peptide sequence Val-Met-Arg-Leu-Val-Val and comprising BamH1 compatible ends was joined to the BamH1-cleaved plasmid using standard DNA ligation techniques known in the art. The resulting plasmid comprised a DNA sequence (SEQ ID NO:54) comprising a MMP25 protease recognition sequence, which when expressed, resulted in a peptide construct (SEQ ID NO:53) comprising a fluorogen-activating peptide and a blocking peptide linked to the fluorogen-activating peptide through a peptide linker comprising an amino acid sequence that is specifically recognized as a modification substrate by a cognate enzyme, in this example MMP25 protease.

The peptide constructs produced according to this example comprised a fluorogen-activating peptide (comprising H6-MG $V_H$ domain) and a blocking peptide (comprising HL1-TO1 $V_L$ domain) linked to the fluorogen-activating peptide through a peptide linker comprising an amino acid sequence that is specifically recognized as a cleavage substrate by MMP25 protease. The constructs may find utility as biosensors for protease activity.

Example 26: Construction of a PKA Biosensor

The DNA sequence coding for the peptide linker that covalently links the $V_H$ and $V_L$ domains in the blocked scFvs described herein is manipulated to add a DNA sequence (SEQ ID NO:18) that codes for the peptide sequence Leu-Leu-Arg-Arg-Ala-Ser-Leu-Gly-Pro (SEQ ID NO:17). This peptide sequence is recognized and phosphorylated by PKA.

Figure 28:
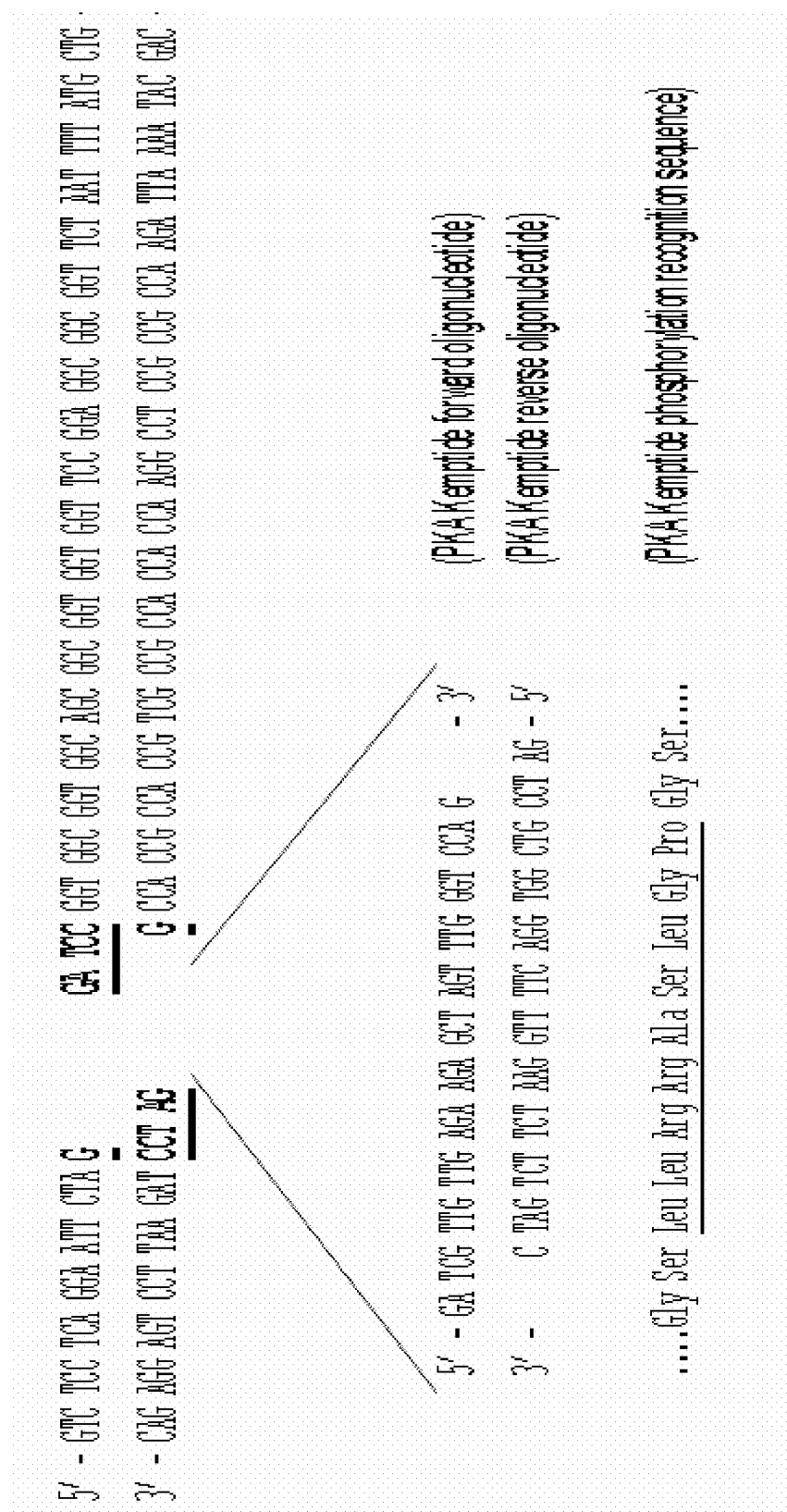
FIG. 28 presents a diagram depicting the nucleotide sequence for a peptide linker region in a single chain antibody construct, and detailing the cleavage of the DNA by a restriction enzyme and the ligation of an enzyme recognition sequence for protein kinase A (PKA Kemptide phosphorylation) into the peptide linker region. The portion of the forward oligonucleotide sequence beginning with the first "TTG" and ending with "CCA" represents the PKA Kemptide phosphorylation recognition sequence, SEQ ID NO:18. The portion of the amino acid sequence beginning with the first "Leu" and ending with "Pro" represents the PKA Kemptide phosphorylation recognition sequence, SEQ ID NO:17.

The plasmid pPNL6 is used to construct blocked scFvs as described above. The DNA encoding for the peptide linker segment connecting the $V_H$ and $V_L$ domains in the blocked scFvs comprises a recognition sequence that is cleaved by BamH1 restriction enzyme. In this example, the DNA comprises a 5'-GGA TCC-sequence and a 3'-CCT AGG-sequence, which may be cleaved by BamH1 restriction enzyme as indicated in FIG. 28.

A DNA segment coding for the peptide sequence Leu-Leu-Arg-Arg-Ala-Ser-Leu-Gly-Pro (SEQ ID NO: 17) and comprising BamH1 compatible ends is joined to the BamH1-cleaved plasmid using standard DNA ligation techniques known in the art. The resulting plasmid comprises a DNA sequence (e.g., SEQ ID NO:56) comprising a PKA recognition sequence, which when expressed, results in a peptide construct (e.g., SEQ ID NO:55) comprising a fluorogen-activating peptide and a blocking peptide linked to the fluorogen-activating peptide through a peptide linker comprising an amino acid sequence that is specifically recognized as a modification substrate by a cognate enzyme, in this example PKA.

Peptide constructs produced according to this example comprise a fluorogen-activating peptide and a blocking peptide linked to the fluorogen-activating peptide through a peptide linker comprising an amino acid sequence that is specifically recognized as a phosphorylation substrate by PKA. The constructs may find utility as biosensors for phosphorylation activity.

Example 27: Construction of a PKA Biosensor

A PKA biosensor as described in Example 26 is modified to further comprise 14-3-3τ peptide covalently linked to the C-terminal end of the biosensor. The biosensor may comprise a fluorogen-activating peptide comprising the L5.1-MG $V_L$ domain and a blocking peptide comprising the HL4-MG $V_H$ domain. The L5.1-MG $V_L$ domain and the HL4-MG $V_H$ domain are linked through a peptide linker comprising a (Gly$_4$Ser)$_3$ sequence and a Leu-Leu-Arg-Arg-Ala-Ser-Leu-Gly-Pro sequence (SEQ ID NO: 17) such that the L5.1-MG $V_L$ domain is on the C-terminal end of the peptide construct and the HL4-MG $V_H$ domain is on the N-terminal end of the peptide construct.

Figure 29:
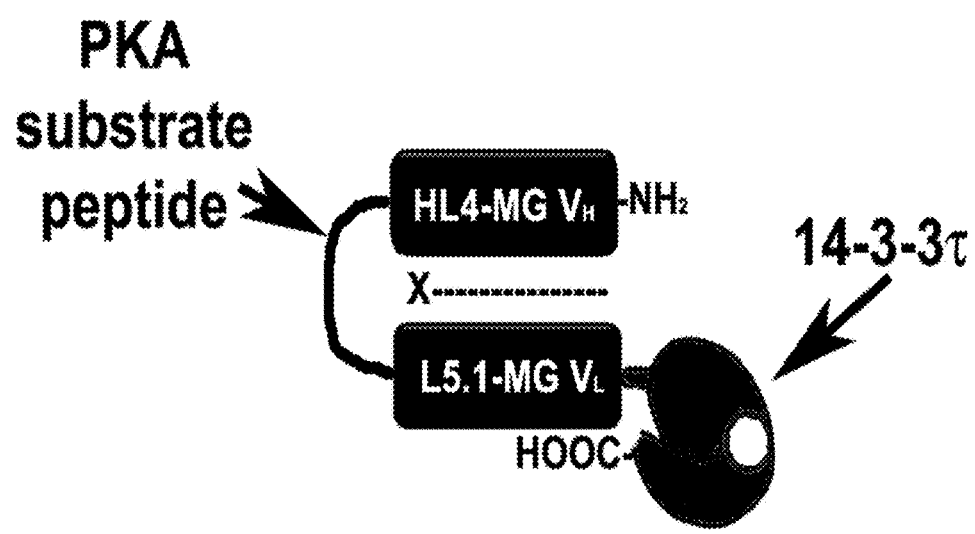
FIG. 29 is a diagram illustrating a protein kinase A biosensor according to an embodiment disclosed herein.

The plasmid comprising the DNA coding for the biosensor is cut using appropriate restriction enzymes after the DNA sequence coding for the L5.1-MG $V_L$ domain. A DNA sequence coding for 14-3-3τ peptide is ligated into the plasmid such that when expressed, the resulting protein construct comprises a 14-3-3τ peptide on the C-terminal end of the L5.1-MG $V_L$ domain. A peptide construct produced according to this example is illustrated in FIG. 29.

Peptide constructs produced according to this example comprise a fluorogen-activating peptide and a blocking peptide linked to the fluorogen-activating peptide through a peptide linker comprising an amino acid sequence that is specifically recognized as a phosphorylation substrate by PKA. The 14-3-3τ peptide may complex with the peptide linker when it is phosphorylated by PKA. The constructs may find utility as biosensors for phosphorylation activity.

Example 28: Construction of a Biosensor to Detect H3-K56 Acetylation Activity

The DNA sequence coding for the peptide linker that covalently links the $V_H$ and $V_L$ domains in the blocked scFvs described herein is manipulated to add a DNA sequence (SEQ ID NO:20) that codes for the peptide sequence Ile-Arg-Arg-Phe-Gln-Lys-Ser-Thr-Asp-Leu-Leu (SEQ ID NO:19). This peptide sequence is recognized and acetylated by H3-K56 acetyltransferase.

Figure 30:
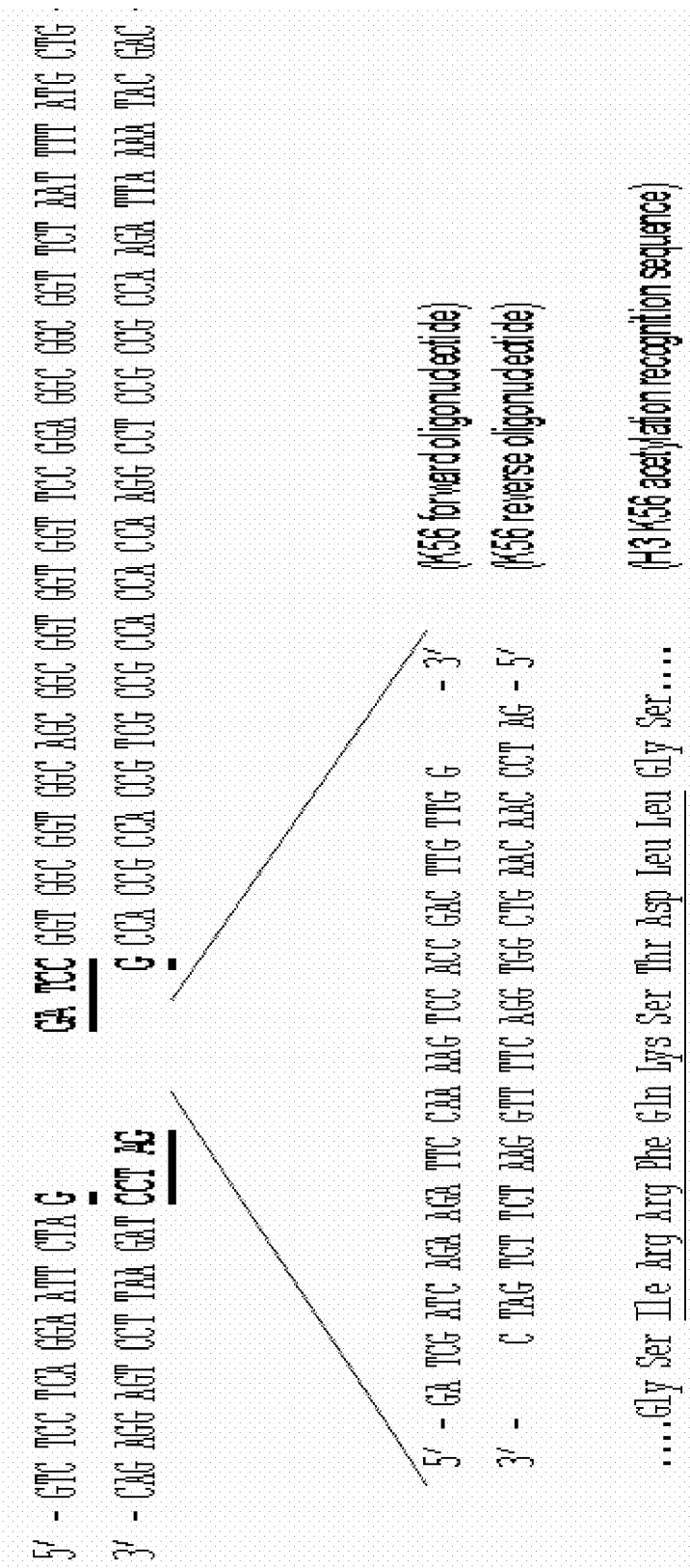
FIG. 30 presents, a diagram depicting the nucleotide sequence for a peptide linker region in a single chain antibody construct, and detailing the cleavage of the DNA by a restriction enzyme and the ligation of an enzyme recognition sequence for an acetyltransferase that acetylates certain lysine residues in histone H3 into the peptide linker region. The portion of the forward oligonucleotide sequence beginning with "ATC" and ending with the second "TTG" represents the H3-K56 acetylation recognition sequence, SEQ ID NO:20. The portion of the amino acid sequence beginning with "Ile" and ending with the second "Leu" represents the H3-K56 acetylation recognition sequence, SEQ ID NO:19.

The plasmid pPNL6 is used to construct blocked scFvs as described above. The DNA encoding for the peptide linker segment connecting the $V_H$ and $V_L$ domains in the blocked scFvs comprises a recognition sequence that is cleaved by BamH1 restriction enzyme. In this example, the DNA comprises a 5'-GGA TCC-sequence and a 3'-CCT AGG-sequence, which is cleaved by BamH1 restriction enzyme as indicated in FIG. 30.

A DNA segment coding for the peptide sequence Ile-Arg-Arg-Phe-Gln-Lys-Ser-Thr-Asp-Leu-Leu (SEQ ID NO:19) and comprising BamH1 compatible ends is joined to the BamH1-cleaved plasmid using standard DNA ligation techniques known in the art. The resulting plasmid comprises a DNA sequence (e.g., SEQ ID NO:58) comprising a H3-K56 acetyltransferase recognition sequence, which when expressed, results in a peptide construct (e.g., SEQ ID NO:57) comprising a fluorogen-activating peptide and a blocking peptide linked to the fluorogen-activating peptide through a peptide linker comprising an amino acid sequence that is specifically recognized as a modification substrate by a cognate enzyme, in this example H3-K56 acetyltransferase.

Peptide constructs produced according to this example comprise a fluorogen-activating peptide and a blocking peptide linked to the fluorogen-activating peptide through a peptide linker comprising an amino acid sequence that is specifically recognized as an acetylation substrate by H3-K56 acetyltransferase. The constructs may find utility as biosensors for acetylation activity.

Example 29: Construction of a Biosensor to Detect H3-K56 Acetylation Activity

A H3-K56 acetyltransferase biosensor as described in Example 28 is modified to further comprise bromo-domain peptide covalently linked to the C-terminal end of the biosensor. The biosensor may comprise a fluorogen-activating peptide comprising the L5.1-MG $V_L$ domain and a blocking peptide comprising the HL4-MG $V_H$ domain. The L5.1-MG $V_L$ domain and the HL4-MG $V_H$ domain are linked through a peptide linker comprising a (Gly$_4$Ser)$_3$ sequence and a Ile-Arg-Arg-Phe-Gln-Lys-Ser-Thr-Asp-Leu-Leu sequence (SEQ ID NO:19) such that the L5.1-MG $V_L$ domain is on the C-terminal end of the peptide construct and the HL4-MG $V_H$ domain is on the N-terminal end of the peptide construct.

Figure 31:
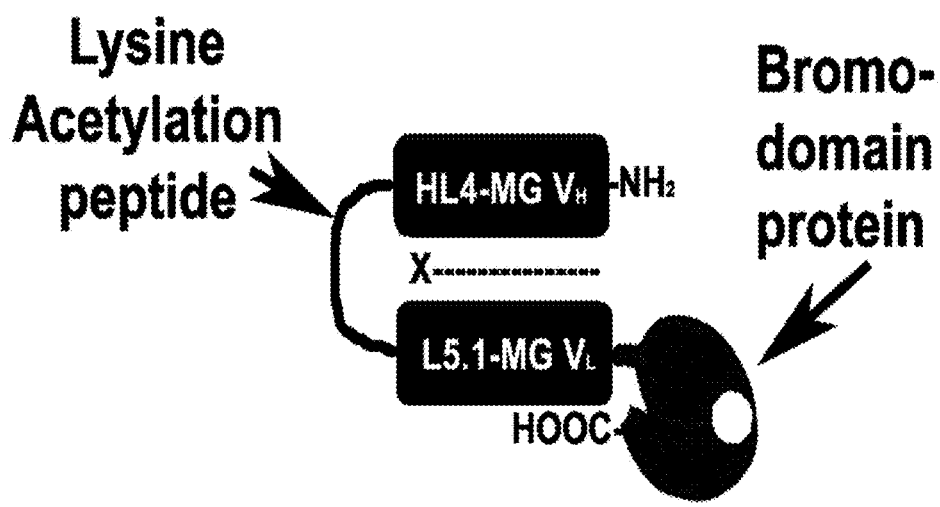
FIG. 31 is diagram illustrating an H3 K56 acetyltransferase biosensor according to an embodiment disclosed herein.

The plasmid comprising the DNA coding for the biosensor is cut using appropriate restriction enzymes after the DNA sequence coding for the L5.1-MG $V_L$ domain. A DNA sequence coding for bromo-domain peptide is ligated into the plasmid such that when expressed, the resulting protein construct comprises a bromo-domain peptide on the C-terminal end of the L5.1-MG $V_L$ domain. A peptide construct produced according to this example is illustrated in FIG. 31.

Peptide constructs produced according to this example comprise a fluorogen-activating peptide and a blocking peptide linked to the fluorogen-activating peptide through a peptide linker comprising an amino acid sequence that is specifically recognized as an acetylation substrate by H3-K56 acetyltransferase. The bromo-domain peptide may complex with the peptide linker when it is acetylated by H3-K56 acetyltransferase. The constructs may find utility as biosensors for acetylation activity.

Embodiments within the scope of the invention described herein may include the following.

A biosensor comprising a fluorogen-activating peptide having an active domain; and a blocking peptide linked to the fluorogen-activating peptide, wherein one of the fluorogen-activating peptide and the blocking peptide comprises a variable heavy chain domain of an antibody and the other peptide comprises a variable light chain domain of a different antibody.

A biosensor comprising a fluorogen-activating peptide having an active domain; and a blocking peptide linked to the fluorogen-activating peptide through a peptide linker comprising an amino acid sequence that is specifically recognized as a modification substrate by a cognate enzyme, wherein the blocking peptide associates with the fluorogen-activating peptide thereby blocking an active domain of the fluorogen-activating peptide when the peptide linker is unmodified, and wherein the fluorogen-activating peptide and the blocking peptide at least partially disassociate when the linker is modified by a cognate enzyme, thereby allowing the fluorogen-activating peptide to interact with a cognate fluorogen and modulate a fluorescence signal. In this embodiment of a biosensor, the fluorogen-activating peptide may comprise a variable heavy chain domain of an antibody and the blocking peptide may comprise a variable light chain domain of a different antibody. Alternatively, the fluorogen-activating peptide may comprise a variable light chain domain of an antibody and the blocking peptide may comprise a variable heavy chain domain of a different antibody.

In any of the embodiments of biosensors described herein, the fluorogen-activating peptide may specifically bind to a cognate fluorogen. The cognate fluorogen may be selected from the group consisting of thiazole orange, malachite green, dimethyl indole red, and derivatives thereof.

In various embodiments of the biosensors described herein, the peptide linker may comprise an amino acid sequence that is specifically recognized as a cleavage substrate by a cognate protease, wherein the fluorogen-activating peptide and the blocking peptide at least partially disassociate when the linker is cleaved by a cognate protease, thereby allowing the fluorogen-activating peptide to interact with a cognate fluorogen and modulate a fluorescence signal. The peptide linker may comprise an amino acid sequence specifically recognized as a cleavage substrate by a protease. The linker may comprise an amino acid sequence specifically recognized as a cleavage substrate by furin, and may for example, comprise an amino acid sequence comprising the sequence Arg-Xaa-(Arg/Lys)-Arg, such as Arg-Lys-Lys-Arg-Ser (SEQ ID NO: 3), or Asn-Ser-Arg-Lys-Lys-Arg-Ser-Thr-Ser-Ala (SEQ. ID NO: 5). The linker may comprise an amino acid sequence specifically recognized as a cleavage substrate by matrix metalloproteinase 25, and may for example, comprise an amino acid sequence comprising the sequence Val-Met-Arg-Leu-Val-Val (SEQ. ID NO: 15). The linker may comprise an amino acid sequence specifically recognized as a cleavage substrate by human rhinovirus protease 3C, and may for example comprise an amino acid sequence comprising the sequence Leu-Glu-Val-Leu-Phe-Gln-Gly-Pro (SEQ. ID NO: 9). The linker may comprise an amino acid sequence specifically recognized as a cleavage substrate by a caspase, and may for example comprise an amino acid sequence specifically recognized as a cleavage substrate by caspase 1, such as Tyr-Ala-Val-Asp (SEQ. ID NO: 11). The linker may comprise an amino acid sequence specifically recognized as a cleavage substrate by caspase 3, and may for example comprise an amino acid sequence comprising the sequence Asp-Glu-Val-Asp (SEQ. ID NO: 13). The linker may comprise an amino acid sequence specifically recognized as a cleavage substrate by TEV protease, and may for example, comprises an amino acid sequence comprising the sequence Glu-Asn-Leu-Tyr-Phe-Gln-Gly (SEQ. ID NO: 7). The peptide linker may comprise an amino acid sequence that is specifically recognized as a phosphorylation substrate by a cognate protein kinase. For example, such a linker may comprise an amino acid sequence specifically recognized by protein kinase A as a phosphorylatable peptide sequence, such as the sequence Leu-Leu-Arg-Arg-Ala-Ser-Leu-Gly-Pro (SEQ. ID NO: 17). For example, such a linker may comprise a phospho(amino acid) binding peptide linked to the fluorogen-activating peptide or the blocking peptide, such as the 14-3-3τ domain. The linker may comprise an amino acid sequence that is specifically recognized as an acetylation substrate by a cognate acetyltransferase, and may for example, comprise an amino acid sequence comprising a Lys residue, wherein the amino acid sequence is specifically recognized by a histone acetyltransferase as an acetylatable peptide sequence, such the sequence Ile-Arg-Arg-Phe-Gln-Lys-Ser-Thr-Asp-Leu-Leu (SEQ. ID NO: 19). The linker may comprise a bromo-domain, wherein the bromo-domain peptide is linked to the fluorogen-activating peptide or the blocking peptide.

An embodiment of a biosensor may comprising a fluorogen-activating peptide comprising a variable domain of an antibody, and a blocking peptide comprising a variable domain of an antibody, wherein one of the fluorogen-activating peptide and the blocking peptide comprises a variable heavy chain domain of an antibody and the other peptide comprises a variable light chain domain of a different antibody, and wherein the blocking peptide is linked to the fluorogen-activating peptide through a peptide linker comprising an amino acid sequence that is specifically recognized as a cleavage substrate by a cognate protease, and wherein the blocking peptide associates with the fluorogen-activating peptide thereby blocking an active domain of the fluorogen-activating peptide when the linker is intact, and wherein the fluorogen-activating peptide and the blocking peptide disassociate when the linker is cleaved by a cognate protease, thereby allowing the fluorogen-activating peptide to interact with a cognate fluorogen and modulate a fluorescence signal.

Embodiments described herein include a composition comprising any of the biosensors described herein and a fluorogen. The fluorogen may be selected from the group consisting of thiazole orange, malachite green, dimethyl indole red, and derivatives thereof.

Embodiments described herein include a method for analyzing enzyme activity comprising contacting a medium comprising an analyte enzyme with the composition described herein, and detecting a fluorescence signal produced by an interaction between the fluorogen-activating peptide and the fluorogen.

Embodiments described herein include a method for analyzing enzyme activity comprising contacting a reaction medium comprising an analyte enzyme with a composition comprising a fluorogen and a biosensor that comprises a fluorogen-activating peptide and a blocking peptide linked to the fluorogen-activating peptide through a peptide linker, and detecting a fluorescence signal produced by an interaction between the fluorogen-activating peptide and the fluorogen. The peptide linker may comprise an amino acid sequence that is specifically recognized as a modification substrate by a cognate enzyme, wherein the blocking peptide associates with the fluorogen-activating peptide thereby blocking an active domain of the fluorogen-activating peptide when the peptide linker is unmodified, and wherein the fluorogen-activating peptide and the blocking peptide at least partially disassociate when the linker is modified by a cognate enzyme, thereby allowing the fluorogen-activating peptide to bind a cognate fluorogen and modulate a fluorescence signal.

The constructs and methods described herein may serve as a platform for the development and construction of numerous other specific biosensors not expressly disclosed herein. The constructs and methods described herein are extendable to other analytes and other fluorogen-activating peptides, blocking peptides, and peptide linkers. In this manner, numerous biosensors comprising various different fluorogen-activating peptides, blocking peptides and peptide linkers may be developed and constructed.

All patents, patent applications, publications, or other disclosure material mentioned herein, are hereby incorporated by reference in their entirety as if each individual reference was expressly incorporated by reference respectively. All references said to be incorporated by reference herein are incorporated herein only to the extent that the incorporated material does not conflict with existing definitions, statements, or other disclosure material set forth in this disclosure. As such, and to the extent necessary, the disclosure as set forth herein supersedes any conflicting material incorporated herein by reference. Any material, or portion thereof, that is said to be incorporated by reference herein, but which conflicts with existing definitions, statements, or other disclosure material set forth herein is only incorporated to the extent that no conflict arises between that incorporated material and the existing disclosure material. In case of conflict, the disclosure expressly set forth in the present application controls.

The present invention has been described with reference to various exemplary and illustrative embodiments. The embodiments described herein are understood as providing illustrative features of varying detail of various embodiments of the disclosed invention; and therefore, unless otherwise specified, the features, elements, components, constituents, ingredients, structures, modules, and/or aspects of the disclosed embodiments may be combined, separated, interchanged, and/or rearranged without departing from the scope of the disclosed invention. Accordingly, it will be recognized by persons having ordinary skill in the art that various substitutions, modifications or combinations of any of the exemplary embodiments may be made without departing from the scope of the invention. In addition, persons skilled in the art will recognize, or be able to ascertain using no more than routine experimentation, many equivalents to the various embodiments of the invention described herein upon review of this specification. Thus, the invention is not limited by the description of the various embodiments, but rather by the claims.

What is claimed is:

1. A biosensor comprising:

a fluorogen-activating peptide having an active domain; and a blocking peptide linked to the fluorogen-activating peptide and positioned to block the active domain of the fluorogen-activating peptide;

wherein the fluorogen-activating peptide comprises a variable heavy chain domain of an antibody and the blocking peptide comprises a variable light chain domain of a different antibody;

wherein the blocking peptide is linked to the fluorogen-activating peptide through a cleavable peptide linker comprising an amino acid sequence recognized by a protease enzyme, wherein the blocking peptide blocks the active domain of the fluorogen-activating peptide when the peptide linker is intact and wherein the fluorogen-activating peptide and the blocking peptide at least partially disassociate when the peptide linker is cleaved; and wherein the fluorogen-activating peptide that at least partially disassociates when the peptide linker is cleaved is able to bind to the cognate fluorogen thereby modulating a fluorescence signal of the cognate fluorogen, wherein:

the variable heavy chain domain comprises the amino acid sequence of SEQ ID NO: 33, and the variable light chain domain comprises the amino acid sequence of SEQ ID NO: 21; or the variable heavy chain domain comprises the amino acid sequence of SEQ ID NO: 23, and the variable light chain domain comprises the amino acid sequence of SEQ ID NO: 25.

2. The biosensor of claim 1, wherein the fluorogen-activating peptide specifically binds to the cognate fluorogen selected from the group consisting of thiazole orange, malachite green, dimethyl indole red, and derivatives thereof.

3. The biosensor of claim 1, wherein the peptide linker comprises an amino acid sequence that is recognized by a serine protease, a threonine protease, a cysteine protease, an aspartic acid protease, a matrix metalloproteinase, or a glutamic acid protease.

4. The biosensor of claim 1, wherein:

the peptide linker comprises Glu Asn Leu Tyr Phe Gln Gly (SEQ ID NO:7) and is recognized by TEV protease;

the peptide linker comprises Leu Glu Val Leu Phe Gln Gly Pro (SEQ ID NO:9) and is recognized by a HRV-3C protease;

the peptide linker comprises Tyr Val Ala Asp (SEQ ID NO:11) and is recognized by a caspase 1 protease;

the peptide linker comprises Asp Glu Val Asp (SEQ ID NO:13) and is recognized by a caspase 3 protease; or the peptide linker comprises Val Met Arg Leu Val Val (SEQ ID NO:15) and is recognized by MMP25 protease.

5. The biosensor of claim 1, wherein the variable heavy chain domain consists of the amino acid sequence of SEQ ID NO: 33, and the variable light chain domain consists of the amino acid sequence of SEQ ID NO: 21.

6. The biosensor of claim 1, wherein the variable heavy chain domain consists of the amino acid sequence of SEQ ID NO: 23, and the variable light chain domain consists of the amino acid sequence of SEQ ID NO: 25.

7. A composition comprising: a biosensor according to claim 1 and a fluorogen.

8. The composition of claim 7, wherein the fluorogen is selected from the group consisting of thiazole orange, malachite green, dimethyl indole red, and derivatives thereof.

9. A method for analyzing protease enzyme activity comprising:

contacting a medium comprising an analyte protease enzyme with the composition according to claim 7; and detecting a fluorescence signal produced by an interaction between the fluorogen activating peptide and the fluorogen.

10. The method of claim 9, wherein the fluorogen is selected from the group consisting of thiazole orange, malachite green, dimethyl indole red, and derivatives thereof.

* * * * *

SEQUENCE LISTING

```
<160> NUMBER OF SEQ ID NOS: 64

<210> SEQ ID NO 1
<211> LENGTH: 15
<212> TYPE: PRT
<213> ORGANISM: Artificial Sequence
<220> FEATURE:
<223> OTHER INFORMATION: PNNL yeast scFv library linker sequence

<400> SEQUENCE: 1

Gly Gly Gly Gly Ser Gly Gly Gly Gly Ser Gly Gly Gly Gly Ser
1               5                   10                  15

<210> SEQ ID NO 2
<211> LENGTH: 45
<212> TYPE: DNA
<213> ORGANISM: Artificial Sequence
<220> FEATURE:
<223> OTHER INFORMATION: Linker DNA Sequence

<400> SEQUENCE: 2
ggtggcggtg gcagcggcgg tggtggttcc ggaggcggcg gttct              45

<210> SEQ ID NO 3
<211> LENGTH: 5
<212> TYPE: PRT
<213> ORGANISM: Artificial Sequence
<220> FEATURE:
<223> OTHER INFORMATION: Furin Short Recognition Sequence

<400> SEQUENCE: 3

Arg Lys Lys Arg Ser
1               5

<210> SEQ ID NO 4
<211> LENGTH: 15
<212> TYPE: DNA
<213> ORGANISM: Artificial Sequence
<220> FEATURE:
<223> OTHER INFORMATION: Furin Short Recognition Sequence DNA

<400> SEQUENCE: 4
agaaagaaga gatct                                              15

<210> SEQ ID NO 5
```

```
<211> LENGTH: 10
<212> TYPE: PRT
<213> ORGANISM: Artificial Sequence
<220> FEATURE:
<223> OTHER INFORMATION: Furin Long Recognition Sequence

<400> SEQUENCE: 5

Asn Ser Arg Lys Lys Arg Ser Thr Ser Ala
1               5                   10

<210> SEQ ID NO 6
<211> LENGTH: 30
<212> TYPE: DNA
<213> ORGANISM: Artificial Sequence
<220> FEATURE:
<223> OTHER INFORMATION: Furin Long Recognition Sequence DNA

<400> SEQUENCE: 6
aactcgagaa agaagagatc tacctccgct                                      30

<210> SEQ ID NO 7
<211> LENGTH: 7
<212> TYPE: PRT
<213> ORGANISM: Artificial Sequence
<220> FEATURE:
<223> OTHER INFORMATION: TEV Protease Recognition Sequence

<400> SEQUENCE: 7

Glu Asn Leu Tyr Phe Gln Gly
1               5

<210> SEQ ID NO 8
<211> LENGTH: 21
<212> TYPE: DNA
<213> ORGANISM: Artificial Sequence
<220> FEATURE:
<223> OTHER INFORMATION: TEV Protease Recognition Sequence DNA

<400> SEQUENCE: 8
gaaaacctat acttccaagg t                                               21

<210> SEQ ID NO 9
<211> LENGTH: 8
<212> TYPE: PRT
<213> ORGANISM: Artificial Sequence
<220> FEATURE:
<223> OTHER INFORMATION: HRV-3C Protease Recognition Sequence

<400> SEQUENCE: 9

Leu Glu Val Leu Phe Gln Gly Pro
1               5

<210> SEQ ID NO 10
<211> LENGTH: 24
<212> TYPE: DNA
<213> ORGANISM: Artificial Sequence
<220> FEATURE:
<223> OTHER INFORMATION: HRV-3C Protease Recognition Sequence DNA

<400> SEQUENCE: 10
ttggaagttt tgttccaagg tcca                                            24

<210> SEQ ID NO 11
<211> LENGTH: 4
<212> TYPE: PRT
<213> ORGANISM: Artificial Sequence
<220> FEATURE:
```

<223> OTHER INFORMATION: Caspase 1 Protease Recognition Sequence

<400> SEQUENCE: 11

Tyr Val Ala Asp
1

<210> SEQ ID NO 12
<211> LENGTH: 12
<212> TYPE: DNA
<213> ORGANISM: Artificial Sequence
<220> FEATURE:
<223> OTHER INFORMATION: Caspase 1 Protease Recognition Sequence DNA

<400> SEQUENCE: 12
tacgttgctg ac                                                              12

<210> SEQ ID NO 13
<211> LENGTH: 4
<212> TYPE: PRT
<213> ORGANISM: Artificial Sequence
<220> FEATURE:
<223> OTHER INFORMATION: Caspase 3 Protease Recognition Sequence

<400> SEQUENCE: 13

Asp Glu Val Asp
1

<210> SEQ ID NO 14
<211> LENGTH: 12
<212> TYPE: DNA
<213> ORGANISM: Artificial Sequence
<220> FEATURE:
<223> OTHER INFORMATION: Caspase 3 Protease Recognition Sequence DNA

<400> SEQUENCE: 14
gacgaagttg ac                                                              12

<210> SEQ ID NO 15
<211> LENGTH: 6
<212> TYPE: PRT
<213> ORGANISM: Artificial Sequence
<220> FEATURE:
<223> OTHER INFORMATION: MMP25 Recognition Sequence

<400> SEQUENCE: 15

Val Met Arg Leu Val Val
1               5

<210> SEQ ID NO 16
<211> LENGTH: 18
<212> TYPE: DNA
<213> ORGANISM: Artificial Sequence
<220> FEATURE:
<223> OTHER INFORMATION: MMP25 Recognition Sequence DNA

<400> SEQUENCE: 16
gtcatgagat tggtcgtc                                                        18

<210> SEQ ID NO 17
<211> LENGTH: 9
<212> TYPE: PRT
<213> ORGANISM: Artificial Sequence
<220> FEATURE:
<223> OTHER INFORMATION: PKA Kemptide Recognition Sequence

<400> SEQUENCE: 17

-continued

```
Leu Leu Arg Arg Ala Ser Leu Gly Pro
1               5
```

<210> SEQ ID NO 18
<211> LENGTH: 27
<212> TYPE: DNA
<213> ORGANISM: Artificial Sequence
<220> FEATURE:
<223> OTHER INFORMATION: PKA Kemptide DNA

<400> SEQUENCE: 18

```
ttgttgagaa gagctagttt gggtcca                                       27
```

<210> SEQ ID NO 19
<211> LENGTH: 11
<212> TYPE: PRT
<213> ORGANISM: Artificial Sequence
<220> FEATURE:
<223> OTHER INFORMATION: H3-K56 histone acetyltransferase recognition
      sequence

<400> SEQUENCE: 19

```
Ile Arg Arg Phe Gln Lys Ser Thr Asp Leu Leu
1               5                   10
```

<210> SEQ ID NO 20
<211> LENGTH: 33
<212> TYPE: DNA
<213> ORGANISM: Artificial Sequence
<220> FEATURE:
<223> OTHER INFORMATION: H3-K56 HAT Recognition Sequence DNA

<400> SEQUENCE: 20

```
atcagaaagat tccaaaagtc caccgacttg ttg                               33
```

<210> SEQ ID NO 21
<211> LENGTH: 252
<212> TYPE: PRT
<213> ORGANISM: Artificial Sequence
<220> FEATURE:
<223> OTHER INFORMATION: scFv sequence

<400> SEQUENCE: 21

```
Gln Val Gln Leu Val Glu Ser Glu Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Leu Leu Asp Thr Thr Met Val Thr Gly Tyr Tyr Phe Asp Tyr Trp
            100                 105                 110

Gly Gln Gly Thr Leu Val Thr Val Ser Ser Gly Ile Leu Gly Ser Gly
        115                 120                 125

Gly Gly Gly Ser Gly Gly Gly Gly Ser Gly Gly Gly Ser Asn Phe
    130                 135                 140

Met Leu Thr Gln Pro Pro Ser Ala Ser Gly Thr Pro Gly Gln Ser Val
```

```
                145                 150                 155                 160
Thr Ile Ser Cys Ser Gly Ser Gly Ser Asn Ile Gly Asn Asn Lys Val
                    165                 170                 175

Asn Trp Tyr Gln Gln Leu Pro Gly Thr Ala Pro Lys Leu Leu Ile Tyr
                    180                 185                 190

Ser Asn Asn Gln Arg Pro Ser Gly Val Pro Asp Arg Phe Ser Gly Ser
                    195                 200                 205

Lys Ser Gly Thr Ser Ala Ser Leu Ala Ile Ser Gly Leu Gln Ser Glu
                    210                 215                 220

Asp Glu Ala Asp Tyr Tyr Cys Ala Ala Trp Asp Asp Ser Leu Asn Gly
225                 230                 235                 240

Tyr Val Phe Gly Thr Gly Thr Lys Leu Thr Val Leu
                    245                 250
```

<210> SEQ ID NO 22
<211> LENGTH: 1221
<212> TYPE: DNA
<213> ORGANISM: Artificial Sequence
<220> FEATURE:
<223> OTHER INFORMATION: scFv sequence

<400> SEQUENCE: 22

```
catttttcaat taagatgcag ttacttcgct gttttttcaat attttctgtt attgcttcag     60
ttttagcaca ggaactgaca actatatgcg agcaaatccc ctcaccaact ttagaatcga    120
cgccgtactc tttgtcaacg actactattt tggccaacgg gaaggcaatg caaggagttt    180
ttgaatatta caaatcagta acgtttgtca gtaattgcgg ttctcacccc tcaacaacta    240
gcaaaggcag ccccataaac acacagtatg ttttttaagga caatagctcg acgattgaag    300
gtagatacccc atacgacgtt ccagactacg ctctgcaggc tagtggtggt ggtggttctg    360
gtggtggtgg ttctggtggt ggtggttctg ctagccaggt gcagctggtg aatctgagg    420
ctgaggtgaa gaagcctggg tcctcggtga aggtctcctg caaggcttct ggaggcacct    480
tcagcagcta tgctatcagc tgggtgcgac aggcccctgg acaagggctt gagtggatgg    540
gagggatcat ccctatcttt ggtacagcaa actacgcaca gaagttccag gcagagtca    600
cgattaccgc ggacgaatcc acgagcacag cctacatgga gctgagcagc ctgagatctg    660
aggacacggc cgtgtattac tgtgtcttgt tggatacaac tatggttacg gatactact    720
ttgactactg gggccaggga accctggtca ccgtctcctc aggaattcta ggatccggtg    780
gcggtggcag cggcggtggt ggttccggag gcggcggttc taattttatg ctgactcagc    840
cccctcagc gtctgggacc cccgggcaga gcgtcaccat ctcttgttct ggaagcggct    900
cgaacatcgg aaacaataaa gtaaactggt accagcagct cccaggaacg gcccccaaac    960
tcctcatcta tagtaataat cagcggccct cagggtgtccc tgaccgattc tctggctcca   1020
agtctggcac ctcagcctcc ctggccatca gtgggctcca gtctgaggat gaggctgatt   1080
attactgtgc agcatgggat gacagcctga atggttatgt cttcggaact gggaccaagc   1140
tcaccgtcct atccggaatt ctagaacaaa agcttatttc tgaagaagac ttgtaatagc   1200
tcggcggccg catcgagatc t                                              1221
```

<210> SEQ ID NO 23
<211> LENGTH: 264
<212> TYPE: PRT
<213> ORGANISM: Artificial Sequence
<220> FEATURE:
<223> OTHER INFORMATION: scFv sequence

<400> SEQUENCE: 23

Gln Val Gln Leu Val Glu Ser Glu Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Arg Ile Asp Gly Asp Gly Ser Ser Thr Asn Tyr Ala Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ala Glu Asp Thr Ala Val Tyr Tyr Cys
                85                  90                  95

Thr Arg Ala Arg Tyr Phe Gly Ser Val Ser Pro Tyr Gly Met Asp Val
            100                 105                 110

Trp Gly Gln Gly Thr Thr Val Thr Val Ser Ser Gly Ile Leu Gly Ser
        115                 120                 125

Gly Gly Gly Gly Ser Gly Gly Gly Ser Gly Gly Gly Gly Ser Asp
    130                 135                 140

Ile Arg Val Thr Gln Ser Pro Ser Ser Val Ser Ala Ser Val Gly Asp
145                 150                 155                 160

Arg Val Thr Ile Ser Cys Arg Ala Ser Gln Gly Ile Ala Thr Trp Leu
                165                 170                 175

Gly Trp Tyr Gln Gln Lys Pro Gly Lys Pro Pro Gln Leu Leu Ile Tyr
            180                 185                 190

Ser Ala Ser Thr Leu Gln Thr Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Val Ala Thr Tyr Tyr Cys Gln Glu Gly Ser Thr Phe Pro Leu Thr
225                 230                 235                 240

Phe Gly Gly Gly Thr Lys Val Asp Ile Lys Ser Gly Ile Leu Glu Gln
                245                 250                 255

Lys Leu Ile Ser Glu Glu Asp Leu
            260

<210> SEQ ID NO 24
<211> LENGTH: 881
<212> TYPE: DNA
<213> ORGANISM: Artificial Sequence
<220> FEATURE:
<223> OTHER INFORMATION: scFv sequence

<400> SEQUENCE: 24
ctctgcaggc tagtggtggt ggtggttctg gtggtggtgg ttctgctagc caggtgcagc    60
tggtggagtc tgagggaggc ttggtacagc ctggagggtc cctgagactc tcctgtgcag   120
cctctggatt caccttcagt agttatgaaa tgaactgggt ccgccaggct ccaggtaagg   180
ggctggagtg gtctcacgt attgatggtg atgggagcag cacaaactac gcggactccg   240
tgaagggccg attcaccatc tccagagaca acgccaagag cacgctgtat ctgcaaatga   300
atagtctgag agccgaggac acggctgtgt attactgtac aagggccaga tactttggtt   360
cggtgagccc ctacggtatg gacgtctggg gccaagggac cacggtcacc gtctcctcag   420
gaattctagg atccggtggc ggtggcagcg gcggtggtgg ttccggaggc ggcggttctg   480

```
acatccgggt gacccagtct ccttcttccg tgtctgcatc tgtgggtgac agagtcacca    540
tcagttgtcg ggcgagtcag gggattgcca cctggttagg ctggtatcag cagaagccag    600
ggaaaccccc tcagctcctt atctattctg catccacttt gcaaactggg gtcccatcaa    660
ggttcagcgg cagtggatct gggacagatt tcactcttac catcagcagc ctgcagccgg    720
aggatgttgc aacttactat tgtcaagagg gtagcacttt ccctctcact ttcggcggag    780
ggaccaaagt ggatatcaaa tccggaattc tagaacaaaa gcttatttct gaagaagact    840
tgtaatagct cggcggccgc atcgagatct gataacaaca g    881
```

<210> SEQ ID NO 25
<211> LENGTH: 268
<212> TYPE: PRT
<213> ORGANISM: Artificial Sequence
<220> FEATURE:
<223> OTHER INFORMATION: scFv sequence
<400> SEQUENCE: 25

```
Gln Val Gln Leu Gln Gln Trp Asp Ala Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Pro Gly Arg Thr Tyr Tyr Arg Ser Lys Trp Gln Asn Asn Tyr Ala
    50                  55                  60

Leu Ser Val Gln Gly Arg Ile Thr Ile Asn Pro Asp Thr Ser Asn Asn
65                  70                  75                  80

Gln Phe Ser Leu Gln Leu Asp Ser Met Thr Pro Glu Asp Thr Gly Val
                85                  90                  95

Tyr Tyr Cys Thr Arg Gly Gly Gly Ser Leu Asp Tyr Trp Gly Gln Gly
            100                 105                 110

Thr Leu Val Thr Val Ser Ser Gly Ser Ala Ser Ala Pro Thr Gly Ile
        115                 120                 125

Leu Gly Ser Gly Gly Gly Gly Ser Gly Gly Gly Ser Gly Gly Gly
    130                 135                 140

Gly Ser Ser Tyr Glu Leu Thr Gln Pro Pro Ser Val Ser Val Ser Pro
145                 150                 155                 160

Gly Gln Thr Ala Thr Ile Thr Cys Ser Gly Asp Glu Met Gly Asp Lys
                165                 170                 175

Tyr Ala Tyr Trp Tyr Gln Gln Lys Pro Gly Gln Ala Pro Val Leu Val
            180                 185                 190

Ile Tyr Lys Asp Ser Glu Arg Pro Ser Gly Ile Pro Glu Arg Phe Ser
        195                 200                 205

Gly Ser Ser Ser Gly Thr Thr Val Thr Leu Thr Ile Ser Gly Val Gln
    210                 215                 220

Ala Glu Asp Glu Ala Asp Tyr Tyr Cys Gln Ser Ala Asp Ser Ser Gly
225                 230                 235                 240

Thr Ser Val Val Phe Gly Gly Gly Thr Lys Val Thr Val Leu Ser Gly
                245                 250                 255

Ile Leu Glu Gln Lys Leu Ile Ser Glu Glu Asp Leu
            260                 265
```

<210> SEQ ID NO 26
<211> LENGTH: 908

```
<212> TYPE: DNA
<213> ORGANISM: Artificial Sequence
<220> FEATURE:
<223> OTHER INFORMATION: scFv sequence

<400> SEQUENCE: 26
ctctgcaggc tagtggtggt ggtggttctg gtggtggtgg ttctggtggt ggtggttctg      60
ctagccaggt gcagctacag cagtgggacg caggactggt gaagccctcg cagaccctct     120
cactcacctg tgccatctcc ggggacagtg tctctagcaa cagtgctgct tggaactgga     180
tcaggcagtc cccatcgaga ggtcttgagt ggccgggaag acatactac aggtccaagt      240 ggcaaaacaa ttatgcactc tctgtgcaag gtcgaataac catcaaccca gacacatcca     300
acaaccaatt ctccctgcag ctggactcta tgactcccga ggacacgggt gtatattact     360
gtacaagggg cggcgggtcc ttagactact ggggccaggg aaccctggtc accgtctcct     420
cagggagtgc atccgcccca accggaattc taggatccgg tggcggtggc agcggcggtg     480
gtggttccgg aggcggcggt tcttcctatg agctgacaca gccaccctca gtgtccgtgt     540
ccccaggaca gacagccacc atcacctgct ctggagatga atgggggat aaatatgctt      600 attggtacca gcagaagcca ggccaggccc ctgtgctggt gatatataaa gacagtgaga     660
ggccctcagg gatccctgag cgattctctg gctccagctc agggacaaca gtcaccttga     720
ccatcagtgg agtccaggca gaagacgagg ctgactatta ctgtcaatca gcagacagca     780
gtggtacttc tgtggtattc ggcggaggga ccaaggtcac cgtcctatcc ggaattctag     840
aacaaaagct tatttctgaa gaagacttgt aatagctcgg cggccgcatc gagatctgat     900
aacaacag                                                            908

<210> SEQ ID NO 27
<211> LENGTH: 279
<212> TYPE: PRT
<213> ORGANISM: Artificial Sequence
<220> FEATURE:
<223> OTHER INFORMATION: scFv sequence

<400> SEQUENCE: 27

Gln Val Gln Leu Gln Gln Ser Gly Pro Gly Arg Val Lys Pro Ser Gln
1               5                   10                  15

Thr Leu Ser Leu Thr Cys Asp Ile Ser Gly Asp Ser Val Ser Ser Asn
                20                  25                  30

Ser Val Ala Trp Asn Trp Ile Arg Gln Ser Pro Ser Arg Gly Leu Glu
            35                  40                  45

Trp Leu Gly Arg Thr Tyr Tyr Arg Ser Lys Trp Ile Asn Glu Tyr Gly
        50                  55                  60

Pro Phe Val Arg Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Thr Met Ala Asn Ser Gly Tyr Asp Arg Ser Ser Gly
            100                 105                 110

His Asn Tyr Gly Met Asp Val Trp Gly Gln Gly Thr Thr Val Thr Val
        115                 120                 125

Ser Ser Gly Ser Ala Ser Ala Pro Thr Gly Ile Leu Gly Ser Gly Gly
    130                 135                 140

Gly Gly Ser Gly Gly Gly Gly Ser Gly Gly Gly Gly Ser Ser Tyr Glu
145                 150                 155                 160
```

```
Leu Thr Gln Pro Pro Ser Val Ser Val Ser Pro Gly Gln Thr Ala Arg
                165                 170                 175

Ile Thr Cys Ser Gly Asp Ala Leu Pro Lys Gln Tyr Thr Tyr Trp Tyr
        180                 185                 190

Gln Gln Lys Ala Gly Gln Ala Pro Val Leu Val Ile Tyr Lys Asp Thr
    195                 200                 205

Glu Arg Pro Ser Gly Ile Pro Glu Arg Phe Ser Gly Thr Ser Ser Gly
210                 215                 220

Thr Thr Val Thr Leu Thr Ile Ser Gly Val Gln Ala Glu Asp Glu Ala
225                 230                 235                 240

Asp Tyr Tyr Cys Gln Ser Ala Asp Ser Ser Gly Ser Tyr Val Phe Phe
                245                 250                 255

Gly Gly Gly Thr Lys Val Thr Val Leu Ser Gly Ile Leu Glu Gln Lys
                260                 265                 270

Leu Ile Ser Glu Glu Asp Leu
            275
```

```
<210> SEQ ID NO 28
<211> LENGTH: 935
<212> TYPE: DNA
<213> ORGANISM: Artificial Sequence
<220> FEATURE:
<223> OTHER INFORMATION: scFv sequence

<400> SEQUENCE: 28
cgctctgcag gctagtggtg gtggtggttc tggtggtggt ggttctggtg gtggtggttc    60
tgctagccag gtacagctgc agcagtcagg tccaggacgg gtgaagccct cgcagaccct   120
ctcactcacc tgtgacatct ccggggacag tgtctctagc aacagtgttg cttggaactg   180
gatcaggcag tccccatcga gaggccttga gtggctggga aggacatact acaggtccaa   240
gtggattaat gaatatggac catttgtaag aagtcgaata accatcaacc cagacacatc   300
caagaatcag ttctccctgc agttgaactc tgtgactccc gaggacacgg ctgtctatta   360
ctgtgcaaca atggcgaata gtggctacga tcggtcctct ggtcacaact acggaatgga   420
cgtctggggc caagggacca cggtcaccgt ctcctcaggg agtgcatccg ccccaaccgg   480
aattctagga tccggtggcg gtggcagcgg cggtggtggt tccggaggcg gcggttcttc   540
ctatgagttg actcagccac cctcggtgtc agtgtcccca ggacagacgg ccaggatcac   600
ctgctctgga gatgcattgc caaagcaata tacttattgg taccagcaga aggcaggcca   660
ggcccctgtc ttggtgatat ataaagacac tgagaggccc tcaggatccc tgagcgatt    720
ctctggtacc agttcaggga acacagtcac attgaccatc agtggagtcc aggcagaaga   780
cgaggctgac tattactgtc aatcagcaga cagcagtggt tcctatgttt tcttcggcgg   840
agggaccaag gtgaccgtcc tatccggaat tctagaacaa aagcttattt ctgaagaaga   900
cttgtaatag ctcggcggcc gcatcgagat ctgat                              935
```

```
<210> SEQ ID NO 29
<211> LENGTH: 123
<212> TYPE: PRT
<213> ORGANISM: Artificial Sequence
<220> FEATURE:
<223> OTHER INFORMATION: scFv sequence

<400> SEQUENCE: 29

Gln Ala Val Val Thr Gln Glu Pro Ser Val Thr Val Ser Pro Gly Gly
1               5                   10                  15
```

Thr Val Ile Leu Thr Cys Gly Ser Ser Thr Gly Ala Val Thr Ser Gly
            20                  25                  30

His Tyr Ala Asn Trp Phe Gln Gln Lys Pro Gly Gln Ala Pro Arg Ala
            35                  40                  45

Leu Ile Phe Glu Thr Asp Lys Lys Tyr Ser Trp Thr Pro Gly Arg Phe
        50                  55                  60

Ser Gly Ser Leu Leu Gly Ala Lys Ala Ala Leu Thr Ile Ser Asp Ala
65                  70                  75                  80

Gln Pro Glu Asp Glu Ala Glu Tyr Tyr Cys Leu Leu Ser Asp Val Asp
                85                  90                  95

Gly Tyr Leu Phe Gly Gly Gly Thr Gln Leu Thr Val Leu Ser Gly Ile
            100                 105                 110

Leu Glu Gln Lys Leu Ile Ser Glu Glu Asp Leu
        115                 120

<210> SEQ ID NO 30
<211> LENGTH: 651
<212> TYPE: DNA
<213> ORGANISM: Artificial Sequence
<220> FEATURE:
<223> OTHER INFORMATION: scFv sequence

<400> SEQUENCE: 30
ggctagtggt ggtggtggtt ctggtggtgg tggttctgct agcactggca gctttgactc      60
ctggggccag ggaaccctgg tcaccgtctc ctcaggaatt ctaggatccg gtggcggtgg     120
cagcggcggt ggtggttccg gaggcggcgg ttctcaggct gtggtgactc aggagccgtc     180
agtgactgtg tccccaggag ggacagtcat tctcacttgt ggctccagca ctggagctgt     240
caccagtggt cattatgcca actggttcca gcagaagcct ggccaagccc ccagggcact     300
tatatttgaa accgacaaga atattcctg acccctggc cgattctcag gctccctcct       360
tggggccaag gctgccctga ccatctcgga tgcgcagcct gaagatgagg ctgagtatta     420
ctgtttgctc tccgacgttg acggttatct gttcggagga ggcacccagc tgaccgtcct     480
ctccggaatt ctagaacaaa agcttatttc tgaagaagac ttgtaatagc tcggcggccg     540
catcgagatc tgataacaac agtgtagatg taacaaaatc gactttgttc ccactgtact     600
tttagctcgt acaaaataca atatactttt catttctccg taaacaacat g              651

<210> SEQ ID NO 31
<211> LENGTH: 124
<212> TYPE: PRT
<213> ORGANISM: Artificial Sequence
<220> FEATURE:
<223> OTHER INFORMATION: scFv sequence

<400> SEQUENCE: 31

Gln Val Gln Leu Gln Gln Ser Gly Pro Gly Leu Val Arg Pro Ser Gln
1               5                   10                  15

Thr Leu Ser Leu Thr Cys Ala Ile Ser Gly Asp Ser Val Pro Lys Asn
            20                  25                  30

Gly Ala Ser Trp Asn Trp Ile Arg Leu Ser Pro Ser Arg Gly Leu Glu
        35                  40                  45

Trp Leu Gly Arg Thr His Tyr Ser Ser Arg Trp Tyr His Asp Tyr Ala
    50                  55                  60

Phe Phe Val Lys Ser Arg Ile Thr Ile Asn Val Asp Thr Ser Glu Thr
65                  70                  75                  80

Gln Val Ser Leu Gln Leu Asp Ser Val Thr Pro Asp Asp Thr Gly Val

```
                    85                  90                  95
Tyr Tyr Cys Ala Arg Glu Ser Gln Arg Arg Gly Trp Phe Asp Leu Trp
            100                 105                 110

Gly Gln Gly Thr Leu Val Thr Val Ser Gln Glu Phe
        115                 120
```

<210> SEQ ID NO 32
<211> LENGTH: 853
<212> TYPE: DNA
<213> ORGANISM: Artificial Sequence
<220> FEATURE:
<223> OTHER INFORMATION: scFv sequence

<400> SEQUENCE: 32

```
ggtggtggtg ttctggtgg tggtggttct gctagccagg tacagctgca gcagtcaggt      60
ccaggactgg tgaggccctc gcagaccctc tcactcacct gtgccatctc cggggacagt    120
gtccctaaga cgtgcatc ttggaactgg atcaggctgt caccatcgcg aggccttgag      180
tggctgggaa ggactcacta cagttccagg tggtatcatg attatgcatt ctttgtgaag    240
agtcgaataa ccatcaacgt agatacatc gagacccaag tcagtctgca gctggactct     300
gtgactcccg acgacgggg tgtttattac tgtgcaagag aatctcaacg taggggatgg    360
ttcgacctct ggggccaggg aaccctggtc accgtctccc aggaattcta ggatccggtg    420
gcggtggcag cggcggtggt ggttccggag cggcggttc taattttatg ctgactcagc    480
cccactctgt gtcggagtct ccggggagga cggttacctt ctcctgcacc cgcagcagtg    540
gcggcattgc cagcaactat gtgcagtggt accaacagcg cccgggcagt accccccacca   600
ctgtgatcta tgggatagc caaagaccct ctggagtccc tgatcggttc tctggctcca   660
tcgacagctc ctccaattct gcctccctca ccatctcagg gctgaaggct gaggacgagg    720
ctgactacta ctgtcagtcc tctgatggta gctcttgggt gttcggcgga ggcacccagc    780
tgaccgtcct ctccggaatt ctagaacaaa agcttatttc tgaagaagac ttgtaatagc    840
tcggcggcgg cat                                                       853
```

<210> SEQ ID NO 33
<211> LENGTH: 154
<212> TYPE: PRT
<213> ORGANISM: Artificial Sequence
<220> FEATURE:
<223> OTHER INFORMATION: scFv sequence

<400> SEQUENCE: 33

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Ser
            20                  25                  30

His Tyr Tyr Trp Gly Trp Ile Arg Gln Pro Pro Gly Lys Gly Pro Glu
        35                  40                  45

Trp Ile Gly Ser Met Tyr Tyr Ser Gly Arg Thr Tyr Tyr Asn Pro Ala
    50                  55                  60

Leu Lys Ser Arg Val Thr Ile Ser Pro Asp Lys Ser Lys Asn Gln Phe
65                  70                  75                  80

Phe Leu Lys Leu Thr Ser Val Thr Ala Ala Asp Thr Ala Val Tyr Tyr
                85                  90                  95

Cys Ala Arg Glu Gly Pro Thr His Tyr Tyr Asp Asn Ser Gly Pro Ile
            100                 105                 110
```

```
Pro Ser Asp Glu Tyr Phe Gln His Trp Gly Gln Gly Thr Leu Val Thr
        115                 120                 125

Val Ser Ser Gly Ile Leu Gly Ser Gly Gly Gly Ser Gly Gly Gly
    130                 135                 140

Gly Ser Gly Gly Gly Gly Leu Gln Glu Phe
145                 150
```

<210> SEQ ID NO 34
<211> LENGTH: 781
<212> TYPE: DNA
<213> ORGANISM: Artificial Sequence
<220> FEATURE:
<223> OTHER INFORMATION: scFv sequence

<400> SEQUENCE: 34

```
actagcaaag gcagccccat aaacacacag tatgttttta aggacaatag ctcgacgatt      60
gaaggtagat acccatacga cgttccagac tacgctctgc aggctagtgg tggtggtggt     120
tctggtggtg gtggttctgg tggtggtggt tctgctagcc aggtgcagct gcaggagtcg     180
ggcccaggac tggtgaagcc ttcggagacc ctgtccctca cctgcactgt ctctggtgcc     240
tccatcagca gtagtcatta ctactggggc tggatccgcc agcccccagg aaggggcct     300
gagtggattg ggagtatgta ttatagtggg agaacgtact acaacccggc cctcaagagt     360
cgagtcacca tatcaccaga caagtcgaag aaccagttct tcttgaagtt gacctctgta     420
accgccgcgg acacggccgt gtattactgt gcgagggagg gacccacaca ttactatgat     480
aatagtggtc caatacctct ggatgagtat ttccagcact ggggccaggg taccctggtc     540
actgtctcct caggaattct aggatccggt ggcggtggca gcggcggtgg tggttccgga     600
ggcggcgggc tgcaggaatt ctagaacaaa agcttatttc tgaagaagac ttgtaatagc     660
tcggcggccg catcgagatc tgataacaac agtgtagatg taacaaaatc gactttgttc     720
ccactgtact tttagctcgt acaaaataca atatactttt catttctccg taaacaacat     780
g                                                                     781
```

<210> SEQ ID NO 35
<211> LENGTH: 252
<212> TYPE: PRT
<213> ORGANISM: Artificial Sequence
<220> FEATURE:
<223> OTHER INFORMATION: scFv sequence

<400> SEQUENCE: 35

```
Gln Val Gln Leu Val Glu Ser Glu Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Thr Ile Pro Ile Phe Gly Thr Ala Asp Tyr Ala Gln Glu Phe
    50                  55                  60

Gln Gly Arg Val Thr Ile Thr Thr Asp Glu Ser Thr Ser Thr Ala Tyr
65                  70                  75                  80

Met Glu Leu Ser Gly Leu Arg Ser Glu Asp Thr Ala Val Tyr Tyr Cys
                85                  90                  95

Val Leu Leu Gly Thr Thr Met Val Thr Gly His Tyr Phe Asp Tyr Trp
            100                 105                 110

Gly Gln Gly Thr Leu Val Thr Val Ser Ser Gly Ile Leu Gly Ser Gly
```

```
                115                 120                 125
Gly Gly Gly Ser Gly Gly Gly Ser Gly Gly Gly Ser Asn Phe
            130                 135                 140

Met Leu Thr Gln Pro Pro Ser Ala Ser Gly Thr Pro Gly Gln Ser Val
145                 150                 155                 160

Thr Ile Ser Cys Ser Gly Ser Gly Ser Asn Ile Gly Asn Asn Lys Val
                165                 170                 175

Asn Trp Tyr Gln Gln Leu Pro Gly Thr Ala Pro Lys Leu Leu Ile Tyr
            180                 185                 190

Ser Asn Asn Gln Arg Pro Ser Gly Val Pro Asp Arg Phe Ser Gly Ser
        195                 200                 205

Lys Ser Gly Thr Ser Ala Ser Leu Ala Ile Ser Gly Leu Gln Ser Glu
    210                 215                 220

Asp Glu Ala Asp Tyr Tyr Cys Ala Ala Trp Asp Asp Gly Leu Ser Gly
225                 230                 235                 240

Tyr Val Phe Gly Thr Gly Thr Lys Leu Thr Val Leu
                245                 250
```

<210> SEQ ID NO 36
<211> LENGTH: 845
<212> TYPE: DNA
<213> ORGANISM: Artificial Sequence
<220> FEATURE:
<223> OTHER INFORMATION: scFv sequence

<400> SEQUENCE: 36

```
ggttctggtg gtggtggttc tgctagccag gtgcagctgg tggaatctga ggctgaggtg      60
aagaagcctg gtcctcggt gaaggtctcc tgcaaggcct ctggaggcac cttcagcagc     120
tatgctatca gctgggtgcg gcaggcccct ggacaagggc ttgagtggat gggagggacc     180
atccctatct ttggtacagc agactacgca caggagttcc agggcagagt cacgattacc     240
acggacgaat ccacgagcac agcctacatg gagctgagcg gcctgagatc tgaggacacg     300
gccgtgtatt actgtgtttt gttgggtaca actatggtta cgggacacta ctttgactac     360
tggggccagg gaaccctggt caccgtctcc tcaggaattc taggatccgg tggcggtggc     420
agcggcggtg gtggttccgg aggcggcggt tctaatttta tgctgactca gccccccctca     480
gcgtctggga ccccggggca gagcgtcacc atctcttgtt ctggaagcgg ctcgaacatc     540
ggaaacaata agtaaactg gtaccagcag ctcccaggaa cggcccccaa actcctcatc     600
tatagtaata atcagcggcc ctcaggggtc cctgaccgat tctctggctc caagtctggc     660
acctcagcct ccctggccat cagtgggctc cagtctgagg atgaggctga ttattactgt     720
gcagcatggg atgacggtct gagtggttat gtcttcggaa ctgggaccaa gcttaccgtc     780
ctgtccggat ccgaacaaaa gcttatttct gaagaggact tgtaatagct cggcggccgc     840
atcga                                                                 845
```

<210> SEQ ID NO 37
<211> LENGTH: 252
<212> TYPE: PRT
<213> ORGANISM: Artificial Sequence
<220> FEATURE:
<223> OTHER INFORMATION: scFv sequence

<400> SEQUENCE: 37

```
Gln Val Gln Leu Val Glu Ser Glu Ala Glu Val Lys Lys Pro Gly Ser
1               5                   10                  15
```

| | | | | | | | | | | | | |
|---|---|---|---|---|---|---|---|---|---|---|---|---|
|Ser|Val|Lys|Val|Ser|Cys|Lys|Ala|Ser|Gly|Gly|Thr|Phe Ser Ser Tyr|
| | |20| | | |25| | | |30| | |

Ala Ile Ser Trp Val Arg Gln Ala Pro Gly Gln Gly Leu Glu Trp Met
     35                 40                 45

Gly Gly Thr Ile Pro Ile Phe Gly Thr Ala Asn Tyr Ala Gln Lys Phe
 50                   55                60

Gln Gly Arg Val Thr Ile Thr Ala Asp Glu Ser Thr Ser Thr Ala Tyr
65                 70                75              80

Met Glu Leu Ser Ser Leu Arg Ser Glu Asp Thr Ala Val Tyr Tyr Cys
          85                90              95

Val Leu Leu Gly Thr Thr Met Val Thr Gly Tyr Tyr Phe Asp Tyr Trp
     100                105             110

Gly Gln Gly Thr Leu Val Thr Val Ser Ser Gly Ile Leu Gly Ser Gly
     115                120             125

Gly Gly Gly Ser Gly Gly Gly Ser Gly Gly Gly Ser Asn Phe
 130                 135               140

Thr Leu Thr Gln Pro Pro Ser Ala Ser Gly Thr Pro Gly Gln Ser Val
145                150               155             160

Thr Ile Ser Cys Ser Gly Ser Ser Asn Ile Gly Asn Asn Lys Val
          165              170              175

Asn Trp Tyr Gln Gln Leu Pro Gly Thr Ala Pro Lys Leu Leu Ile Tyr
          180              185              190

Ser Asn Asn Gln Arg Pro Ser Gly Val Pro Asp Arg Phe Ser Gly Ser
     195                200             205

Lys Ser Gly Thr Ser Ala Ser Leu Ala Ile Ser Gly Leu Gln Ser Glu
210                215               220

Asp Glu Ala Asp Tyr Tyr Cys Ala Ala Trp Asp Asp Ser Leu Asn Gly
225                230               235             240

Tyr Val Phe Gly Thr Gly Thr Lys Leu Thr Val Leu
          245              250

```
<210> SEQ ID NO 38
<211> LENGTH: 864
<212> TYPE: DNA
<213> ORGANISM: Artificial Sequence
<220> FEATURE:
<223> OTHER INFORMATION: scFv sequence

<400> SEQUENCE: 38
gctctgcagg ctagtggtgg tggtggttct ggtggtggtg gttctggtgg tggtggttct      60
gctagccagg tgcagctggt ggaatctgag gctgaggtga agaagcctgg gtcctcggtg     120
aaggtctcct gcaaggcttc tggaggcacc ttcagcagct atgctatcag ctgggtgcga     180
caggcccctg gacaagggct cgagtggatg ggagggacca tccctatctt tggtacagca     240
aactacgcac agaagttcca gggcagagtc acgattaccg cggacgagtc cacgagcaca     300
gcctacatgg agctgagcag cctgagatct gaggacacgg ccgtgtatta ctgtgtcttg     360
ttgggtacaa ctatggttac gggatactac tttgactact ggggccaggg aaccctggtc     420
accgtctcct caggaattct aggatccggt ggcggtggca gcggcggtgg tggttccgga     480
ggcggcggtt ctaattttac gctgactcag ccccctcag cgtctgggac cccgggcag      540 agcgtcacca tctcttgttc tggaagcggc tcgaacatcg aaacaataa agtaaactgg      600 taccagcagc tcccaggaac ggccccaaa ctcctcatct atagtaataa tcagcggccc      660
tcaggggtcc ctgaccgatt ctctggctcc aagtctggca cctcagcctc cctggccatc     720
```

```
agtgggctcc agtctgagga tgaggctgat tattactgtg cagcatggga tgacagcctg    780
aatggttatg tcttcggaac tgggaccaag ctcaccgtcc tatccggaat tctagaacaa    840
aagcttattt ctgaagaaga cttg                                           864
```

<210> SEQ ID NO 39
<211> LENGTH: 250
<212> TYPE: PRT
<213> ORGANISM: Artificial Sequence
<220> FEATURE:
<223> OTHER INFORMATION: scFv sequence

<400> SEQUENCE: 39

```
Gln Val Gln Leu Gln Gln Gly Gly Ala Gly Leu Leu Lys Pro Ser Glu
1               5                   10                  15

Thr Leu Ser Leu Thr Cys Gly Val Tyr Gly Gly Ser Phe Ser Gly Tyr
            20                  25                  30

Tyr Trp Ser Trp Ile Arg Gln Ser Pro Gly Lys Gly Leu Glu Trp Ile
        35                  40                  45

Gly Glu Ile Asn His Ser Gly Ser Ala Asn Tyr Asn Pro Ser Val Lys
    50                  55                  60

Ser Arg Val Thr Ile Ser Val Asp Thr Ser Lys Asn Gln Phe Ser Leu
65                  70                  75                  80

Gln Leu Ser Ser Val Thr Ala Ala Asp Thr Ala Val Tyr Tyr Cys Ala
                85                  90                  95

Arg Asp Arg Ala Val Leu Thr Gly Glu Gly Trp Tyr Phe Asp Leu Trp
            100                 105                 110

Gly Arg Gly Thr Leu Val Thr Val Ser Ser Gly Ile Leu Gly Ser Gly
        115                 120                 125

Gly Gly Gly Ser Gly Gly Gly Gly Ser Gly Gly Gly Gly Ser Ser Tyr
    130                 135                 140

Glu Leu Thr Gln Pro Pro Ser Val Ser Val Ser Pro Gly Gln Thr Ala
145                 150                 155                 160

Ser Ile Thr Cys Ser Gly Asp Lys Leu Gly Asp Lys Tyr Thr Cys Trp
                165                 170                 175

Tyr Gln Gln Lys Pro Gly Gln Ser Pro Val Leu Val Leu Tyr Glu Asp
            180                 185                 190

Thr Lys Arg Pro Ser Gly Ile Pro Glu Arg Phe Ser Gly Ser Asn Ser
        195                 200                 205

Gly Asn Thr Ala Thr Leu Thr Ile Ser Arg Val Glu Ala Gly Asp Glu
    210                 215                 220

Ala Asp Tyr Tyr Cys Gln Leu Trp Asp Ser Ser Asp His Tyr Val
225                 230                 235                 240

Phe Gly Ser Gly Thr Lys Leu Thr Val Leu
                245                 250
```

<210> SEQ ID NO 40
<211> LENGTH: 835
<212> TYPE: DNA
<213> ORGANISM: Artificial Sequence
<220> FEATURE:
<223> OTHER INFORMATION: scFv sequence

<400> SEQUENCE: 40

```
ctggtggtgg tggttctgct agccaggtgc agctacagca gggggggcgca ggactgttga     60 agccttcgga gaccctgtcc ctcacgtgcg gtgtctatgg tggtctcttc agtggttact    120
attggagctg gattcgccag tccccaggaa aggggctgga atggattggg gaaatcaatc    180
```

-continued

```
atagtggaag cgccaactac aacccgtccg tcaagagtcg tgtcaccata tcagtagaca    240
cgtccaagaa tcagttctcc ctgcagttga gctctgtgac cgctgcggac acggccgtgt    300
actactgtgc gagagatagg gcggtgttaa cgggggaggg ctggtacttc gatctctggg    360
gccgtggtac cctggtcacc gtctcctcag gaattctagg atccggtggc ggtggcagcg    420
gcggtggtgg ttccggaggc ggcggttctt cctatgagct gacacagcca ccctcagtgt    480
ccgtgtcccc aggacagaca gccagcatca cctgctctgg agataaattg ggggataaat    540
atacttgttg gtatcagcag aagccaggcc agtcccctgt actggtcctc tatgaagata    600
ccaagcggcc ctcagggatc cctgagcgat tctctggctc caactctggg aacacggcca    660
ccctgaccat cagcagggtc gaagccgggg atgaggccga ctattactgt cagctgtggg    720
atagtagtag tgatcattat gtcttcggaa gtgggaccaa gctgaccgtc ctatccggaa    780
ttctagaaca aaagcttatt tcagaagaag acttgtaata gctcggcggc cgcat         835
```

<210> SEQ ID NO 41
<211> LENGTH: 268
<212> TYPE: PRT
<213> ORGANISM: Artificial Sequence
<220> FEATURE:
<223> OTHER INFORMATION: H6-MG (VH) / HL1-TO1 (VL) - furin (short)
      biosensor (protein)

<400> SEQUENCE: 41

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Ser
                20                  25                  30

His Tyr Tyr Trp Gly Trp Ile Arg Gln Pro Pro Gly Lys Gly Pro Glu
            35                  40                  45

Trp Ile Gly Ser Met Tyr Tyr Ser Gly Arg Thr Tyr Tyr Asn Pro Ala
        50                  55                  60

Leu Lys Ser Arg Val Thr Ile Ser Pro Asp Lys Ser Lys Asn Gln Phe
65                  70                  75                  80

Phe Leu Lys Leu Thr Ser Val Thr Ala Ala Asp Thr Ala Val Tyr Tyr
                85                  90                  95

Cys Ala Arg Glu Gly Pro Thr His Tyr Tyr Asp Asn Ser Gly Pro Ile
            100                 105                 110

Pro Ser Asp Glu Tyr Phe Gln His Trp Gly Gln Gly Thr Leu Val Thr
        115                 120                 125

Val Ser Ser Gly Ile Leu Gly Ser Arg Lys Lys Arg Ser Gly Ser Gly
    130                 135                 140

Gly Gly Gly Ser Gly Gly Gly Ser Gly Gly Gly Ser Asn Phe
145                 150                 155                 160

Met Leu Thr Gln Pro Pro Ser Ala Ser Gly Thr Pro Gly Gln Ser Val
                165                 170                 175

Thr Ile Ser Cys Ser Gly Ser Ser Asn Ile Gly Asn Asn Lys Val
            180                 185                 190

Asn Trp Tyr Gln Gln Leu Pro Gly Thr Ala Pro Lys Leu Leu Ile Tyr
        195                 200                 205

Ser Asn Asn Gln Arg Pro Ser Gly Val Pro Asp Arg Phe Ser Gly Ser
    210                 215                 220

Lys Ser Gly Thr Ser Ala Ser Leu Ala Ile Ser Gly Leu Gln Ser Glu
225                 230                 235                 240
```

```
Asp Glu Ala Asp Tyr Tyr Cys Ala Ala Trp Asp Asp Ser Leu Asn Gly
                245                 250                 255
Tyr Val Phe Gly Thr Gly Thr Lys Leu Thr Val Leu
        260                 265
```

<210> SEQ ID NO 42
<211> LENGTH: 1033
<212> TYPE: DNA
<213> ORGANISM: Artificial Sequence
<220> FEATURE:
<223> OTHER INFORMATION: H6-MG (VH) / HL1-TO1 (VL) - furin (short) biosensor (DNA)

<400> SEQUENCE: 42

```
actagcaaag gcagccccat aaacacacag tatgttttta aggacaatag ctcgacgatt      60
gaaggtagat acccatacga cgttccagac tacgctctgc aggctagtgg tggtggtggt     120
tctggtggtg gtggttctgg tggtggtggt tctgctagcc aggtgcagct gcaggagtcg     180
ggcccaggac tggtgaagcc ttcggagacc ctgtccctca cctgcactgt ctctggtgcc     240
tccatcagca gtagtcatta ctactgggc tggatccgcc agcccccagg aaggggcct      300
gagtggattg ggagtatgta ttatagtggg agaacgtact acaacccggc cctcaagagt     360
cgagtcacca tatcaccaga caagtcgaag aaccagttct tcttgaagtt gacctctgta     420
accgccgcgg acacggccgt gtattactgt gcgagggagg gacccacaca ttactatgat     480
aatagtggtc aataccttc ggatgagtat ttccagcact ggggccaggg taccctggtc      540
actgtctcct caggaattct aggatcgaga aagaagagat ctggatccgg tgcggtggc      600
agcggcggtg gtggttccgg aggcggcggt tctaatttta tgctgactca gccccctca      660
gcgtctggga cccccgggca gagcgtcacc atctcttgtt ctggaagcgg ctcgaacatc     720
ggaaacaata agtaaactg gtaccagcag ctcccaggaa cggccccaa actcctcatc       780
tatagtaata atcagcggcc ctcaggggtc cctgaccgat tctctggctc caagtctggc     840
acctcagcct ccctggccat cagtgggctc cagtctgagg atgaggctga ttattactgt     900
gcagcatggg atgacagcct gaatggttat gtcttcggaa ctgggaccaa gctcaccgtc     960
ctatccggaa ttctagaaca aaagcttatt tctgaagaag acttgtaata gctcggcggc    1020
cgcatcgaga tct                                                       1033
```

<210> SEQ ID NO 43
<211> LENGTH: 273
<212> TYPE: PRT
<213> ORGANISM: Artificial Sequence
<220> FEATURE:
<223> OTHER INFORMATION: H6-MG (VH) / HL1-TO1 (VL) - furin (long) biosensor (protein)

<400> SEQUENCE: 43

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Ala Ser Ile Ser Ser Ser
                20                  25                  30
His Tyr Tyr Trp Gly Trp Ile Arg Gln Pro Pro Gly Lys Gly Pro Glu
            35                  40                  45
Trp Ile Gly Ser Met Tyr Tyr Ser Gly Arg Thr Tyr Tyr Asn Pro Ala
        50                  55                  60
Leu Lys Ser Arg Val Thr Ile Ser Pro Asp Lys Ser Lys Asn Gln Phe
65                  70                  75                  80
```

```
Phe Leu Lys Leu Thr Ser Val Thr Ala Ala Asp Thr Ala Val Tyr Tyr
                 85                  90                  95
Cys Ala Arg Glu Gly Pro Thr His Tyr Tyr Asp Asn Ser Gly Pro Ile
            100                 105                 110
Pro Ser Asp Glu Tyr Phe Gln His Trp Gly Gln Gly Thr Leu Val Thr
        115                 120                 125
Val Ser Ser Gly Ile Leu Gly Ser Asn Ser Arg Lys Lys Arg Ser Thr
    130                 135                 140
Ser Ala Gly Ser Gly Gly Gly Gly Ser Gly Gly Gly Ser Gly Gly Gly
145                 150                 155                 160
Gly Gly Ser Asn Phe Met Leu Thr Gln Pro Pro Ser Ala Ser Gly Thr
                165                 170                 175
Pro Gly Gln Ser Val Thr Ile Ser Cys Ser Gly Ser Gly Ser Asn Ile
            180                 185                 190
Gly Asn Asn Lys Val Asn Trp Tyr Gln Gln Leu Pro Gly Thr Ala Pro
        195                 200                 205
Lys Leu Leu Ile Tyr Ser Asn Asn Gln Arg Pro Ser Gly Val Pro Asp
    210                 215                 220
Arg Phe Ser Gly Ser Lys Ser Gly Thr Ser Ala Ser Leu Ala Ile Ser
225                 230                 235                 240
Gly Leu Gln Ser Glu Asp Glu Ala Asp Tyr Tyr Cys Ala Ala Trp Asp
                245                 250                 255
Asp Ser Leu Asn Gly Tyr Val Phe Gly Thr Gly Thr Lys Leu Thr Val
            260                 265                 270
Leu

<210> SEQ ID NO 44
<211> LENGTH: 1048
<212> TYPE: DNA
<213> ORGANISM: Artificial Sequence
<220> FEATURE:
<223> OTHER INFORMATION: H6-MG (VH) / HL1-TO1 (VL) - furin (long)
      biosensor (DNA)

<400> SEQUENCE: 44
actagcaaag gcagccccat aaacacacag tatgttttta aggacaatag ctcgacgatt      60
gaaggtagat acccatacga cgttccagac tacgctctgc aggctagtgg tggtggtggt     120
tctggtggtg gtggttctgg tggtggtggt tctgctagcc aggtgcagct gcaggagtcg     180
ggcccaggac tggtgaagcc ttcggagacc ctgtccctca cctgcactgt ctctggtgcc     240
tccatcagca gtagtcatta ctactggggc tggatccgcc agcccccagg aaggggcct      300 gagtggattg ggagtatgta ttatagtggg agaacgtact acaacccggc cctcaagagt     360
cgagtcacca tatcaccaga caagtcgaag aaccagttct tcttgaagtt gacctctgta     420
accgccgcgg acacggccgt gtattactgt gcgagggagg acccacacac ttactatgat     480
aatagtggtc caatacctcc ggatgagtat ttccagcact ggggccaggg taccctggtc     540
actgtctcct caggaattct aggatcgaac tcgagaaaga gagatctac ctccgctgga      600 tccggtggcg gtggcagcgg cggtggtggt tccggaggcg gcggttctaa ttttatgctg     660
actcagcccc cctcagcgtc tgggaccccc gggcagagcg tcaccatctc ttgttctgga     720
agcggctcga acatcggaaa caataaagta aactggtacc agcagctccc aggaacggcc     780
cccaaactcc tcatctatag taataatcag cggccctcag gggtcctga ccgattctct       840 ggctccaagt ctggcaccc agcctccctg gccatcagtg gctccagtc tgaggatgag        900
```

```
gctgattatt actgtgcagc atgggatgac agcctgaatg gttatgtctt cggaactggg      960
accaagctca ccgtcctatc cggaattcta gaacaaaagc ttatttctga agaagacttg     1020
taatagctcg gcggccgcat cgagatct                                        1048
```

<210> SEQ ID NO 45
<211> LENGTH: 270
<212> TYPE: PRT
<213> ORGANISM: Artificial Sequence
<220> FEATURE:
<223> OTHER INFORMATION: H6-MG (VH) / HL1-TO1 (VL) - TEV protease
      biosensor (protein)

<400> SEQUENCE: 45

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Ser
            20                  25                  30

His Tyr Tyr Trp Gly Trp Ile Arg Gln Pro Pro Gly Lys Gly Pro Glu
        35                  40                  45

Trp Ile Gly Ser Met Tyr Tyr Ser Gly Arg Thr Tyr Tyr Asn Pro Ala
50                  55                  60

Leu Lys Ser Arg Val Thr Ile Ser Pro Asp Lys Ser Lys Asn Gln Phe
65                  70                  75                  80

Phe Leu Lys Leu Thr Ser Val Thr Ala Ala Asp Thr Ala Val Tyr Tyr
                85                  90                  95

Cys Ala Arg Glu Gly Pro Thr His Tyr Tyr Asp Asn Ser Gly Pro Ile
            100                 105                 110

Pro Ser Asp Glu Tyr Phe Gln His Trp Gly Gln Gly Thr Leu Val Thr
        115                 120                 125

Val Ser Ser Gly Ile Leu Gly Ser Glu Asn Leu Tyr Phe Glu Gly Arg
130                 135                 140

Ser Gly Gly Gly Gly Ser Gly Gly Gly Ser Gly Gly Gly Gly Ser
145                 150                 155                 160

Asn Phe Met Leu Thr Gln Pro Pro Ser Ala Ser Gly Thr Pro Gly Gln
                165                 170                 175

Ser Val Thr Ile Ser Cys Ser Gly Ser Asn Ile Gly Asn Asn
            180                 185                 190

Lys Val Asn Trp Tyr Gln Gln Leu Pro Gly Thr Ala Pro Lys Leu Leu
        195                 200                 205

Ile Tyr Ser Asn Asn Gln Arg Pro Ser Gly Val Pro Asp Arg Phe Ser
210                 215                 220

Gly Ser Lys Ser Gly Thr Ser Ala Ser Leu Ala Ile Ser Gly Leu Gln
225                 230                 235                 240

Ser Glu Asp Glu Ala Asp Tyr Tyr Cys Ala Ala Trp Asp Asp Ser Leu
                245                 250                 255

Asn Gly Tyr Val Phe Gly Thr Gly Thr Lys Leu Thr Val Leu
            260                 265                 270
```

<210> SEQ ID NO 46
<211> LENGTH: 1039
<212> TYPE: DNA
<213> ORGANISM: Artificial Sequence
<220> FEATURE:
<223> OTHER INFORMATION: H6-MG (VH) / HL1-TO1 (VL) - TEV protease
      biosensor (DNA)

<400> SEQUENCE: 46

```
actagcaaag gcagccccat aaacacacag tatgttttta aggacaatag ctcgacgatt      60
gaaggtagat acccatacga cgttccagac tacgctctgc aggctagtgg tggtggtggt     120
tctggtggtg gtggttctgg tggtggtggt tctgctagcc aggtgcagct gcaggagtcg    180
ggcccaggac tggtgaagcc ttcggagacc ctgtccctca cctgcactgt ctctggtgcc    240
tccatcagca gtagtcatta ctactggggc tggatccgcc agcccccagg aaggggcct     300
gagtggattg ggagtatgta ttatagtggg agaacgtact acaacccggc cctcaagagt    360
cgagtcacca tatcaccaga caagtcgaag aaccagttct tcttgaagtt gacctctgta    420
accgccgcgg acacggccgt gtattactgt gcgagggagg gacccacaca ttactatgat    480
aatagtggtc caataccttc ggatgagtat ttccagcact ggggccaggg taccctggtc    540
actgtctcct caggaattct aggatctgaa aacctatact ccaaggtcg  atccggtggc    600
ggtggcagcg gcggtggtgg ttccggaggc ggcggttcta attttatgct gactcagccc    660
ccctcagcgt ctgggacccc cgggcagagc gtcaccatct cttgttctgg aagcggctcg    720
aacatcggaa acaataaagt aaactggtac cagcagctcc caggaacggc ccccaaactc    780
ctcatctata gtaataatca gcggccctca ggggtccctg accgattctc tggctccaag    840
tctggcacct cagcctccct ggccatcagt gggctccagt ctgaggatga ggctgattat    900
tactgtgcag catgggatga cagcctgaat ggttatgtct tcggaactgg gaccaagctc    960
accgtcctat ccggaattct agaacaaaag cttatttctg aagaagactt gtaatagctc   1020
ggcggccgca tcgagatct                                                1039
```

<210> SEQ ID NO 47  
<211> LENGTH: 271  
<212> TYPE: PRT  
<213> ORGANISM: Artificial Sequence  
<220> FEATURE:  
<223> OTHER INFORMATION: H6-MG (VH) / HL1-TO1 (VL) - HRV-3C protease biosensor (protein)

<400> SEQUENCE: 47

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Ser
            20                  25                  30

His Tyr Tyr Trp Gly Trp Ile Arg Gln Pro Pro Gly Lys Gly Pro Glu
        35                  40                  45

Trp Ile Gly Ser Met Tyr Tyr Ser Gly Arg Thr Tyr Tyr Asn Pro Ala
    50                  55                  60

Leu Lys Ser Arg Val Thr Ile Ser Pro Asp Lys Ser Lys Asn Gln Phe
65                  70                  75                  80

Phe Leu Lys Leu Thr Ser Val Thr Ala Ala Asp Thr Ala Val Tyr Tyr
                85                  90                  95

Cys Ala Arg Glu Gly Pro Thr His Tyr Tyr Asp Asn Ser Gly Pro Ile
            100                 105                 110

Pro Ser Asp Glu Tyr Phe Gln His Trp Gly Gln Gly Thr Leu Val Thr
        115                 120                 125

Val Ser Ser Gly Ile Leu Gly Ser Glu Val Leu Phe Gln Gly Pro
    130                 135                 140

Gly Ser Gly Gly Gly Gly Ser Gly Gly Gly Gly Ser Gly Gly Gly Gly
145                 150                 155                 160

Ser Asn Phe Met Leu Thr Gln Pro Pro Ser Ala Ser Gly Thr Pro Gly
                165                 170                 175
```

Gln Ser Val Thr Ile Ser Cys Ser Gly Ser Gly Ser Asn Ile Gly Asn
                180                 185                 190

Asn Lys Val Asn Trp Tyr Gln Gln Leu Pro Gly Thr Ala Pro Lys Leu
            195                 200                 205

Leu Ile Tyr Ser Asn Asn Gln Arg Pro Ser Gly Val Pro Asp Arg Phe
        210                 215                 220

Ser Gly Ser Lys Ser Gly Thr Ser Ala Ser Leu Ala Ile Ser Gly Leu
225                 230                 235                 240

Gln Ser Glu Asp Glu Ala Asp Tyr Tyr Cys Ala Ala Trp Asp Asp Ser
                245                 250                 255

Leu Asn Gly Tyr Val Phe Gly Thr Gly Thr Lys Leu Thr Val Leu
            260                 265                 270

<210> SEQ ID NO 48
<211> LENGTH: 1042
<212> TYPE: DNA
<213> ORGANISM: Artificial Sequence
<220> FEATURE:
<223> OTHER INFORMATION: H6-MG (VH) / HL1-TO1 (VL) - HRV-3C protease
      biosensor (DNA)

<400> SEQUENCE: 48
actagcaaag gcagccccat aaacacacag tatgttttta aggacaatag ctcgacgatt     60
gaaggtagat acccatacga cgttccagac tacgctctgc aggctagtgg tggtggtggt    120
tctggtggtg gtggttctgg tggtggtggt tctgctagcc aggtgcagct gcaggagtcg    180
ggcccaggac tggtgaagcc ttcggagacc ctgtccctca cctgcactgt ctctggtgcc    240
tccatcagca gtagtcatta ctactggggc tggatccgcc agcccccagg aaggggcct     300
gagtggattg ggagtatgta ttatagtggg agaacgtact acaacccggc cctcaagagt    360
cgagtcacca tatcaccaga caagtcgaag aaccagttct tcttgaagtt gacctctgta    420
accgccgcgg acacggccgt gtattactgt gcgagggagg gacccacaca ttactatgat    480
aatagtggtc caataccttc ggatgagtat ttccagcact ggggccaggg taccctggtc    540
actgtctcct caggaattct aggatctttg gaagttttgt tccaaggtcc aggatccggt    600
ggcggtggca gcggcggtgg tggttccgga ggcggcggtt ctaattttat gctgactcag    660
ccccccctcag cgtctgggac ccccgggcag agcgtcacca tctcttgttc tggaagcggc    720
tcgaacatcg gaaacaataa agtaaactgg taccagcagc tcccaggaac ggcccccaaa    780
ctcctcatct atagtaataa tcagcggccc tcaggggtcc ctgaccgatt ctctggctcc    840
aagtctggca cctcagcctc cctggccatc agtgggctcc agtctgagga tgaggctgat    900
tattactgtg cagcatggga tgacagcctg aatggttatg tcttcggaac tgggaccaag    960
ctcaccgtcc tatccggaat tctagaacaa aagcttattt ctgaagaaga cttgtaatag   1020
ctcggcggcc gcatcgagat ct                                            1042

<210> SEQ ID NO 49
<211> LENGTH: 267
<212> TYPE: PRT
<213> ORGANISM: Artificial Sequence
<220> FEATURE:
<223> OTHER INFORMATION: H6-MG (VH) / HL1-TO1 (VL) - Caspase 1 biosensor
      (protein)

<400> SEQUENCE: 49

Gln Val Gln Leu Gln Glu Ser Gly Pro Gly Leu Val Lys Pro Ser Glu
1               5                   10                  15

```
Thr Leu Ser Leu Thr Cys Thr Val Ser Gly Ala Ser Ile Ser Ser Ser
            20                  25                  30

His Tyr Tyr Trp Gly Trp Ile Arg Gln Pro Pro Gly Lys Gly Pro Glu
            35                  40                  45

Trp Ile Gly Ser Met Tyr Tyr Ser Gly Arg Thr Tyr Tyr Asn Pro Ala
 50                  55                  60

Leu Lys Ser Arg Val Thr Ile Ser Pro Asp Lys Ser Lys Asn Gln Phe
 65                  70                  75                  80

Phe Leu Lys Leu Thr Ser Val Thr Ala Ala Asp Thr Ala Val Tyr Tyr
                 85                  90                  95

Cys Ala Arg Glu Gly Pro Thr His Tyr Tyr Asp Asn Ser Gly Pro Ile
            100                 105                 110

Pro Ser Asp Glu Tyr Phe Gln His Trp Gly Gln Gly Thr Leu Val Thr
            115                 120                 125

Val Ser Ser Gly Ile Leu Gly Ser Tyr Val Ala Asp Gly Ser Gly Gly
130                 135                 140

Gly Gly Ser Gly Gly Gly Ser Gly Gly Gly Ser Asn Phe Met
145                 150                 155                 160

Leu Thr Gln Pro Pro Ser Ala Ser Gly Thr Pro Gly Gln Ser Val Thr
                165                 170                 175

Ile Ser Cys Ser Gly Ser Gly Ser Asn Ile Gly Asn Asn Lys Val Asn
            180                 185                 190

Trp Tyr Gln Gln Leu Pro Gly Thr Ala Pro Lys Leu Leu Ile Tyr Ser
            195                 200                 205

Asn Asn Gln Arg Pro Ser Gly Val Pro Asp Arg Phe Ser Gly Ser Lys
            210                 215                 220

Ser Gly Thr Ser Ala Ser Leu Ala Ile Ser Gly Leu Gln Ser Glu Asp
225                 230                 235                 240

Glu Ala Asp Tyr Tyr Cys Ala Ala Trp Asp Asp Ser Leu Asn Gly Tyr
                245                 250                 255

Val Phe Gly Thr Gly Thr Lys Leu Thr Val Leu
            260                 265

<210> SEQ ID NO 50
<211> LENGTH: 1030
<212> TYPE: DNA
<213> ORGANISM: Artificial Sequence
<220> FEATURE:
<223> OTHER INFORMATION: H6-MG (VH) / HL1-TO1 (VL) - Caspase 1 biosensor
      (DNA)

<400> SEQUENCE: 50
actagcaaag gcagccccat aaacacacag tatgttttta aggacaatag ctcgacgatt      60
gaaggtagat acccatacga cgttccagac tacgctctgc aggctagtgg tggtggtggt     120
tctggtggtg gtggttctgg tggtggtggt tctgctagcc aggtgcagct gcaggagtcg     180
ggcccaggac tggtgaagcc ttcggagacc ctgtccctca cctgcactgt ctctggtgcc     240
tccatcagca gtagtcatta ctactggggc tggatccgcc agccccagg gaaggggcct     300 gagtggattg ggagtatgta ttatagtggg agaacgtact acaacccggc cctcaagagt     360
cgagtcacca tatcaccaga caagtcgaag aaccagttct tcttgaagtt gacctctgta     420
accgccgcgg acacggccgt gtattactgt gcgaggagg gacccacaca ttactatgat     480
aatagtggtc caatacctt ggatgagtat ttccagcact ggggccaggg taccctggtc     540
actgtctcct caggaattct aggatcttac gttgctgacg gatccggtgg cggtggcagc     600
```

```
ggcggtggtg gttccggagg cggcggttct aattttatgc tgactcagcc ccctcagcg     660 tctgggaccc ccgggcagag cgtcaccatc tcttgttctg gaagcggctc gaacatcgga    720
aacaataaag taaactggta ccagcagctc ccaggaacgg cccccaaact cctcatctat    780
agtaataatc agcggccctc aggggtccct gaccgattct ctggctccaa gtctggcacc    840
tcagcctccc tggccatcag tgggctccag tctgaggatg aggctgatta ttactgtgca    900
gcatgggata cagcctgaa tggttatgtc ttcggaactg ggaccaagct caccgtccta     960
tccggaattc tagaacaaaa gcttatttct gaagaagact tgtaatagct cggcggccgc   1020
atcgagatct                                                          1030
```

<210> SEQ ID NO 51
<211> LENGTH: 267
<212> TYPE: PRT
<213> ORGANISM: Artificial Sequence
<220> FEATURE:
<223> OTHER INFORMATION: H6-MG (VH) / HL1-TO1 (VL) - Caspase 3 biosensor
      (protein)

<400> SEQUENCE: 51

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Ser
            20                  25                  30

His Tyr Tyr Trp Gly Trp Ile Arg Gln Pro Pro Gly Lys Gly Pro Glu
        35                  40                  45

Trp Ile Gly Ser Met Tyr Tyr Ser Gly Arg Thr Tyr Tyr Asn Pro Ala
    50                  55                  60

Leu Lys Ser Arg Val Thr Ile Ser Pro Asp Lys Ser Lys Asn Gln Phe
65                  70                  75                  80

Phe Leu Lys Leu Thr Ser Val Thr Ala Ala Asp Thr Ala Val Tyr Tyr
                85                  90                  95

Cys Ala Arg Glu Gly Pro Thr His Tyr Tyr Asp Asn Ser Gly Pro Ile
            100                 105                 110

Pro Ser Asp Glu Tyr Phe Gln His Trp Gly Gln Gly Thr Leu Val Thr
        115                 120                 125

Val Ser Ser Gly Ile Leu Gly Ser Asp Glu Val Asp Arg Ser Gly Gly
    130                 135                 140

Gly Gly Ser Gly Gly Gly Gly Ser Gly Gly Gly Gly Ser Asn Phe Met
145                 150                 155                 160

Leu Thr Gln Pro Pro Ser Ala Ser Gly Thr Pro Gly Gln Ser Val Thr
                165                 170                 175

Ile Ser Cys Ser Gly Ser Gly Ser Asn Ile Gly Asn Asn Lys Val Asn
            180                 185                 190

Trp Tyr Gln Gln Leu Pro Gly Thr Ala Pro Lys Leu Leu Ile Tyr Ser
        195                 200                 205

Asn Asn Gln Arg Pro Ser Gly Val Pro Asp Arg Phe Ser Gly Ser Lys
    210                 215                 220

Ser Gly Thr Ser Ala Ser Leu Ala Ile Ser Gly Leu Gln Ser Glu Asp
225                 230                 235                 240

Glu Ala Asp Tyr Tyr Cys Ala Ala Trp Asp Asp Ser Leu Asn Gly Tyr
                245                 250                 255

Val Phe Gly Thr Gly Thr Lys Leu Thr Val Leu
            260                 265
```

<210> SEQ ID NO 52
<211> LENGTH: 1030
<212> TYPE: DNA
<213> ORGANISM: Artificial Sequence
<220> FEATURE:
<223> OTHER INFORMATION: H6-MG (VH) / HL1-TO1 (VL) - Caspase 3 biosensor
      (DNA)

<400> SEQUENCE: 52

```
actagcaaag gcagccccat aaacacacag tatgttttta aggacaatag ctcgacgatt      60
gaaggtagat acccatacga cgttccagac tacgctctgc aggctagtgg tggtggtggt     120
tctggtggtg gtggttctgg tggtggtggt tctgctagcc aggtgcagct gcaggagtcg     180
ggcccaggac tggtgaagcc ttcggagacc ctgtccctca cctgcactgt ctctggtgcc     240
tccatcagca gtagtcatta ctactgggc tggatccgcc agccccagg aaggggcct       300
gagtggattg ggagtatgta ttatagtggg agaacgtact acaacccggc cctcaagagt     360
cgagtcacca tatcaccaga caagtcgaag aaccagttct tcttgaagtt gacctctgta     420
accgccgcgg acacggccgt gtattactgt gcgagggagg gacccacaca ttactatgat     480
aatagtggtc caataccttc ggatgagtat ttccagcact ggggccaggg taccctggtc     540
actgtctcct caggaattct aggatctgac gaagttgacc gatccggtgg cggtggcagc     600
ggcggtggtg gttccggagg cggcggttct aattttatgc tgactcagcc ccctcagcg     660
tctgggaccc ccgggcagag cgtcaccatc tcttgttctg gaagcggctc gaacatcgga     720
aacaataaag taaactggta ccagcagctc ccaggaacgg cccccaaact cctcatctat     780
agtaataatc agcggccctc aggggtccct gaccgattct ctggctccaa gtctggcacc     840
tcagcctccc tggccatcag tgggctccag tctgaggatg aggctgatta ttactgtgca     900
gcatgggatg acagcctgaa tggttatgtc ttcggaactg ggaccaagct caccgtccta     960
tccggaattc tagaacaaaa gcttatttct gaagaagact tgtaatagct cggcggccgc    1020
atcgagatct                                                          1030
```

<210> SEQ ID NO 53
<211> LENGTH: 269
<212> TYPE: PRT
<213> ORGANISM: Artificial Sequence
<220> FEATURE:
<223> OTHER INFORMATION: H6-MG (VH) / HL1-TO1 (VL) - MMP25 biosensor
      (protein)

<400> SEQUENCE: 53

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Ser
            20                  25                  30

His Tyr Tyr Trp Gly Trp Ile Arg Gln Pro Pro Gly Lys Gly Pro Glu
        35                  40                  45

Trp Ile Gly Ser Met Tyr Tyr Ser Gly Arg Thr Tyr Tyr Asn Pro Ala
    50                  55                  60

Leu Lys Ser Arg Val Thr Ile Ser Pro Asp Lys Ser Lys Asn Gln Phe
65                  70                  75                  80

Phe Leu Lys Leu Thr Ser Val Thr Ala Ala Asp Thr Ala Val Tyr Tyr
                85                  90                  95

Cys Ala Arg Glu Gly Pro Thr His Tyr Tyr Asp Asn Ser Gly Pro Ile
            100                 105                 110
```

```
Pro Ser Asp Glu Tyr Phe Gln His Trp Gly Gln Gly Thr Leu Val Thr
            115                 120                 125
Val Ser Ser Gly Ile Leu Gly Ser Val Met Arg Leu Val Val Gly Ser
        130                 135                 140
Gly Gly Gly Gly Ser Gly Gly Gly Ser Gly Gly Gly Gly Gly Ser Asn
145                 150                 155                 160
Phe Met Leu Thr Gln Pro Pro Ser Ala Ser Gly Thr Pro Gly Gln Ser
                165                 170                 175
Val Thr Ile Ser Cys Ser Gly Ser Ser Asn Ile Gly Asn Asn Lys
            180                 185                 190
Val Asn Trp Tyr Gln Gln Leu Pro Gly Thr Ala Pro Lys Leu Leu Ile
        195                 200                 205
Tyr Ser Asn Asn Gln Arg Pro Ser Gly Val Pro Asp Arg Phe Ser Gly
    210                 215                 220
Ser Lys Ser Gly Thr Ser Ala Ser Leu Ala Ile Ser Gly Leu Gln Ser
225                 230                 235                 240
Glu Asp Glu Ala Asp Tyr Tyr Cys Ala Ala Trp Asp Asp Ser Leu Asn
                245                 250                 255
Gly Tyr Val Phe Gly Thr Gly Thr Lys Leu Thr Val Leu
            260                 265
```

<210> SEQ ID NO 54
<211> LENGTH: 1036
<212> TYPE: DNA
<213> ORGANISM: Artificial Sequence
<220> FEATURE:
<223> OTHER INFORMATION: H6-MG (VH) / HL1-TO1 (VL) - MMP25 biosensor
      (DNA)

<400> SEQUENCE: 54

```
actagcaaag gcagccccat aaacacacag tatgttttta aggacaatag ctcgacgatt      60
gaaggtagat acccatacga cgttccagac tacgctctgc aggctagtgg tggtggtggt     120
tctggtggtg gtggttctgg tggtggtggt tctgctagcc aggtgcagct gcaggagtcg     180
ggcccaggac tggtgaagcc ttcggagacc ctgtccctca cctgcactgt ctctggtgcc     240
tccatcagca gtagtcatta ctactggggc tggatccgcc agcccccagg aaggggcctc     300
gagtggattg ggagtatgta ttatagtggg agaacgtact acaacccggc cctcaagagt     360
cgagtcacca tcaccagaca agtcgaag aaccagttct tcttgaagtt gacctctgta     420
accgccgcgg acacggccgt gtattactgt gcgagggagg gacccacaca ttactatgat     480
aatagtggtc caataccttc ggatgagtat ttccagcact ggggccaggg taccctggtc     540
actgtctcct caggaattct aggatcggtc atgagattgg tcgtcggatc cggtggcggt     600
ggcagcggcg gtggtggttc cggaggcggc ggttctaatt ttatgctgac tcagccccc      660
tcagcgtctg gaccccccgg gcagagcgtc accatctctt gttctggaag cggctcgaac     720
atcggaaaca ataagtaaa ctggtaccag cagctcccag gaacggcccc caaactcctc      780
atctatagta ataatcagcg gccctcaggg gtccctgacc gattctctgg ctccaagtct     840
ggcacctcag cctccctggc catcagtggg ctccagtctg aggatgaggc tgattattac     900
tgtgcagcat gggatgacag cctgaatggt tatgtcttcg gaactgggac caagctcacc     960
gtcctatccg gaattctaga acaaaagctt atttctgaag aagacttgta atagctcggc    1020
ggccgcatcg agatct                                                   1036
```

<210> SEQ ID NO 55

<211> LENGTH: 272
<212> TYPE: PRT
<213> ORGANISM: Artificial Sequence
<220> FEATURE:
<223> OTHER INFORMATION: H6-MG (VH) / HL1-TO1 (VL) - PKA biosensor
      (protein)

<400> SEQUENCE: 55

Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Ser
            20                  25                  30

His Tyr Tyr Trp Gly Trp Ile Arg Gln Pro Pro Gly Lys Gly Pro Glu
        35                  40                  45

Trp Ile Gly Ser Met Tyr Tyr Ser Gly Arg Thr Tyr Tyr Asn Pro Ala
    50                  55                  60

Leu Lys Ser Arg Val Thr Ile Ser Pro Asp Lys Ser Lys Asn Gln Phe
65                  70                  75                  80

Phe Leu Lys Leu Thr Ser Val Thr Ala Ala Asp Thr Ala Val Tyr Tyr
                85                  90                  95

Cys Ala Arg Glu Gly Pro Thr His Tyr Tyr Asp Asn Ser Gly Pro Ile
            100                 105                 110

Pro Ser Asp Glu Tyr Phe Gln His Trp Gly Gln Gly Thr Leu Val Thr
        115                 120                 125

Val Ser Ser Gly Ile Leu Gly Ser Leu Leu Arg Arg Ala Ser Leu Gly
    130                 135                 140

Pro Gly Ser Gly Gly Gly Ser Gly Gly Gly Ser Gly Gly Gly
145                 150                 155                 160

Gly Ser Asn Phe Met Leu Thr Gln Pro Pro Ser Ala Ser Gly Thr Pro
                165                 170                 175

Gly Gln Ser Val Thr Ile Ser Cys Ser Gly Ser Ser Asn Ile Gly
            180                 185                 190

Asn Asn Lys Val Asn Trp Tyr Gln Gln Leu Pro Gly Thr Ala Pro Lys
        195                 200                 205

Leu Leu Ile Tyr Ser Asn Asn Gln Arg Pro Ser Gly Val Pro Asp Arg
    210                 215                 220

Phe Ser Gly Ser Lys Ser Gly Thr Ser Ala Ser Leu Ala Ile Ser Gly
225                 230                 235                 240

Leu Gln Ser Glu Asp Glu Ala Asp Tyr Tyr Cys Ala Ala Trp Asp Asp
                245                 250                 255

Ser Leu Asn Gly Tyr Val Phe Gly Thr Gly Thr Lys Leu Thr Val Leu
            260                 265                 270

<210> SEQ ID NO 56
<211> LENGTH: 1045
<212> TYPE: DNA
<213> ORGANISM: Artificial Sequence
<220> FEATURE:
<223> OTHER INFORMATION: H6-MG (VH) / HL1-TO1 (VL) - PKA biosensor (DNA)

<400> SEQUENCE: 56
actagcaaag gcagccccat aaacacacag tatgttttta aggacaatag ctcgacgatt      60
gaaggtagat acccatacga cgttccagac tacgctctgc aggctagtgg tggtggtggt     120
tctggtggtg gtggttctgg tggtggtggt tctgctagcc aggtgcagct gcaggagtcg     180
ggcccaggac tggtgaagcc ttcggagacc ctgtccctca cctgcactgt ctctggtgcc     240
tccatcagca gtagtcatta ctactggggc tggatccgcc agcccccagg aaggggcct      300

```
gagtggattg ggagtatgta ttatagtggg agaacgtact acaacccggc cctcaagagt    360
cgagtcacca tatcaccaga caagtcgaag aaccagttct tcttgaagtt gacctctgta    420
accgccgcgg acacggccgt gtattactgt gcgagggagg gacccacaca ttactatgat    480
aatagtggtc caatacccttc ggatgagtat ttccagcact ggggccaggg tacccctggtc   540
actgtctcct caggaattct aggatcgttg ttgagaagag ctagtttggg tccaggatcc    600
ggtggcggtg gcagcggcgg tggtggttcc ggaggcggcg gttctaatttt tatgctgact    660
cagccccct cagcgtctgg accccggg cagagcgtca ccatctcttg ttctggaagc       720
ggctcgaaca tcggaaacaa taaagtaaac tggtaccagc agctcccagg aacggccccc    780
aaactcctca tctatagtaa taatcagcgg ccctcagggg tccctgaccg attctctggc    840
tccaagtctg gcacctcagc ctccctggcc atcagtgggc tccagtctga ggatgaggct    900
gattattact gtgcagcatg ggatgacagc ctgaatggtt atgtcttcgg aactgggacc    960
aagctcaccg tcctatccgg aattctagaa caaaagctta tttctgaaga agacttgtaa   1020
tagctcggcg ccgcatcga gatct                                           1045
```

<210> SEQ ID NO 57
<211> LENGTH: 274
<212> TYPE: PRT
<213> ORGANISM: Artificial Sequence
<220> FEATURE:
<223> OTHER INFORMATION: H6-MG (VH) / HL1-TO1 (VL) - H3-K56 HAT
      biosensor (protein)

<400> SEQUENCE: 57

Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Ser
            20                  25                  30

His Tyr Tyr Trp Gly Trp Ile Arg Gln Pro Pro Gly Lys Gly Pro Glu
        35                  40                  45

Trp Ile Gly Ser Met Tyr Tyr Ser Gly Arg Thr Tyr Tyr Asn Pro Ala
    50                  55                  60

Leu Lys Ser Arg Val Thr Ile Ser Pro Asp Lys Ser Lys Asn Gln Phe
65                  70                  75                  80

Phe Leu Lys Leu Thr Ser Val Thr Ala Ala Asp Thr Ala Val Tyr Tyr
                85                  90                  95

Cys Ala Arg Glu Gly Pro Thr His Tyr Tyr Asp Asn Ser Gly Pro Ile
            100                 105                 110

Pro Ser Asp Glu Tyr Phe Gln His Trp Gly Gln Gly Thr Leu Val Thr
        115                 120                 125

Val Ser Ser Gly Ile Leu Gly Ser Ile Arg Arg Phe Gln Lys Ser Thr
    130                 135                 140

Asp Leu Leu Gly Ser Gly Gly Gly Ser Gly Gly Gly Ser Gly
145                 150                 155                 160

Gly Gly Gly Ser Asn Phe Met Leu Thr Gln Pro Ser Ala Ser Gly
                165                 170                 175

Thr Pro Gly Gln Ser Val Thr Ile Ser Cys Ser Gly Ser Gly Ser Asn
        180                 185                 190

Ile Gly Asn Asn Lys Val Asn Trp Tyr Gln Gln Leu Pro Gly Thr Ala
    195                 200                 205

Pro Lys Leu Leu Ile Tyr Ser Asn Asn Gln Arg Pro Ser Gly Val Pro
    210                 215                 220

Asp Arg Phe Ser Gly Ser Lys Ser Gly Thr Ser Ala Ser Leu Ala Ile
225                 230                 235                 240

Ser Gly Leu Gln Ser Glu Asp Glu Ala Asp Tyr Tyr Cys Ala Ala Trp
            245                 250                 255

Asp Asp Ser Leu Asn Gly Tyr Val Phe Gly Thr Gly Thr Lys Leu Thr
        260                 265                 270

Val Leu

<210> SEQ ID NO 58
<211> LENGTH: 1051
<212> TYPE: DNA
<213> ORGANISM: Artificial Sequence
<220> FEATURE:
<223> OTHER INFORMATION: H6-MG (VH) / HL1-TO1 (VL) - H3-K56 HAT
      biosensor (DNA)

<400> SEQUENCE: 58
actagcaaag gcagccccat aaacacacag tatgttttta aggacaatag ctcgacgatt      60
gaaggtagat acccatacga cgttccagac tacgctctgc aggctagtgg tggtggtggt     120
tctggtggtg gtggttctgg tggtggtggt tctgctagcc aggtgcagct gcaggagtcg     180
ggcccaggac tggtgaagcc ttcggagacc ctgtccctca cctgcactgt ctctggtgcc     240
tccatcagca gtagtcatta ctactggggc tggatccgcc agcccccagg aaggggcct      300 gagtggattg ggagtatgta ttatagtggg agaacgtact acaacccggc cctcaagagt     360
cgagtcacca tatcaccaga caagtcgaag aaccagttct tcttgaagtt gacctctgta     420
accgccgcgg acacggccgt gtattactgt gcgagggagg gacccacaca ttactatgat     480
aatagtggtc caataccttc ggatgagtat ttccagcact ggggccaggg taccctggtc     540
actgtctcct caggaattct aggatcgatc agaagattcc aaaagtccac cgacttgttg     600
ggatccggtg gcggtggcag cggcggtggt ggttccggag gcggcggttc taattttatg     660
ctgactcagc cccctcagc gtctgggacc ccgggcaga gcgtcaccat ctcttgttct      720
ggaagcggct cgaacatcgg aaacaataaa gtaaactggt accagcagct cccaggaacg     780
gcccccaaac tcctcatcta tagtaataat cagcggccct cagggtccc tgaccgattc      840 tctggctcca gtctggcac ctcagcctcc ctggccatca gtgggctcca gtctgaggat      900
gaggctgatt attactgtgc agcatgggat gacagcctga tggttatgt cttcggaact      960 gggaccaagc tcaccgtcct atccggaatt ctagaacaaa agcttatttc tgaagaagac    1020
ttgtaatagc tcggcggccg catcgagatc t                                   1051

<210> SEQ ID NO 59
<211> LENGTH: 7
<212> TYPE: PRT
<213> ORGANISM: Artificial Sequence
<220> FEATURE:
<223> OTHER INFORMATION: PKA kemptide phosphorylation sequence

<400> SEQUENCE: 59

Leu Arg Arg Ala Ser Leu Gly
1               5

<210> SEQ ID NO 60
<211> LENGTH: 7
<212> TYPE: PRT
<213> ORGANISM: Artificial Sequence
<220> FEATURE:
<223> OTHER INFORMATION: modified PKA kemptide phosphorylation sequence

```
<400> SEQUENCE: 60

Leu Arg Arg Ala Ser Leu Pro
1               5

<210> SEQ ID NO 61
<211> LENGTH: 40
<212> TYPE: DNA
<213> ORGANISM: Artificial Sequence
<220> FEATURE:
<223> OTHER INFORMATION: forward primer for amplifying and SfiI-tailing
      the H6-MG gene

<400> SEQUENCE: 61
ggcccagccg gccatggcgc aggtgcagct gcaggagtgc                              40

<210> SEQ ID NO 62
<211> LENGTH: 36
<212> TYPE: DNA
<213> ORGANISM: Artificial Sequence
<220> FEATURE:
<223> OTHER INFORMATION: reverse primer for amplifying and SfiI-tailing
      the H6-MG gene

<400> SEQUENCE: 62
ggcccccgag gcctcggaga cagtgaccag ggtacc                                  36

<210> SEQ ID NO 63
<211> LENGTH: 35
<212> TYPE: DNA
<213> ORGANISM: Artificial Sequence
<220> FEATURE:
<223> OTHER INFORMATION: reverse primer for amplifying and SfiI-tailing
      two-domain hybrid

<400> SEQUENCE: 63
ggcccccgag gccctagga cggtgagctt ggtcc                                    35

<210> SEQ ID NO 64
<211> LENGTH: 5
<212> TYPE: PRT
<213> ORGANISM: Artificial Sequence
<220> FEATURE:
<223> OTHER INFORMATION: consensus recognition sequence for furin
      protease
<220> FEATURE:
<221> NAME/KEY: misc_feature
<222> LOCATION: (2)
<223> OTHER INFORMATION: Xaa is any amino acid
<220> FEATURE:
<221> NAME/KEY: misc_feature
<222> LOCATION: (3)
<223> OTHER INFORMATION: Xaa is Lys or Arg

<400> SEQUENCE: 64

Arg Xaa Xaa Arg Ser
1               5
```